(12) United States Patent
Coffin

(10) Patent No.: US 12,049,647 B2
(45) Date of Patent: *Jul. 30, 2024

(54) ENGINEERED VIRUS

(71) Applicant: Replimune Limited, Oxfordshire (GB)

(72) Inventor: Robert Stuart Coffin, London (GB)

(73) Assignee: Replimune Limited (GB)

( * ) Notice: Subject to any disclaimer, the term of this patent is extended or adjusted under 35 U.S.C. 154(b) by 264 days.

This patent is subject to a terminal disclaimer.

(21) Appl. No.: 17/164,635

(22) Filed: Feb. 1, 2021

(65) Prior Publication Data

US 2021/0254019 A1 Aug. 19, 2021

Related U.S. Application Data

(63) Continuation of application No. 16/068,830, filed as application No. PCT/GB2017/050038 on Jan. 9, 2017, now Pat. No. 10,947,513.

(30) Foreign Application Priority Data

| Jan. 8, 2016 | (GB) | 1600380 |
|---|---|---|
| Jan. 8, 2016 | (GB) | 1600381 |
| Jan. 8, 2016 | (GB) | 1600382 |

(51) Int. Cl.

| C12N 7/00 | (2006.01) |
| A61K 35/763 | (2015.01) |
| A61K 39/395 | (2006.01) |
| A61K 45/06 | (2006.01) |
| A61P 35/00 | (2006.01) |
| C07K 14/005 | (2006.01) |
| C07K 14/535 | (2006.01) |
| C07K 16/28 | (2006.01) |
| A61K 39/00 | (2006.01) |

(52) U.S. Cl.
CPC .............. *C12N 7/00* (2013.01); *A61K 35/763* (2013.01); *A61K 39/3955* (2013.01); *A61K 39/39558* (2013.01); *A61K 45/06* (2013.01); *A61P 35/00* (2018.01); *C07K 14/005* (2013.01); *C07K 14/535* (2013.01); *C07K 16/2818* (2013.01); *A61K 2039/505* (2013.01); *C12N 2710/16621* (2013.01); *C12N 2710/16622* (2013.01); *C12N 2710/16632* (2013.01); *C12N 2710/16633* (2013.01); *C12N 2710/16643* (2013.01); *C12N 2740/13022* (2013.01)

(58) Field of Classification Search
CPC . A61K 35/763; A61K 39/39558; A61P 35/00; C07K 16/2818; C07K 14/5434; C07K 14/55; C07K 14/535; C12N 15/86; C12N 2710/16632; C12N 2710/16643

See application file for complete search history.

(56) References Cited

U.S. PATENT DOCUMENTS

| 5,122,458 | A | 6/1992 | Post et al. |
|---|---|---|---|
| 5,168,062 | A | 12/1992 | Stinski |
| 5,288,641 | A | 2/1994 | Roizman |
| 5,328,688 | A | 7/1994 | Roizman |
| 5,385,839 | A | 1/1995 | Stinski |
| 5,599,691 | A | 2/1997 | Roizman |
| 5,602,007 | A | 2/1997 | Dunn et al. |
| 5,698,531 | A | 12/1997 | Nabel et al. |
| 5,824,318 | A | 10/1998 | Mohr et al. |
| 5,846,707 | A | 12/1998 | Roizman |
| 6,040,169 | A | 3/2000 | Brown et al. |
| 6,071,692 | A | 6/2000 | Roizman |
| 6,120,773 | A | 9/2000 | Roizman |
| 6,172,047 | B1 | 1/2001 | Roizman et al. |
| 6,297,219 | B1 | 10/2001 | Nabel et al. |
| 6,340,673 | B1 | 1/2002 | Roizman et al. |
| 6,423,528 | B1 | 7/2002 | Brown et al. |
| 6,428,968 | B1 | 8/2002 | Molnar-Kimber et al. |
| 6,649,157 | B2 | 11/2003 | Coffey et al. |
| 6,770,274 | B1 | 8/2004 | Martuza et al. |
| 7,063,835 | B2 | 6/2006 | Coffin |
| 7,223,593 | B2 | 5/2007 | Coffin |
| 7,537,924 | B2 | 5/2009 | Coffin |
| 7,749,745 | B2 | 7/2010 | Johnson et al. |
| 7,981,669 | B2 | 7/2011 | Coffin et al. |
| 8,273,568 | B2 | 9/2012 | Martuza et al. |
| 8,277,818 | B2 | 10/2012 | Coffin |
| 8,361,978 | B2 | 1/2013 | Rabkin et al. |
| 8,470,577 | B2 | 6/2013 | Johnson et al. |
| 8,679,830 | B2 | 3/2014 | Coffin et al. |
| 8,680,068 | B2 | 3/2014 | Coffin |
| 8,703,120 | B2 | 4/2014 | Martuza et al. |
| 8,871,193 | B2 | 10/2014 | Johnson et al. |

(Continued)

FOREIGN PATENT DOCUMENTS

| EP | 1235853 B1 | 7/2009 |
| JP | 2013511549 A | 4/2013 |

(Continued)

OTHER PUBLICATIONS

Carson et al. Drug. Future, 2010, vol. 35, (3) pp. 183-195.*
Marabelle et al. Clinal Cancer Research Oct. 1, 2013;19(19): 5261-5263.*
Alekseenko et al. Journal of Translational Medicine , 2015, 13:78, p. 1-16.*
Carson et al., "Oncolytic Herpe Simplex Virus 1 (HSV-1) Vectors: Increasing Treatment Efficacy and Range Throught Strategic Virus Design", Drugs Future. 2010,35(3): 183-195.

(Continued)

*Primary Examiner* — Bao Q Li

(74) *Attorney, Agent, or Firm* — Norton Rose Fulbright US LLP

(57) ABSTRACT

The present invention relates to oncolytic virus comprising: (i) a GM-CSF-encoding gene; and (ii) an immune co-stimulatory pathway activating molecule or an immune co-stimulatory pathway activating molecule-encoding gene.

40 Claims, 33 Drawing Sheets

Specification includes a Sequence Listing.

(56) References Cited

U.S. PATENT DOCUMENTS

| | | | |
|---|---|---|---|
| 8,986,672 B2 | 3/2015 | Zhang et al. | |
| 9,487,581 B2 | 11/2016 | Abate et al. | |
| 9,492,482 B2 | 11/2016 | Beech et al. | |
| 9,827,307 B2 | 11/2017 | Rabkin et al. | |
| 9,868,961 B2 | 1/2018 | Allison et al. | |
| 10,039,796 B2 | 8/2018 | Zhang et al. | |
| 10,287,252 B2 | 5/2019 | Cowley et al. | |
| 10,301,600 B2 | 5/2019 | Coffin | |
| 10,570,377 B2 | 2/2020 | Coffin | |
| 10,612,005 B2 | 4/2020 | Coffin | |
| 10,626,377 B2 * | 4/2020 | Coffin | C07K 16/2818 |
| 10,765,710 B2 | 9/2020 | Zitvogel et al. | |
| 10,947,513 B2 * | 3/2021 | Coffin | C07K 16/2818 |
| 11,427,810 B2 * | 8/2022 | Coffin | C07K 16/2818 |
| 11,473,063 B2 * | 10/2022 | Coffin | A61K 39/3955 |
| 2003/0091537 A1 | 5/2003 | Coffin | |
| 2008/0014175 A1 | 1/2008 | Hallahan et al. | |
| 2010/0297072 A1 | 11/2010 | DePinho | |
| 2013/0202639 A1 | 8/2013 | Kousoulas et al. | |
| 2014/0154216 A1 | 6/2014 | Coffin | |
| 2014/0271677 A1 | 9/2014 | Palese et al. | |
| 2015/0232812 A1 | 8/2015 | Coffin | |
| 2015/0283234 A1 | 10/2015 | Graziano et al. | |
| 2016/0040186 A1 | 2/2016 | Liu | |
| 2021/0252135 A1 | 8/2021 | Coffin | |

FOREIGN PATENT DOCUMENTS

| | | |
|---|---|---|
| JP | 2015/508156 A | 3/2015 |
| JP | 2016509045 A | 3/2016 |
| WO | 97/12623 A1 | 4/1997 |
| WO | 9830707 A2 | 7/1998 |
| WO | 2001/53505 A2 | 7/2001 |
| WO | 2001/53506 A2 | 7/2001 |
| WO | 2005/011715 A1 | 2/2005 |
| WO | 2006/002394 A2 | 1/2006 |
| WO | 2006/048749 A1 | 5/2006 |
| WO | 2007/052029 A1 | 5/2007 |
| WO | 2007/123737 A2 | 11/2007 |
| WO | 2011063309 A1 | 5/2011 |
| WO | 2011/118866 A1 | 9/2011 |
| WO | 2012/038606 A1 | 3/2012 |
| WO | 2013/038066 A1 | 3/2013 |
| WO | 2013112942 A1 | 8/2013 |
| WO | 2014/022138 A2 | 2/2014 |
| WO | 2014/036412 A2 | 3/2014 |
| WO | 2014/066532 A1 | 5/2014 |
| WO | 2014128235 A1 | 8/2014 |
| WO | 2015032755 A1 | 3/2015 |
| WO | 2015/059303 A1 | 4/2015 |
| WO | 2015/077624 A1 | 5/2015 |
| WO | 2015066042 A1 | 5/2015 |
| WO | 2015/128313 A1 | 9/2015 |
| WO | 2015/153417 A1 | 10/2015 |
| WO | 2016/008976 A1 | 1/2016 |
| WO | 2016/118865 A1 | 7/2016 |
| WO | 2017/118864 A1 | 7/2017 |
| WO | 2017/118866 A1 | 7/2017 |
| WO | 2017118867 A1 | 7/2017 |
| WO | 2017/181420 A1 | 10/2017 |
| WO | 2018127713 A1 | 7/2018 |

OTHER PUBLICATIONS

Fransen et al., "Controlled Local Delivery of CTLA-4 Blocking Antibody Induces CD8+ T-Cell-Dependent Tumor Eradication and Decreaes Risk of Toxic Side Effects" Clin Cancer Res. 2013, 19(19):5381-9.

Hooren et al., "Abstract B103: Intralesional administration of CTLA-4 blocking monoclonal antibodies as a means to optimize bladder cancer therapy", Cancer Immunol Res. 2016,4 (11_ Supplement): B103.

Hooren et al., "Local checkpoint inhibition of CTLA-4 as a monotherapy or in combination with anti-PD1 prevents the growth of murine bladder cancer" Eur J Immunol. 2017,47(2):385-393.

Marabelle et al., "Intratumoral Anti-CTLA-4 Therapy: Enhancing Efficacy While Avoiding Toxicity", Clin Cancer Res. 2013, 19(19):5261-3.

Annex A—WO 2017/118864—Figures 3 and 4 published Jul. 13, 2017.

Terada, K. et al: "Development of a rapid method to generate multiple oncolytic HSV vectors and their in vivo evaluation using syngeneic mouse tumor models", Gene Therapy, vol. 13, No. 8, Apr. 1, 2006 (Apr. 1, 2006), pp. 705-714, Nature Publishing Group, London, GB.

Bateman et al. Cancer Res. Mar. 15, 2000;60(6):1492-7.

Bateman et al. Cancer Res. Nov. 15, 2002;62(22):6566-78.

Haswell et al Eur J Immunol 2001 31 3094-3100.

Hetrologous Expression. In Binder, Hirokawa and Windorst (eds.)—Encyclopedia of Neuroscience. (2009) Springer, Berlin, Heidleberg Https://Doi.org/10.1007/978-3-540-29678-2_2190.

Hoffmann et al. World J Gastroenterol. Jun. 14, 2007;13(22):3063-70.

Hoffmann et al. World J Gastroenterol. Mar. 28, 2008 14(12):1842-1850.

Huang et al., Mol Ther, Feb. 2010, vol. 18, No. 2, pp. 264-274.

IGI Global "What is Heterologous Expression" retrieved from https://www.igiglobal.com/dictionary/heterologousexpression/49470.

Kanagavelu et al PlosOne 2014, 9, 2, e90100.

Kanagavelu et al Vaccine 2012 30 691-701.

Kasuya et al., Journal of Japan Surgical Society, 2006, 107, Extra Issue (2), p. 369, No. PS-005-8.

Kim et al Cancer Res 2009, 69, 21, 8516-8525.

Li et al. Int. J. Cancer 2008, 123: 493-499.

Nakano et al., Journal of Japan Surgical Society, 2001,102, Extra Issue, p. 82, No. SF4e-4.

Patentee's response to EPO communication dtd Sep. 25, 2009, EP No. 17701906.

Yi et al Cancer Res 2007, 67 20 10027-10037.

Allison, et al; "Discovery of Cancer Therapy by Inhibition of Negative Immune Regulation"; The Nobel Assembly at Karolinska Institutet; 2018 Nobel Prize in Physiology of Medicine.

Cell Signaling Technology; Immune Checkpoint Signaling in the Tumor Microenvironment; Mar. 2018.

Chou et al., "Mapping of Herpes Simplex Virus-1 Neurovirulence to ?134.5, a Gene Nonessential for Growth in Culture," Science, 1990, 250(4985):1262-1266.

Du et al., "Tumor-specific oncolytic adenoviruses expressing granulocyte macrophage colony-stimulating factor or anti-CTLA4 antibody for the treatment of cancers," Cancer Gene Therapy, 2014, 21(8):340-348.

Gangi et al., "The safety of talimogene laherparepvec for the treatment of advanced melanoma," Expert Opinion on Drug Safety, 2016, pp. 1-5.

Gibney et al., "Preliminary results from a phase 1/2 study of INCB024360 combined with ipilimumab (ipi) in patients (pts) with melanoma." 2014 ASCO Annual Meeting, No. 3010.

International Search Report and Written Opinion issued in International Patent Application No. PCT/GB2017/050038, dated Apr. 24, 2017.

Liu et al., "ICP34.5 deleted herpes simplex cirus with enhanced oncolytic, immune stimulating, and anti-tumour properties," Gene Therapy, 2003, 10(4):292-303.

Loskog, Angelica, "Immunostimulatory Gene Therapy Using Oncolytic Viruses as Vehicles," Viruses, 2015, 7:5780-5791.

MacLean et al., "Herpes simplex cirus type 1 deletion variants 1714 and 1716 pinpoint neurovirulence-related sequences in Glasgow strain 17 + between immediate early gene 1 and the 'a' sequence," Journal of General Virology, 1991, 72:631-639.

Office Action issued in European Patent Application No. 1770385, dated May 21, 2019.

Piasecki et al., "Talilmogene laherparepvec increases the anti-tumor efficacy of the anti-PD-1 immune checkpoint plockade," AACR Annual Meeting Presentation Abstract, Apr. 19, 2015.

(56) References Cited

OTHER PUBLICATIONS

Reese, "Abstract IA24: New frontiers in oncolytic virus therapy," Cancer Immunology Research, 2016, 4 (11):1A24-1A24.
Robinson et al., "Novel Immunocompetent Murine Tumor Model for Evaluation of Conditionally Replication-Competent (Oncolytic) Murine Adenoviral Vectors," Journal of Virology, 2009, 83(8):3450-3462.
Senzer et al., "Phase II Clinical Trial of a Granulocyte-Macrophage Colony-Stimulating Factor-Encoding, Second-Generation Oncolytic herpesvirus in Patients with Unresectable Metastatic Melanoma" Journal of Clinical Oncology, 2009, 27(34):5763-5771.
Simpson et al., "Combination of a Fusogenic Glycoprotein, Prodrug activation, and Oncolytic Herpes Simplex Virus for Enhanced Local Tumor Control," Cancer Research, 2006, 66(9):4835-4842.
Sokolowski et al., "Oncolytic virotherapy using herpes simplex virus: how far have we come?" Oncolytic Virotherapy, 2015, 4:207-219.
Third Party Submission submitted in Related U.S. Appl. No. 16/068,816, dated Jul. 16, 2019.
Third Party Submission submitted in Related U.S. Appl. No. 16/068,823, dated Jul. 18, 2019.
Third Party Submission submitted in Related U.S. Appl. No. 16/068,826, dated Aug. 7, 2019.
Todo, Tomoki, Armed oncolytic herpes simplex viruses for brain tumor therapy, 208-213, Cell Adhesion* Migration 2:3, Jul./Aug./Sep. 2008.
Yan et al., "Developing Novel Oncolytic Adenoviruses through Bioselection," Journal of Virology, 2003, 77 (4):2640-2650.
Robbins et al; "Viral Vectors for Gene Therapy"; Pharmacol, Ther.; vol. 80, No. 1; pp. 35-47; 1998.
Altschul, S F et al (1990) J Mol Biol 215:403-10.
Altschul, S.F. (1993) J Mol Evol 36:290-300.
Devereux et al (1984) Nucleic Acids Research 12, p. 387-395.
Diefenbach et al., "Oncolytic virotherapy using herpes simplex virus: how far have we come?" Oncolytic Virotherapy, Nov. 1, 2015 (Nov. 1, 2015), p. 207.
Heinkoff and Heinkoff (1992) Proc. Natl. Acad. Sci. USA 89:10915-10919.
Inouye et al., "Codon optimization of genes for efficient protein expression in mammalian cells by selection of only preferred human codons", Protein Expression and Purification, 2015, 109:47-54.
Karlin and Altschul (1993) Proc. Natl. Acad. Sci. USA 90:5873-5787.
Schirrmann et al., "Transient Production of scFv-Fc Fusion Proteins in Mammalian Cells", Antibody Engineering, 2010, vol. 2; Chapter 30, p. 387-398, © Springer-Verlag Berlin Heidelberg.
Shan et al., "Characterization of scFv-Ig Constructs Generated from the Anti-CD20 mAb 1F5 Using Linker Peptides of Varying Lengths", Journal of Immunology, 1999, 162:6589-6595.
Statement of Grounds of Opposition from the Opponent, Margaret Dixon Limited, dated Jun. 7, 2021, EP3400293 (EP Appl. No. 17701910.6).
Ahmed et al, Intratumoral expression of a fusogenic membrane glycoprotein enhances the efficacy of replicating adenovirus therapy, 10 Gene Therapy 1663-71 (2003).
Asada, Treatment of Human Cancer with Mumps Virus, 34(6) Cancer 1907-28 (Dec. 1974).
Balvay et al. Translational control of retroviruses, 5 Nature Reviews Microbiology 128-140 (Feb. 2007).
Belsham and Sonenberg, RNA-protein interactions in regulation of picornavirus RNA translation, 60(3) Microbiological Reviews 499-511 (Sep. 1996).
Bett et al. Packaging capacity and stability of human adenovirus type 5 vectors, 67(10) J. Virol. 5911-21 (Oct. 1993).
Blechacz et al. Engineered Measles Virus as a Novel Oncolytic Viral Therapy System for Hepatocellular Carcinoma, 44 (6) Hepatology 1465-77 (Dec. 2006).
Brochu-Lafontaine and Lemay, Addition of exogenous polypeptides on the mammalian reovirus outer capsid using reverse genetics, 179 J. Virol. Methods 342-350 (2012).
Carter et al. Identification of an overprinting gene in Merkel cell polyomavirus provides evolutionary insight into the birth of viral genes, 110(31) Proceedings of the National Academy of Sciences 12744-49 (Jul. 2013).
Choi et al. Polymeric oncolytic adenovirus for cancer gene therapy, 219 Journal of Controlled Release 181-191 (2015).
Compilation of Virus Information from Swiss Institute of Bioinformatics retrieved on Nov. 3, 2021, available at https://viralzone.expasy.org/.
Croyle et al. PEGylation of a Vesicular Stomatitis Virus G Pseudotyped Lentivirus Vector Prevents Inactivation in Serum, 78(2) Journal of Virology 912-921 (Jan. 2004).
Danthinne and Imperiale, Production of first generation adenovirus vectors: a review, 7 Gene Therapy 1707-14 (2000).
Declaration of Dr. Sylvia D. Hall-Ellis dated Nov. 29, 2021 and Curriculum vitae.
Declaration of John C. Bell, Ph.D. dated Dec. 14, 2021 and Curriculum vitae.
Deguchi et al. Combination of the Tumor Angiogenesis Inhibitor Bevacizumab and Intratumoral Oncolytic Herpes Virus Injections as a Treatment Strategy for Human Gastric Cancers, 59(118) Hepatogastroenterology 1844-50 (Sep. 2012).
Dikstein, The unexpected traits associated with core promoter elements, 2(5) Transcription 201-206 (Sep. 2011).
Documents filed on Jul. 9, 2018 in U.S. Appl. No. 16/068,830, including original application, preliminary amendment, application data sheet, search report, and transmittal form.
Donovan-Banfield et al. Deep splicing plasticity of the human adenovirus type 5 transcriptome drives virus evolution, 3 Communications Biology (2020) 124.
Ebert et al. Syncytia Induction Enhances the Oncolytic Potential of Vesicular Stomatitis Virus in Virotherapy for Cancer. 64 Cancer Research 3265-3270 (May 2004).
Engeland et al. CTLA-4 and PD-L1 Checkpoint Blockade Enhances Oncolytic Measles Virus Therapy, 22(11) Molecular Therapy 1949-59 (Nov. 2014).
Excerpts from S. Baron (Ed.), Medical Microbiology, 4th. Ed. University of Texas Medical Branch at Galveston (1996).
Fu et al. Expression of a Fusogenic Membrane Glycoprotein by an Oncolytic Herpes Simplex Virus Potentiates the Viral Antitumor Effect, 7(6) Molecular Therapy 748-754 (Jun. 2003).
Fukuhara et al. Triple Gene-Deleted Oncolytic Herpes Simplex Virus Vector Double-Armed with Interleukin 18 and Soluble B7-1 Constructed by Bacterial Artificial Chromosome-Mediated System, 65(23) Cancer Res. 10663-68 (Dec. 2005).
Grandi, et al., Cancer Gene Therapy (2010) 17, 655-663 (Year: 2010).
Guedan et al. GALVexpression enhances the therapeutic efficacy of an oncolytic adenovirus by inducing cell fusion and enhancing virus distribution, 19 Gene Therapy 1048-57 (2012).
Gómez-Treviño et al. Effects of adenovirus-mediated SV5 fusogenic glycoprotein expression on tumor cells, 5 J. Gene Med. (2003) 483-492.
Herpesviridae Information from Virus Pathogen Resource (ViPR) retrieved on Nov. 4, 2021, available at: https://www.viprbrc.org/brc/aboutPathogen.spg7decoratoiHierpes.
Hillier et al. Genomics in C. elegans: so many genes, such a little worm, 15 Genome Research 1651-60 (2005).
Ho et al. Unconventional viral gene expression mechanisms as therapeutic targets, 593 Nature 362-371 (May 2021).
International Search Report for International Patent Application No. PCT/EP2015/066263, mailed from European Patent Office Oct. 7, 2015.
International Search Report for International Patent Application No. PCT/FI2009/051025, mailed from European Patent Office Mar. 24, 2010.
Ishihara et al. Systemic CD8+ T Cell-Mediated Tumoricidal Effects by Intratumoral Treatment of Oncolytic Herpes Simplex Virus with the Agonistic Monoclonal Antibody for Murine Glucocorticoid-Induced Tumor Necrosis Factor Receptor, 9(8) PLoS One e104669 (Aug. 2014).

(56) References Cited

OTHER PUBLICATIONS

Ishikawa et al. STING regulates intracellular DNA-mediated, type I interferon-dependent innate immunity, 461 Nature 788-792 (Oct. 8, 2009).
Jacobs et al. HSV-1 based vectors for gene therapy of neurological diseases and brain tumors Part II Vector Systems and Applications, 1(5) Neoplasia 402-416 (Nov. 1999).
Jacobs et al. Vaccinia Virus Vaccines: Past, Present and Future, 84(1) Antiviral Res. 1-13 (Oct. 2009).
John et al. Oncolytic Virus and Anti-4-IBB Combination Therapy Elicits Strong Antitumor Immunity against Established Cancer, 72(7) Cancer Research 1651-60 (Apr. 2012).
Kaufmann et al. Chemovirotherapy of Malignant Melanoma with a Targeted and Armed Oncolytic Measles Virus, 133 Journal of Investigative Dermatology 1034-42 (2013).
Kelly and Russell, History of Oncolytic Viruses: Genesis to Genetic Engineering, 15(4) Molecular Therapy 651-659 (Apr. 2007).
Kleinpeter et al. Vectorization in an oncolytic vaccinia virus of an antibody, a Fab and a scFv against programmed cell death-1 (PD-1) allows their intratumoral delivery and an improved tumor-growth inhibition, 5(10) Oncoimmunology e1220467 (2016).
Le Boeuf et al. Synergistic Interaction Between Oncolytic Viruses Augments Tumor Killing, 18(5) Molecular Therapy 888-895 (May 2010).
Lee et al. Enhanced Antitumor Effect of Oncolytic Adenovirus Expressing Interleukin-12 and B7-1in an Immunocompetent Murine Model, 12(19) Clin. Cancer Res. 5859-68 (Oct. 2006).
Ipson and Drake, Ipilimumab: An Anti-CTLA-4 Antibody for Metastatic Melanoma, 17(22) Clin. Cancer Res. 6958-62 (Nov. 2011).
List of known isolates within each virus family extracted from NCBI Taxonomy Browser Output of Ex. 1023, dtd Nov. 3, 2021.
Lundstrom, New frontiers in oncolytic viruses: optimizing and selecting for virus strains with improved efficacy, 12 Biologics: Targets and Therapy 43-60 (2018).
Ma et al. Oncolytic herpes simplex virus and immunotherapy, 19 BMC Immunology 40 (2018).
Majid et al. Recombinant Vesicular Stomatitis Virus (VSV) and Other Strategies in HCV Vaccine Designs and Immunotherapy. Tan SL, (Ed.) Hepatitis C Viruses: Genomes and Molecular Biology, Ch. 15. Norfolk (UK): Horizon Bioscience (2006).
Malhotra et al. Use of an Oncolytic Virus Secreting GM-CSF as Combined Oncolytic and Immunotherapy for Treatment of Colorectal and Hepatic Adenocarcinomas, 141(4) Surgery 520-529 (Apr. 2007).
McDonald et al. A measles virus vaccine strain derivative as a novel oncolytic agent against breast cancer, 99 Breast Cancer Research and Treatment 177-184 (2006).
Msaouel et al. Attenuated oncolytic Measles Virus strains as cancer therapeutics, 13(9) Curr. Pharm. Biotechnol. 1732-41 (Jul. 1, 2012).
Nakamori et al. Potent Antitumor Activity After Systemic Delivery of a Doubly Fusogenic Oncolytic Herpes Simplex Virus Against Metastatic Prostate Cancer, 60 The Prostate 53-60 (2004).
Fielding et al. "A hyperfusogenic gibbon apeleukemia envelope glycoprotein: targeting of a cytotoxic gene by ligand display", Hum Gene Ther. Apr. 10, 2000;11(6):817-26.
Oliveira et al. Poxvirus Host Range Genes and Virus-Host Spectrum: A Critical Review, 9(11) Viruses 2017 331 (Nov. 7, 2017).
Output from antibodies-online.com search for CTLA-4 Antibodies (performed Nov. 24, 2021), available at https://www.antibodies-online.com/search.php#5qk9.
Output from Antibodypedia search for CTLA-4 Antibodies (performed Nov. 24, 2021), available at https://www.antibodYPedia.eom/gene/I 9961/CTLA4.
Output from Biocompare search for CTLA-4 Antibodies (performed Nov. 24, 2021), available at https://www.biocompare.com/Search-Antibodies/?search=CTLA-4&said=0.
Output from the National Institutes of Health (NIH) National Center for Biotechnology Information (NCBI) Taxonomy Browser searches for "herpesviridae", "poxviridae", "adenovirdae", "retroviridae", "rhabdoviridae", "paramyxoviridae", and "reoviridae" (performed Nov. 3, 2021), available at: https://www.ncbi.nlm.nih.gov/Taxonomy/Browser/wwwtax.cgi7mode =Root.
Pentcheva-Hoang et al. B7-1 and B7-2 Selectively Recruit CTLA-4 and CD28 to the Immunological Synapse, 21 Immunity 401-413 (Sep. 2004).
Petition for Post-Grant Review of U.S. Pat. No. 10,947,513, filed Dec. 15, 2021 with the TTAB, Petitioner—Transgene and Bioinvent International AB.
Reoviridae Information from Virus Pathogen Resource (ViPR) retrieved on Nov. 4, 2021, available at https://www.viprbrc.org/brc/aboutPathogen.spg?decorator=reo.
Ribas, Clinical Development of the Anti-CTLA-4 Antibody Tremelimumab, 37(5) Seminars in Oncology 450-454 (Oct. 2010).
Riedel et al. Components and Architecture of the Rhabdovirus Ribonucleoprotein Complex, 12(9) Viruses 2020 959 (Aug. 2020).
Rojas et al. Defining Effective Combinations of Immune Checkpoint Blockade and Oncolytic Virotherapy, 21(24) Clin. Cancer Res. 5543-51 (Dec. 2015).
Saha et al. The Adenovirus Genome Contributes to the Structural Stability of the Virion, 6(9) Viruses 2014 3563-3583 (Sep. 24, 2014).
Salzberg, Open questions: How many genes do we have? 16 BMC Biology 94 (Aug. 20, 2018).
Sharp and Li, The codon adaptation index—a measure of directional synonymous codon usage bias, and its potential applications, 15(3) Nucleic Acids Research 1281-95 (1987).
Singh et al. Oncolytic viruses & their specific targeting to tumour cells, 136 Indian J. Med. Res. 571-584 (Oct. 2012).
Sinkovics and Horvath, Natural and genetically engineered viral agents for oncolysis and gene therapy of human cancers, 56 Arch. Immunol. Ther. Exp. 3-59 (2008).
Smith et al. Studies on the Use of Viruses in the Treatment of Carcinoma of the Cervix, 9(6) Cancer 1211-18 (Nov.-Dec. 1956).
Species list extracted from International Committee on Taxonomy of Viruses (ICTY) Master Species List (Jul. 20, 2021), available at: https://talk.ictvonline.org/taxonomy/vmr/.
Study Details for Clinical Trial NCT02272855 "A Study of Combination Treatment With HF10 and Ipilimumab in Patients With Unresectable or Metastatic Melanoma", last updated Sep. 26, 2018, available at: https://clinicaltrials.gov/ct2/show/NCT02272855.
Study Details for Clinical Trial NCT02620423 "Study of Pembrolizumab with REOLYSIN® and Chemotherapy in Patients With Advanced Pancreatic Adenocarcinoma", last updated Sep. 13, 2018, available at: https://clinicaltrials.gov/ct2/show/NCT02620423.
Summary of Characteristics of Commercial Viral Vectors from ThermoFisher Scientific, retrieved Nov. 4, 2021, available at https://www.thermofisher.com/us/en/home/references/gibco-cell-culture-basics/transfection-basics/gene-delivery-technologies/viral-delivery/viral-vectors.html.
Tan et al. Combination therapy of oncolytic herpes simplex virus HF10 and bevacizumab against experimental model of human breast carcinoma xenograft, 136 Int. J. Cancer 1718-30 (2015).
Tesfay et al. PEGylation of Vesicular Stomatitis Virus Extends Virus Persistence in Blood Circulation of Passively Immunized Mice, 87(7) Journal of Virology 3752-59 (Apr. 2013).
Van den Wollenberg et al. Replicating reoviruses with a transgene replacing the codons for the head domain of the viral spike, 22 Gene Therapy 267-279 (2015).
Wennier et al. Bugs and Drugs: Oncolytic Virotherapy in Combination with Chemotherapy, 13(9) Curr. Pharm. Biotechnol. 1817-33 (Jul. 2012).
Wertz et al. Adding genes to the RNA genome of vesicular stomatitis virus: positional effects on stability of expression, 76(15) J. Virol. 7642-50 (Aug. 2002).
Willemsen and Zwart, On the stability of sequences inserted into viral genomes, 5(2) Virus Evolution vez045 (Jul. 2019).
Yang et al. Cascade regulation of vaccinia virus gene expression is modulated by multistage promoters, 447(1-2) Virology 213-220 (Dec. 2013).
Yen et al. Vaccinia virus infection & temporal analysis of virus gene expression: Part 2, 2009(26) J. Vis. Exp. 1169 (Apr. 2009).
Ahlers et al: "A push-pull approach to maximize vaccine efficacy: abrogating suppression with an IL-13 inhibitor while augmenting

(56) References Cited

OTHER PUBLICATIONS help with granulocyte/macrophage colony-stimulating factor and CD40L", Proc Natl Acad Sci USA, Oct. 1, 2002;99(20):13020-5.
Assal et al: "Emerging targets in cancer immunotherapy: beyond CTLA-4 and PD-1", Immunotherapy. 2015;7 (11):1169-86.
Bauzon and Hermiston, 2014. Front. Immunol., 5(74): 1-10.
Capece et al: "Targeting costimulatory molecules to improve anti-tumor immunity", J Biomed Biotechnol, 2012; 2012:926321.
Choi et al., "Concurrent delivery of GM-CSF and B7-1 using an oncolytic adenovirus elicits potent antitumor effect", Gene Therapy (2006) 13, 1010-1020 & 2006 Nature Publishing Group.
Choi et al., "Strengthening of antitumor immune memory and prevention of thymic atrophy mediated by adenovirus expressing IL-12 and GM-CSF", Gene Therapy (2012) 19, 711-723 & 2012 Macmillan Publishers.
Dias et al., 2012. Gene Ther., 19: 988-998.
Hu et al. "A simplified system for generating oncolytic adenovirus vector carrying one or two transgenes", Cancer Gene Therapy (2008) 15, 173-182 r 2008 Nature Publishing Group.
Gao et al: "Recombinant vesicularm stomatitis virus targeted to Her2/neu combined with anti-CTLA4 antibody eliminates implanted mammary tumors", Cancer Gene Ther. Jan. 2009;16(1):44-52.
Gri et al: "X40 ligand-transduced tumor cell vaccine synergizes with GM-CSF and requires CD40-Apc signaling to boost the host T cell antitumor response", J Immunol. Jan. 1, 2003;170(1):99-106.
Hurwitz et al: "CTLA-4 blockade synergizes with tumor-derived granulocyte-macrophage colony-stimulating factor for treatment of an experimental mammary carcinoma", Proc Natl Acad Sci USA, Aug. 18, 1998;95(17):10067-71.
Kaufman et al: "Oncolytic viruses: a new class of immunotherapy drugs", Nat Rev Drug Discov, vol. 14, 642-662 (Sep. 2015).
Lee et al: "Oncolytic potential of E1B 55 kDa-deleted YKL-1 recombinant adenovirus: correlation with p53 functional status" Int J Cancer (2000) 88: 454-463.
Li, B et al: "Established B16 tumors are rejected following treatment with GM-CSF-secreting tumor cell immunotherapy In combination with anti-4-1 BB mAb", Clin Immunol. Oct. 2007;125(1):76-87.
Li, B et al: "Anti-programmed death-1 synergizes with granulocyte macrophage colony-stimulating factor-secreting tumor cell immunotherapy providing therapeutic benefit to mice with established tumors", Clin Cancer Res. Mar. 1, 2009;15(5):1623-34.
Murata et al: "X40 costimulation synergizes with GM-CSF whole-cell vaccination to overcome established CD8+ T cell tolerance to an endogenous tumor antigen", J Immunol. Jan. 15, 2006;176(2):974-83.
Sumimoto et al: "GM-CSF and B7-1 (CD80) co-stimulatory signals co-operate in the induction of effective anti-tumor Immunity in syngeneic mice", Int J Cancer. Nov. 14, 1997;73(4):556-61.
Yo, Y-T et al: "Coexpression of Flt3 ligand and GM-CSF genes modulates immune responses induced by HER2/neu DNA vaccine", Cancer Gene Ther. Nov. 2007;14(11):904-17.
EPO Opposition "Opponent's Response in opposition proceedings against Replimune's European Patent EP 3400291", provided by the European Patent Office on May 4, 2023.
Fonteneau et al., "Oncolytic immunotherapy: The new clinical outbreak", OncoImmunology, 2016, 5:1,e1066961.
Japanese Notice of Rejection mailed Feb. 28, 2023 during examination of related JP Patent Appl. No. 2019-537074.
Marcos et al., "Mapping of the RNA promoter of Newcastle disease virus", Virology, vol. 331, Issue 2, 2005, pp. 396-406.
Noton and Fearns, "Initiation and regulation of paramyxovirus transcription and replication", Virology, 2015, 479-480, 545-554.
Nobel Assembly at Karolinska Institutet; 2018 Nobel Prize in Physiology or Medicine; James P. Allison and Tasuku Honjo; Discovery of Cancer Therapy by Inhibition of Negative Immune Regulation; 2018.
Immune Checkpoint Signalling in the Tumor Environment; Cell Signaling Technology; Mar. 2018.

* cited by examiner

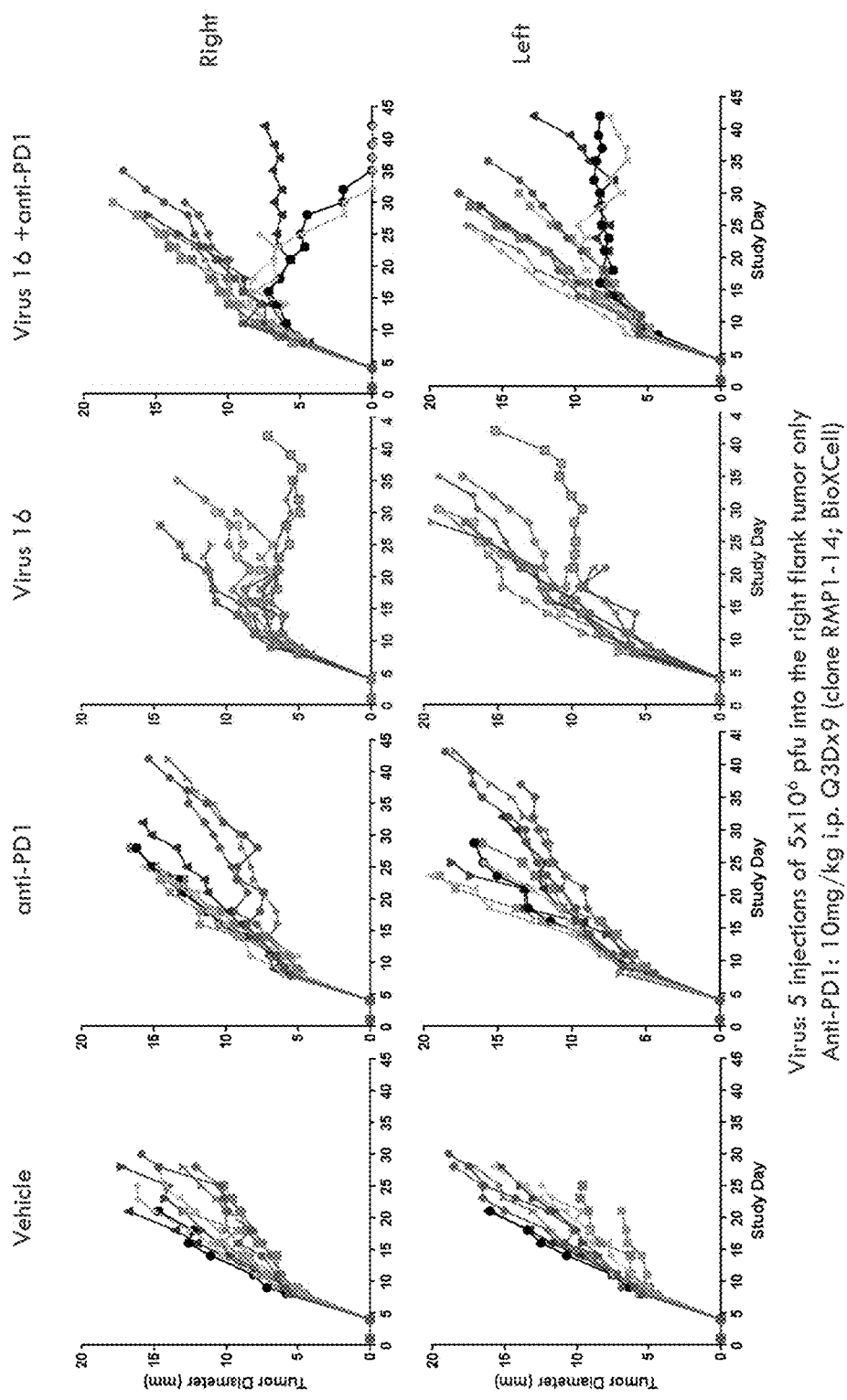

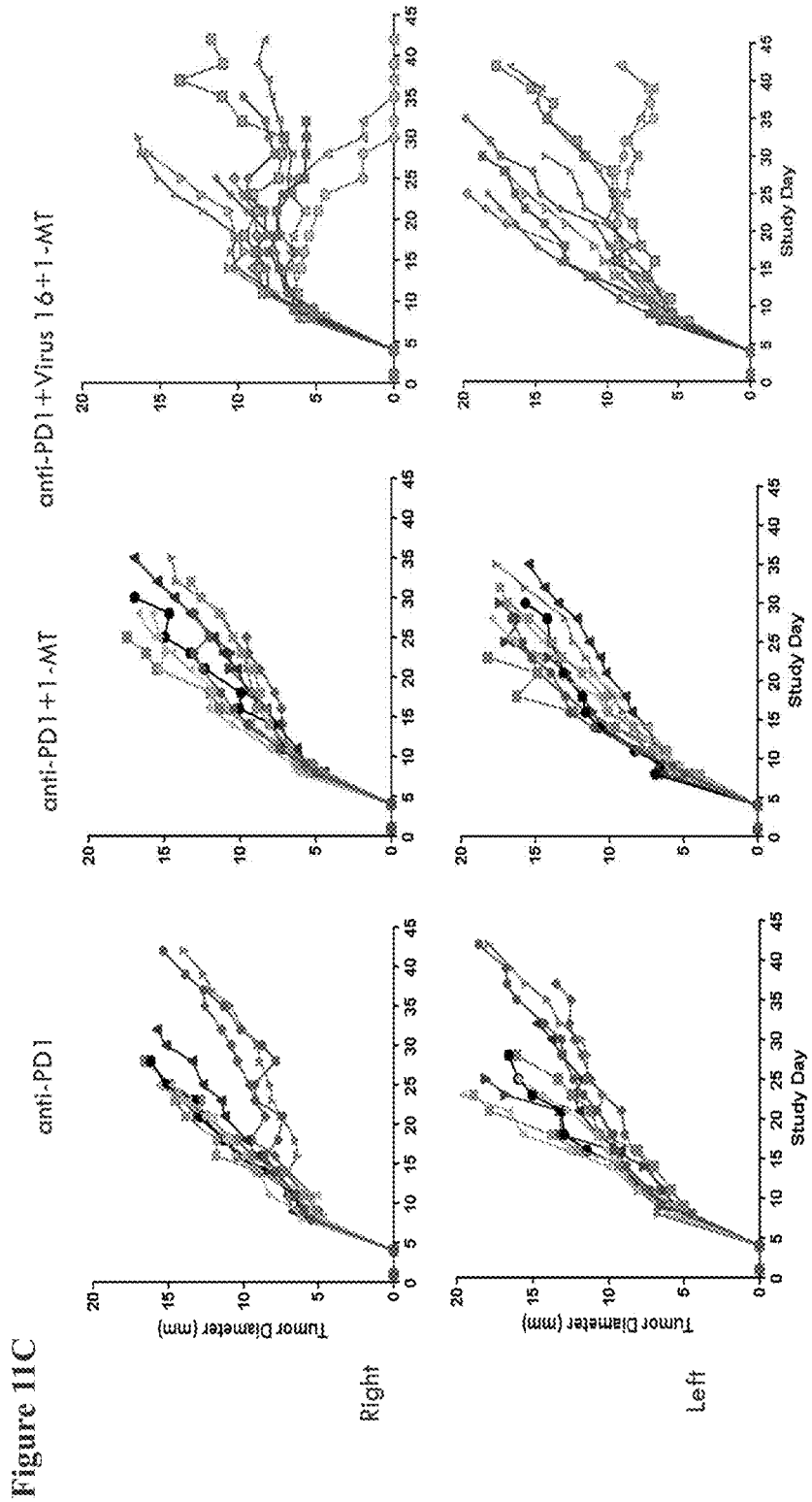

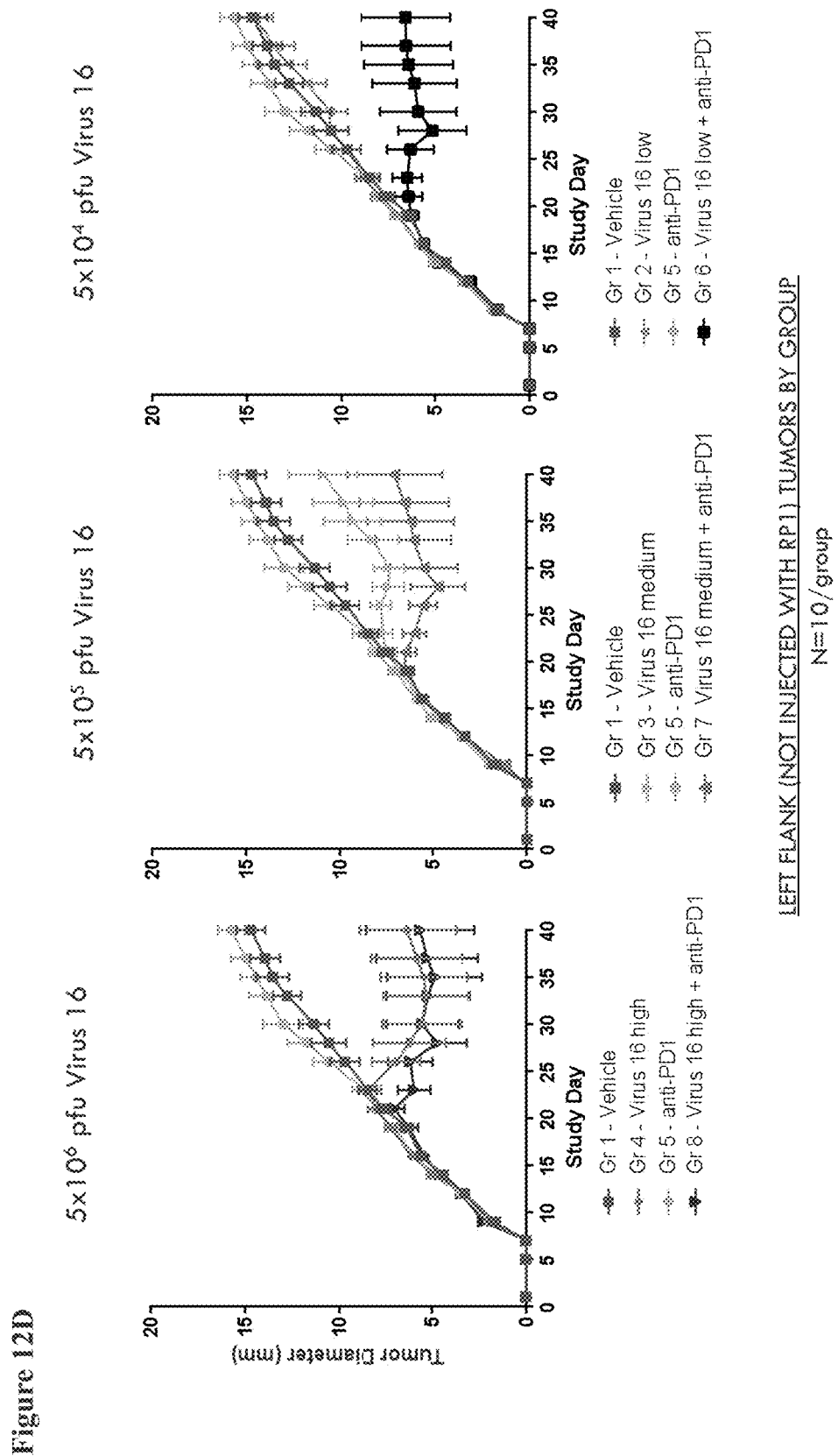

SEQUENCE LISTING

```
<160> NUMBER OF SEQ ID NOS: 45

<210> SEQ ID NO 1
<211> LENGTH: 426
<212> TYPE: DNA
<213> ORGANISM: Mus musculus

<400> SEQUENCE: 1
atgtggctgc agaatttact tttcctgggc attgtggtct acagcctctc agcacccacc     60
cgctcaccca tcactgtcac ccggccttgg aagcatgtag aggccatcaa agaagccctg    120
aacctcctgg atgacatgcc tgtcacattg aatgaagagg tagaagtcgt ctctaacgag    180
ttctccttca agaagctaac atgtgtgcag acccgcctga agatattcga gcagggtcta    240
cggggcaatt tcaccaaact caagggcgcc ttgaacatga cagccagcta ctaccagaca    300
tactgccccc caactccgga aacggactgt gaaacacaag ttaccaccta tgcggatttc    360
atagacagcc ttaaaacctt tctgactgat atcccctttg aatgcaaaaa accagtccaa    420
aaatga                                                               426

<210> SEQ ID NO 2
<211> LENGTH: 426
<212> TYPE: DNA
<213> ORGANISM: Mus musculus

<400> SEQUENCE: 2
atgtggctcc agaacctcct cttcctcggt atcgtcgtgt attcactctc cgcacctact     60
cgctcaccta tcactgtcac cagaccctgg aagcacgtgg aggccatcaa ggaggctctg    120
aacctgctgg acgatatgcc agtgaccctg aacgaggagg tggaggtggt gagcaacgag    180
ttctccttta agaagctgac ctgcgtgcag acaaggctga agatcttcga gcagggcctg    240
agaggaaact ttaccaagct gaagggcgcc ctgaacatga ccgcttctta ctaccagaca    300
tactgccccc ctacccccga gacagactgt gagacacagg tgaccacata cgccgacttc    360
attgatagcc tgaaaacatt cctgaccgac attccatttg agtgtaagaa gcccgtccag    420
aagtaa                                                               426

<210> SEQ ID NO 3
<211> LENGTH: 435
<212> TYPE: DNA
<213> ORGANISM: Homo sapiens

<400> SEQUENCE: 3
atgtggctgc agagcctgct gctcttgggc actgtggcct gcagcatctc tgcacccgcc     60
cgctcgccca gccccagcac gcagccctgg gagcatgtga atgccatcca ggaggcccgg    120
cgtctcctga acctgagtag agacactgct gctgagatga atgaaacagt agaagtcatc    180
tcagaaatgt ttgacctcca ggagccgacc tgcctacaga cccgcctgga gctgtacaag    240
cagggcctgc ggggcagcct caccaagctc aagggcccct tgaccatgat ggccagccac    300
```

```
tacaagcagc actgccctcc aaccccggaa acttcctgtg caacccagat tatcaccttt      360
gaaagtttca aagagaacct gaaggacttt ctgcttgtca tcccctttga ctgctgggag      420
ccagtccagg agtga                                                      435
```

```
<210> SEQ ID NO 4
<211> LENGTH: 435
<212> TYPE: DNA
<213> ORGANISM: Homo sapiens

<400> SEQUENCE: 4
atgtggctgc agtccctgct gctgctgggc accgtcgcct gttctatttc cgcacccgca       60
aggtcaccaa gtccatctac tcagccttgg gagcacgtga acgcaatcca ggaggcacgg      120
cggctgctga acctgagccg ggacaccgcc gccgagatga acgagacagt ggaagtgatc      180
agcgagatgt tcgatctgca ggagcccacc tgcctgcaga aaggctggag gctgtacaag      240
cagggcctgc gcggctctct gaccaagctg aagggcccac tgacaatgat ggccagccac      300
tataagcagc actgcccccc taccccgag acaagctgtg ccacccagat catcacattc      360 gagtcccttta aggagaacct gaaggatttt ctgctggtca ttccatttga ttgttgggag      420
cccgtccagg agtaa                                                      435
```

```
<210> SEQ ID NO 5
<211> LENGTH: 141
<212> TYPE: PRT
<213> ORGANISM: Mus musculus

<400> SEQUENCE: 5

Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
        35                  40                  45

Thr Leu Asn Glu Glu Val Glu Val Val Ser Asn Glu Phe Ser Phe Lys
    50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Val Gln Lys
    130                 135                 140
```

```
<210> SEQ ID NO 6
<211> LENGTH: 144
<212> TYPE: PRT
<213> ORGANISM: Homo sapiens

<400> SEQUENCE: 6

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30
```

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
 50                  55                  60

Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                    85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
                115                 120                 125

Asp Phe Leu Leu Val Ile Pro Phe Asp Cys Trp Glu Pro Val Gln Glu
130                 135                 140

<210> SEQ ID NO 7
<211> LENGTH: 2010
<212> TYPE: DNA
<213> ORGANISM: Gibbon leukemia virus

<400> SEQUENCE: 7

```
atggtattgc tgcctgggtc catgcttctc acctcaaacc tgcaccacct tcggcaccag      60
atgagtcctg ggagctggaa aagactgatc atcctcttaa gctgcgtatt cggcggcggc     120
gggacgagtc tgcaaaataa gaaccccac cagcccatga ccctcacttg caggtactg      180
tcccaaactg gagacgttgt ctgggataca aaggcagtcc agccccttg acttggtgg      240
cccacactta aacctgatgt atgtgccttg gcggctagtc ttgagtcctg ggatatcccg     300
ggaaccgatg tctcgtcctc taaacgagtc agacctccgg actcagacta tactgccgct     360
tataagcaaa tcacctgggg agccataggg tgcagctacc ctcgggctag gactagaatg     420
gcaagctcta ccttctacgt atgtcccgg gatggccgga cccttcaga agctagaagg      480
tgcggggggc tagaatccct atactgtaaa gaatgggatt gtgagaccac ggggaccggt     540
tattggctat ctaaatcctc aaagaccctc ataactgtaa aatgggacca aaatagcgaa     600
tggactcaaa aatttcaaca gtgtcaccag accggctggt gtaacccct aaaatagat      660
ttcacagaca aaggaaaatt atccaaggac tggataacgg gaaaaacctg gggattaaga     720
ttctatgtgt ctggacatcc aggcgtacag ttcaccattc gcttaaaaat caccaacatg     780
ccagctgtgg cagtaggtcc tgacctcgtc cttgtggaac aaggacctcc tagaacgtcc     840
ctcgctctcc cacctcctct tccccaagg gaagcgccac cgccatctct ccccgactct     900
aactccacag ccctggcgac tagtgcacaa actcccacgg tgagaaaaac aattgttacc     960
ctaaacactc cgcctcccac cacaggcgac agacttttg atcttgtgca ggggccttc    1020
ctaaccttaa atgctaccaa cccaggggcc actgagtctt gctggctttg tttggccatg    1080
ggccccctt attatgaagc aatagcctca tcaggagagg tcgcctactc caccgacctt    1140
gaccggtgcc gctggggga ccaaggaaag ctcacccctc ctgaggtctc aggacacggg    1200
ttgtgcatag aaaggtgcc cttatccccat cagcatctct gcaatcagac cctatccatc    1260
aattcctccg gagaccatca gtatctgctc ccctccaacc atagctggtg ggcttgcagc    1320
actggcctca ccccttgcct ctccacctca gtttttaatc agactagaga tttctgtatc    1380
caggtccagc tgattcctcg catctattac tatcctgaag aagttttgtt acaggcctat    1440
gacaattctc accccaggac taaaagagag gctgtctcac ttaccctagc tgttttactg    1500
```

```
gggttgggaa tcacggcggg aataggtact ggttcaactg ccttaattaa aggacctata    1560
gacctccagc aaggcctgac aagcctccag atcgccatag atgctgacct ccgggccctc    1620
caagactcag tcagcaagtt agaggactca ctgacttccc tgtccgaggt agtgctccaa    1680
aataggagag gccttgactt gctgtttcta aagaaggtg gcctctgtgc ggccctaaag     1740
gaagagtgct gttttacat agaccactca ggtgcagtac gggactccat gaaaaaactc    1800
aaagaaaaac tggataaaag acagttagag cgccagaaaa gccaaaactg gtatgaagga    1860
tggttcaata actcccccttg gttcactacc ctgctatcaa ccatcgctgg gccctatta    1920 ctcctccttc tgttgctcat cctcgggcca tgcatcatca taagttagt tcaattcatc     1980 aatgatagga taagtgcagt taaaatttaa                                    2010
```

<210> SEQ ID NO 8
<211> LENGTH: 2013
<212> TYPE: DNA
<213> ORGANISM: Gibbon leukemia virus

<400> SEQUENCE: 8

```
accatggtcc tgctgcctgg gtctatgctg ctgacttcta acctgcacca cctgcgacac     60
cagatgtctc ccggctcatg gaaacggctg atcatcctgc tgagctgcgt gttcggagga   120
ggaggcacct ccctgcagaa caagaatcct caccagccaa tgaccctgac atggcaggtg   180
ctgtcccaga caggcgacgt ggtgtgggat accaaggcag tgcagccacc ttggacatgg   240
tggcccaccc tgaagcctga cgtgtgcgcc ctggccgcct ccctggagtc ttgggacatc   300
cccggcacag acgtgagcag cagcaagagg gtgagaccac ccgactctga ttatacagcc   360
gcctacaagc agatcacctg gggcgccatc ggctgtagct atcctcgggc cgcacaagg   420 atggccagct ccaccttta cgtgtgccca cgcgacggaa ggaccctgtc tgaggcaagg   480
agatgtggcg gcctggagag cctgtattgc aaggagtggg attgtgagac cacaggcaca   540
ggctactggc tgtctaagtc tagcaaggac ctgatcaccg tgaagtggga tcagaacagc   600
gagtggacac agaagttcca gcagtgccac cagaccggct ggtgtaatcc cctgaagatc   660
gactttacag ataagggcaa gctgtccaag gactggatca ccggcaagac atggggcctg   720
agattctacg tgtctggcca ccctggcgtg cagtttacaa tccggctgaa gatcaccaac   780
atgccagcag tggcagtggg accagacctg gtgctggtgg agcagggacc tccacgcacc   840
tccctggccc tgccccctcc actgccccct agggaggccc cacccctag cctgcccgat    900 tctaacagca cagccctggc cacctccgcc cagaccccta cagtgcgcaa gaccatcgtg   960
acactgaata ccccaccccc taccacaggc gacaggctgt tcgatctggt gcagggcgcc   1020
tttctgacac tgaacgccac caatcctggc gcaaccgaga ctgctggct gtgcctggct   1080 atgggcccac cctactatga ggcaatcgcc tcctctggag aggtggcata ttccacagac   1140
ctggatagat gcagatgggg cacccagggc aagctgaccc tgacagaggt gtctggccac   1200
ggcctgtgca tcggcaaggt gccattcaca caccagcacc tgtgcaacca gaccctgagc   1260
atcaatagct ccggcgacca ccagtacctg ctgccaagca ccactcctg gtgggcatgc   1320 tccacaggac tgacccatg tctgagcacc agcgtgttca accagaccag agacttttgt   1380
atccaggtgc agctgatccc tcggatctac tattacccag aggaggtgct gctgcaggcc   1440
tatgataatt cccacccaag aacaaagagg gaggccgtgt ctctgaccct ggccgtgctg   1500
ctgggactgg gaatcacagc aggaatcggc acaggcagca ccgccctgat caagggacca   1560
```

| | | | | |
|---|---|---|---|---|
| atcgacctgc agcagggact gacctccctg cagatcgcca tcgacgccga tctgagagcc | 1620 |
| ctgcaggaca gcgtgtccaa gctggaggat tctctgacct ctctgagcga ggtggtgctg | 1680 |
| cagaacagga ggggcctgga cctgctgttc ctgaaggagg aggactgtg cgccgccctg | 1740 |
| aaggaggagt gctgttttta tatcgaccac tctggcgccg tgcgggatag catgaagaag | 1800 |
| ctgaaggaga agctggataa cgccagctg gagaggcaga agagccagaa ttggtacgag | 1860 |
| ggctggttca acaattcccc ctggtttacc acactgctgt ctaccatcgc aggacctctg | 1920 |
| ttattactgc tgctgctgct gatcctgggc ccatgtatca tcaacaagct ggtgcagttt | 1980 |
| atcaacgacc gaatctccgc agtgaaaatc taa | 2013 |

<210> SEQ ID NO 9
<211> LENGTH: 669
<212> TYPE: PRT
<213> ORGANISM: Gibbon leukemia virus

<400> SEQUENCE: 9

```
Met Val Leu Leu Pro Gly Ser Met Leu Leu Thr Ser Asn Leu His His
1               5                   10                  15

Leu Arg His Gln Met Ser Pro Gly Ser Trp Lys Arg Leu Ile Ile Leu
            20                  25                  30

Leu Ser Cys Val Phe Gly Gly Gly Thr Ser Leu Gln Asn Lys Asn
        35                  40                  45

Pro His Gln Pro Met Thr Leu Thr Trp Gln Val Leu Ser Gln Thr Gly
    50                  55                  60

Asp Val Val Trp Asp Thr Lys Ala Val Gln Pro Pro Trp Thr Trp Trp
65                  70                  75                  80

Pro Thr Leu Lys Pro Asp Val Cys Ala Leu Ala Ala Ser Leu Glu Ser
                85                  90                  95

Trp Asp Ile Pro Gly Thr Asp Val Ser Ser Lys Arg Val Arg Pro
            100                 105                 110

Pro Asp Ser Asp Tyr Thr Ala Ala Tyr Lys Gln Ile Thr Trp Gly Ala
        115                 120                 125

Ile Gly Cys Ser Tyr Pro Arg Ala Arg Thr Arg Met Ala Ser Ser Thr
    130                 135                 140

Phe Tyr Val Cys Pro Arg Asp Gly Arg Thr Leu Ser Glu Ala Arg Arg
145                 150                 155                 160

Cys Gly Gly Leu Glu Ser Leu Tyr Cys Lys Glu Trp Asp Cys Glu Thr
                165                 170                 175

Thr Gly Thr Gly Tyr Trp Leu Ser Lys Ser Ser Lys Asp Leu Ile Thr
            180                 185                 190

Val Lys Trp Asp Gln Asn Ser Glu Trp Thr Gln Lys Phe Gln Gln Cys
        195                 200                 205

His Gln Thr Gly Trp Cys Asn Pro Leu Lys Ile Asp Phe Thr Asp Lys
    210                 215                 220

Gly Lys Leu Ser Lys Asp Trp Ile Thr Gly Lys Thr Trp Gly Leu Arg
225                 230                 235                 240

Phe Tyr Val Ser Gly His Pro Gly Val Gln Phe Thr Ile Arg Leu Lys
                245                 250                 255

Ile Thr Asn Met Pro Ala Val Ala Val Gly Pro Asp Leu Val Leu Val
            260                 265                 270

Glu Gln Gly Pro Pro Arg Thr Ser Leu Ala Leu Pro Pro Pro Leu Pro
        275                 280                 285

Pro Arg Glu Ala Pro Pro Pro Ser Leu Pro Asp Ser Asn Ser Thr Ala
```

```
                   290                 295                 300
Leu Ala Thr Ser Ala Gln Thr Pro Thr Val Arg Lys Thr Ile Val Thr
305                 310                 315                 320

Leu Asn Thr Pro Pro Thr Thr Gly Asp Arg Leu Phe Asp Leu Val
                325                 330                 335

Gln Gly Ala Phe Leu Thr Leu Asn Ala Thr Asn Pro Gly Ala Thr Glu
                340                 345                 350

Ser Cys Trp Leu Cys Leu Ala Met Gly Pro Pro Tyr Tyr Glu Ala Ile
            355                 360                 365

Ala Ser Ser Gly Glu Val Ala Tyr Ser Thr Asp Leu Asp Arg Cys Arg
        370                 375                 380

Trp Gly Thr Gln Gly Lys Leu Thr Leu Thr Glu Val Ser Gly His Gly
385                 390                 395                 400

Leu Cys Ile Gly Lys Val Pro Phe Thr His Gln His Leu Cys Asn Gln
                405                 410                 415

Thr Leu Ser Ile Asn Ser Ser Gly Asp His Gln Tyr Leu Leu Pro Ser
                420                 425                 430

Asn His Ser Trp Trp Ala Cys Ser Thr Gly Leu Thr Pro Cys Leu Ser
435                 440                 445

Thr Ser Val Phe Asn Gln Thr Arg Asp Phe Cys Ile Gln Val Gln Leu
        450                 455                 460

Ile Pro Arg Ile Tyr Tyr Tyr Pro Glu Glu Val Leu Leu Gln Ala Tyr
465                 470                 475                 480

Asp Asn Ser His Pro Arg Thr Lys Arg Glu Ala Val Ser Leu Thr Leu
                485                 490                 495

Ala Val Leu Leu Gly Leu Gly Ile Thr Ala Gly Ile Gly Thr Gly Ser
                500                 505                 510

Thr Ala Leu Ile Lys Gly Pro Ile Asp Leu Gln Gln Gly Leu Thr Ser
            515                 520                 525

Leu Gln Ile Ala Ile Asp Ala Asp Leu Arg Ala Leu Gln Asp Ser Val
        530                 535                 540

Ser Lys Leu Glu Asp Ser Leu Thr Ser Leu Ser Glu Val Val Leu Gln
545                 550                 555                 560

Asn Arg Arg Gly Leu Asp Leu Phe Leu Lys Glu Gly Gly Leu Cys
                565                 570                 575

Ala Ala Leu Lys Glu Glu Cys Cys Phe Tyr Ile Asp His Ser Gly Ala
                580                 585                 590

Val Arg Asp Ser Met Lys Lys Leu Lys Glu Lys Leu Asp Lys Arg Gln
            595                 600                 605

Leu Glu Arg Gln Lys Ser Gln Asn Trp Tyr Glu Gly Trp Phe Asn Asn
        610                 615                 620

Ser Pro Trp Phe Thr Thr Leu Leu Ser Thr Ile Ala Gly Pro Leu Leu
625                 630                 635                 640

Leu Leu Leu Leu Leu Leu Ile Leu Gly Pro Cys Ile Ile Asn Lys Leu
                645                 650                 655

Val Gln Phe Ile Asn Asp Arg Ile Ser Ala Val Lys Ile
                660                 665
```

<210> SEQ ID NO 10
<211> LENGTH: 759
<212> TYPE: DNA
<213> ORGANISM: Artificial Sequence
<220> FEATURE:
<223> OTHER INFORMATION: Homo sapiens

<400> SEQUENCE: 10

```
atgatcgaga cctacaatca gacaagccca cggtccgccg caaccggact gcctatcagc      60
atgaagatct tcatgtacct gctgaccgtg tttctgatca cacagatgat cggctccgcc     120
ctgttcgccg tgtatctgca caggagactg gacaagatcg aggatgagcg caatctgcac     180
gaggacttcg tgtttatgaa gaccatccag cggtgcaaca caggcgagag gagcctgtct     240
ctgctgaatt gtgaggagat caagtcccag ttcgagggct tgtgtaagga tatcatgctg     300
aacaaggagg agacaaagaa ggacgaggat ccacagatcg cagcacacgt ggtgtccgag     360
gcaaactcta atgccgccag cgtgctgcag tgggccaaga agggctacta ccatgaag      420
tctaacctgg tgacactgga aatggcaag cagctgaccg tgaagaggca gggcctgtac     480
tatatctatg cccaggtgac attctgctct aacagagagg caagctccca ggcacccttc     540
atcgtgggac tgtggctgaa gccctctagc ggcagcgaga ggatcctgct gaaggccgcc     600
aatacccact cctctagcca gctgtgcgag cagcagtcca tccacctggg aggcgtgttc     660
gagctgcagc ctggagccag cgtgttcgtg aacgtgacac acccatctca ggtgagccac     720
ggcaccggct tcacaagctt tggcctgctg aagctgtga                            759
```

<210> SEQ ID NO 11
<211> LENGTH: 252
<212> TYPE: PRT
<213> ORGANISM: Artificial Sequence
<220> FEATURE:
<223> OTHER INFORMATION: Homo sapiens

<400> SEQUENCE: 11

```
Met Ile Glu Thr Tyr Asn Gln Thr Ser Pro Arg Ser Ala Ala Thr Gly
  1               5                  10                  15

Leu Pro Ile Ser Met Lys Ile Phe Met Tyr Leu Leu Thr Val Phe Leu
             20                  25                  30

Ile Thr Gln Met Ile Gly Ser Ala Leu Phe Ala Val Tyr Leu His Arg
         35                  40                  45

Arg Leu Asp Lys Ile Glu Asp Glu Arg Asn Leu His Glu Asp Phe Val
     50                  55                  60

Phe Met Lys Thr Ile Gln Arg Cys Asn Thr Gly Glu Arg Ser Leu Ser
 65                  70                  75                  80

Leu Leu Asn Cys Glu Glu Ile Lys Ser Gln Phe Glu Gly Phe Val Lys
                 85                  90                  95

Asp Ile Met Leu Asn Lys Glu Glu Thr Lys Lys Asp Glu Asp Pro Gln
            100                 105                 110

Ile Ala Ala His Val Val Ser Glu Ala Asn Ser Asn Ala Ala Ser Val
        115                 120                 125

Leu Gln Trp Ala Lys Lys Gly Tyr Tyr Thr Met Lys Ser Asn Leu Val
    130                 135                 140

Thr Leu Glu Asn Gly Lys Gln Leu Thr Val Lys Arg Gln Gly Leu Tyr
145                 150                 155                 160

Tyr Ile Tyr Ala Gln Val Thr Phe Cys Ser Asn Arg Glu Ala Ser Ser
                165                 170                 175

Gln Ala Pro Phe Ile Val Gly Leu Trp Leu Lys Pro Ser Ser Gly Ser
            180                 185                 190

Glu Arg Ile Leu Leu Lys Ala Ala Asn Thr His Ser Ser Ser Gln Leu
        195                 200                 205

Cys Glu Gln Gln Ser Ile His Leu Gly Gly Val Phe Glu Leu Gln Pro
    210                 215                 220
```

Gly Ala Ser Val Phe Val Asn Val Thr Asp Pro Ser Gln Val Ser His
225                 230                 235                 240

Gly Thr Gly Phe Thr Ser Phe Gly Leu Leu Lys Leu
                245                 250

<210> SEQ ID NO 12
<211> LENGTH: 1416
<212> TYPE: DNA
<213> ORGANISM: Homo sapiens

<400> SEQUENCE: 12

| | | | | | |
|---|---|---|---|---|---|
| atgctgccct | ttctgagcat | gctggtgctg | ctggtgcagc | ctctgggaaa | cctgggagcc | 60 |
| gagatgaaga | gcctgtccca | gagatctgtg | cctaacacct | gcacactggt | catgtgcagc | 120 |
| cccaccgaga | atggactgcc | tggaagggac | ggaagggatg | aagggagggg | ccctcggggc | 180 |
| gagaagggcg | acccaggact | gcctggacca | atgggactga | gcggactgca | gggaccaaca | 240 |
| ggacctgtgg | gaccaaaggg | agagaacgga | tccgccggag | agccaggccc | taagggcgag | 300 |
| aggggcctgt | ctggcccccc | tggcctgcca | ggcatcccag | ccccgccgg | caaggagggc | 360 |
| ccatccggca | gcagggcaa | tatcggcccc | cagggcaagc | ctggcccaaa | gggcgaggca | 420 |
| ggaccaaagg | gagaagtggg | agcacctggc | atgcagggat | ccaccggagc | aaagggatct | 480 |
| acaggaccaa | agggcgagcg | cggcgcccca | ggcgtgcagg | gcgcccccgg | caatgcagga | 540 |
| gcagcaggac | cagcaggacc | tgcaggccca | cagggcgccc | ctggctctag | ggcccacccc | 600 |
| ggcctgaagg | gcgacagggg | agtgcctggc | gatagggggca | tcaagggaga | gagcggactg | 660 |
| ccagattccg | ccgccctgag | gcagcagatg | gaggccctga | agggcaagct | gcagaggctg | 720 |
| gaggtggcct | tctcccacta | ccagaaggcc | gccctgtttc | cagacggcca | caggagactg | 780 |
| gacaagatcg | aggatgagcg | caacctgcac | gaggatttcg | tgtttatgaa | gaccatccag | 840 |
| agatgcaaca | caggcgagcg | gtctctgagc | ctgctgaatt | gtgaggagat | caagtctcag | 900 |
| ttcgagggct | ttgtgaagga | catcatgctg | aacaaggagg | agaccaagaa | ggagaatagc | 960 |
| ttcgagatgc | agaagggcga | tcagaatccc | cagatcgcag | cacacgtgat | cagcgaggca | 1020 |
| agctccaaga | ccacatccgt | gctgcagtgg | gccgagaagg | gctactatac | catgtccaac | 1080 |
| aatctggtga | cactggagaa | cggcaagcag | ctgaccgtga | agagacaggg | cctgtactat | 1140 |
| atctatgccc | aggtgacatt | ctgctctaat | cgggaggcct | ctagccaggc | ccctttttatc | 1200 |
| gcctctctgt | gcctgaagag | cccaggcaga | ttcgagcgga | tcctgctgag | ggccgccaac | 1260 |
| acccactcct | ctgccaagcc | atgcggacag | cagagcatcc | acctgggagg | cgtgttcgag | 1320 |
| ctgcagccag | gagcctccgt | gtttgtgaat | gtgacagacc | catcccaggt | gtctcacgga | 1380 |
| accggcttca | catcctttgg | cctgctgaag | ctgtga | | | 1416 |

<210> SEQ ID NO 13
<211> LENGTH: 471
<212> TYPE: PRT
<213> ORGANISM: Homo sapiens

<400> SEQUENCE: 13

Met Leu Pro Phe Leu Ser Met Leu Val Leu Val Gln Pro Leu Gly
1               5                   10                  15

Asn Leu Gly Ala Glu Met Lys Ser Leu Ser Gln Arg Ser Val Pro Asn
                20                  25                  30

Thr Cys Thr Leu Val Met Cys Ser Pro Thr Glu Asn Gly Leu Pro Gly
            35                  40                  45

-continued

Arg Asp Gly Arg Asp Gly Arg Glu Gly Pro Arg Gly Glu Lys Gly Asp
 50                  55                  60

Pro Gly Leu Pro Gly Pro Met Gly Leu Ser Gly Leu Gln Gly Pro Thr
65                  70                  75                  80

Gly Pro Val Gly Pro Lys Gly Glu Asn Gly Ser Ala Gly Glu Pro Gly
                85                  90                  95

Pro Lys Gly Glu Arg Gly Leu Ser Gly Pro Gly Leu Pro Gly Ile
            100                 105                 110

Pro Gly Pro Ala Gly Lys Glu Gly Pro Ser Gly Lys Gln Gly Asn Ile
        115                 120                 125

Gly Pro Gln Gly Lys Pro Gly Pro Lys Gly Glu Ala Gly Pro Lys Gly
    130                 135                 140

Glu Val Gly Ala Pro Gly Met Gln Gly Ser Thr Gly Ala Lys Gly Ser
145                 150                 155                 160

Thr Gly Pro Lys Gly Glu Arg Gly Ala Pro Gly Val Gln Gly Ala Pro
                165                 170                 175

Gly Asn Ala Gly Ala Ala Gly Pro Ala Gly Pro Ala Gly Pro Gln Gly
            180                 185                 190

Ala Pro Gly Ser Arg Gly Pro Pro Gly Leu Lys Gly Asp Arg Gly Val
        195                 200                 205

Pro Gly Asp Arg Gly Ile Lys Gly Glu Ser Gly Leu Pro Asp Ser Ala
    210                 215                 220

Ala Leu Arg Gln Gln Met Glu Ala Leu Lys Gly Lys Leu Gln Arg Leu
225                 230                 235                 240

Glu Val Ala Phe Ser His Tyr Gln Lys Ala Ala Leu Phe Pro Asp Gly
                245                 250                 255

His Arg Arg Leu Asp Lys Ile Glu Asp Glu Arg Asn Leu His Glu Asp
            260                 265                 270

Phe Val Phe Met Lys Thr Ile Gln Arg Cys Asn Thr Gly Glu Arg Ser
        275                 280                 285

Leu Ser Leu Leu Asn Cys Glu Glu Ile Lys Ser Gln Phe Glu Gly Phe
    290                 295                 300

Val Lys Asp Ile Met Leu Asn Lys Glu Glu Thr Lys Lys Glu Asn Ser
305                 310                 315                 320

Phe Glu Met Gln Lys Gly Asp Gln Asn Pro Gln Ile Ala Ala His Val
                325                 330                 335

Ile Ser Glu Ala Ser Ser Lys Thr Thr Ser Val Leu Gln Trp Ala Glu
            340                 345                 350

Lys Gly Tyr Tyr Thr Met Ser Asn Asn Leu Val Thr Leu Glu Asn Gly
        355                 360                 365

Lys Gln Leu Thr Val Lys Arg Gln Gly Leu Tyr Tyr Ile Tyr Ala Gln
    370                 375                 380

Val Thr Phe Cys Ser Asn Arg Glu Ala Ser Ser Gln Ala Pro Phe Ile
385                 390                 395                 400

Ala Ser Leu Cys Leu Lys Ser Pro Gly Arg Phe Glu Arg Ile Leu Leu
                405                 410                 415

Arg Ala Ala Asn Thr His Ser Ser Ala Lys Pro Cys Gly Gln Gln Ser
            420                 425                 430

Ile His Leu Gly Gly Val Phe Glu Leu Gln Pro Gly Ala Ser Val Phe
        435                 440                 445

Val Asn Val Thr Asp Pro Ser Gln Val Ser His Gly Thr Gly Phe Thr
    450                 455                 460

Ser Phe Gly Leu Leu Lys Leu
465                 470

<210> SEQ ID NO 14
<211> LENGTH: 1412
<212> TYPE: DNA
<213> ORGANISM: Mus musculus

<400> SEQUENCE: 14

| | | | | | |
|---|---|---|---|---|---|
| atgctgccct | tcctgagcat | gctggtgctg | ctggtgcagc | tctgggcaa | tctgggcgcc | 60 |
| gagatgaagt | ccctgtctca | gaggagcgtg | ccaaacacct | gcacactggt | catgtgctct | 120 |
| ccaaccgaga | atggactgcc | aggaagggac | ggaagagatg | gaagggaggg | accaagggga | 180 |
| gagaagggcg | accctggact | gcctggacca | atgggactgt | ccggactgca | gggaccaaca | 240 |
| ggccctgtgg | gaccaaaggg | agagaatgga | agcgccggag | agccaggacc | taagggagag | 300 |
| aggggcctgt | ccggcccccc | tggcctgcct | ggcatcccag | ccccgccgg | caaggagggc | 360 |
| ccttctggca | gcagggcaa | catcggacca | cagggcaagc | ctggaccaaa | gggagaggca | 420 |
| ggaccaaagg | gagaagtggg | agcacccggc | atgcagggca | gcaccggagc | aaagggatcc | 480 |
| accggcccta | agggagagag | aggagcacct | ggagtcagg | gcgcccagg | caatgcagga | 540 |
| gcagcaggac | cagcaggacc | tgcaggccca | cagggcgccc | caggcagccg | ggcccaccc | 600 |
| ggcctgaagg | gcgacagggg | agtgccaggc | gataggggca | tcaagggaga | gtccggactg | 660 |
| ccagactctg | ccgccctgag | gcagcagatg | gaggccctga | agggcaagct | gcagaggctg | 720 |
| gaggtggcct | tctcccacta | ccagaaggcc | gccctgtttc | cagacggaca | caggagactg | 780 |
| gataaggtgg | aggaggaggt | gaacctgcac | gaggatttcg | tgttcatcaa | gaagctgaag | 840 |
| aggtgcaaca | agggcgaggg | cagcctgtcc | ctgctgaatt | gtgaggagat | gcggcgccag | 900 |
| ttcgaggacc | tggtgaagga | tatcaccctg | aacaaggagg | agaagaagga | gaattctttt | 960 |
| gagatgcaga | gggcgacga | ggatcctcag | atcgcagcac | acgtggtgtc | gaggcaaac | 1020 |
| tctaatgccg | ccagcgtgct | gcagtgggcc | aagaagggct | actataccat | gaagtctaac | 1080 |
| ctggtcatgc | tggagaatgg | caagcagctg | acagtgaaga | gagagggcct | gtactacgtg | 1140 |
| tacacccagg | tgacattctg | cagcaacaga | gagcccagct | cccagcggcc | ttttatcgtg | 1200 |
| ggcctgtggc | tgaagccctc | tatcggaagc | gagaggatcc | tgctgaaggc | agccaatacc | 1260 |
| cactctagct | cccagctgtg | cgagcagcag | tccgtgcacc | tgggaggcgt | gttcgagctg | 1320 |
| caggcaggag | caagcgtgtt | cgtgaacgga | cagaggccag | ccaggtcatc | cacagagtgg | 1380 |
| gcttctctag | ctttggcctg | ctgaagctgt | ga | | | 1412 |

<210> SEQ ID NO 15
<211> LENGTH: 470
<212> TYPE: PRT
<213> ORGANISM: Mus musculus

<400> SEQUENCE: 15

Met Leu Pro Phe Leu Ser Met Leu Val Leu Val Gln Pro Leu Gly
1               5                   10                  15

Asn Leu Gly Ala Glu Met Lys Ser Leu Ser Gln Arg Ser Val Pro Asn
            20                  25                  30

Thr Cys Thr Leu Val Met Cys Ser Pro Thr Glu Asn Gly Leu Pro Gly
        35                  40                  45

Arg Asp Gly Arg Asp Gly Arg Glu Gly Pro Arg Gly Glu Lys Gly Asp
    50                  55                  60

```
Pro Gly Leu Pro Gly Pro Met Gly Leu Ser Gly Leu Gln Gly Pro Thr
 65                  70                  75                  80

Gly Pro Val Gly Pro Lys Gly Glu Asn Gly Ser Ala Gly Glu Pro Gly
                 85                  90                  95

Pro Lys Gly Glu Arg Gly Leu Ser Gly Pro Gly Leu Pro Gly Ile
            100                 105                 110

Pro Gly Pro Ala Gly Lys Glu Gly Pro Ser Gly Lys Gln Gly Asn Ile
            115                 120                 125

Gly Pro Gln Gly Lys Pro Gly Pro Lys Gly Glu Ala Gly Pro Lys Gly
130                 135                 140

Glu Val Gly Ala Pro Gly Met Gln Gly Ser Thr Gly Ala Lys Gly Ser
145                 150                 155                 160

Thr Gly Pro Lys Gly Glu Arg Gly Ala Pro Gly Val Gln Gly Ala Pro
                165                 170                 175

Gly Asn Ala Gly Ala Ala Gly Pro Ala Gly Pro Ala Gly Pro Gln Gly
            180                 185                 190

Ala Pro Gly Ser Arg Gly Pro Pro Gly Leu Lys Gly Asp Arg Gly Val
            195                 200                 205

Pro Gly Asp Arg Gly Ile Lys Gly Glu Ser Gly Leu Pro Asp Ser Ala
210                 215                 220

Ala Leu Arg Gln Gln Met Glu Ala Leu Lys Gly Lys Leu Gln Arg Leu
225                 230                 235                 240

Glu Val Ala Phe Ser His Tyr Gln Lys Ala Ala Leu Phe Pro Asp Gly
                245                 250                 255

His Arg Arg Leu Asp Lys Val Glu Glu Val Asn Leu His Glu Asp
            260                 265                 270

Phe Val Phe Ile Lys Lys Leu Lys Arg Cys Asn Lys Gly Glu Gly Ser
            275                 280                 285

Leu Ser Leu Leu Asn Cys Glu Glu Met Arg Arg Gln Phe Glu Asp Leu
290                 295                 300

Val Lys Asp Ile Thr Leu Asn Lys Glu Glu Lys Lys Glu Asn Ser Phe
305                 310                 315                 320

Glu Met Gln Arg Gly Asp Glu Asp Pro Gln Ile Ala Ala His Val Val
                325                 330                 335

Ser Glu Ala Asn Ser Asn Ala Ala Ser Val Leu Gln Trp Ala Lys Lys
            340                 345                 350

Gly Tyr Tyr Thr Met Lys Ser Asn Leu Val Met Leu Glu Asn Gly Lys
            355                 360                 365

Gln Leu Thr Val Lys Arg Glu Gly Leu Tyr Tyr Val Tyr Thr Gln Val
370                 375                 380

Thr Phe Cys Ser Asn Arg Glu Pro Ser Ser Gln Arg Pro Phe Ile Val
385                 390                 395                 400

Gly Leu Trp Leu Lys Pro Ser Ile Gly Ser Glu Arg Ile Leu Leu Lys
                405                 410                 415

Ala Ala Asn Thr His Ser Ser Gln Leu Cys Glu Gln Gln Ser Val
            420                 425                 430

His Leu Gly Gly Val Phe Glu Leu Gln Ala Gly Ala Ser Val Phe Val
            435                 440                 445

Asn Val Thr Glu Ala Ser Gln Val Ile His Arg Val Gly Phe Ser Ser
450                 455                 460

Phe Gly Leu Leu Lys Leu
465                 470
```

-continued

```
<210> SEQ ID NO 16
<211> LENGTH: 786
<212> TYPE: DNA
<213> ORGANISM: Homo sapiens

<400> SEQUENCE: 16
atgatcgaaa catacaacca aacttctccc cgatctgcgg ccactggact gcccatcagc      60
atgaaaattt ttatgtattt acttactgtt tttcttatca cccagatgat tgggtcagca     120 cttttgctg  tgtatcttca tagaaggttg gacaagatag aagatgaaag gaatcttcat     180 gaagatttg  tattcatgaa aacgatacag agatgcaaca caggagaaag atccttatcc     240
ttactgaact gtgaggagat taaaagccag tttgaaggct tgtgaagga  tataatgtta    300 aacaaagagg agacgaagaa agaaaacagc tttgaaatgc aaaaaggtga tcagaatcct    360
caaattgcgg cacatgtcat aagtgaggcc agcagtaaaa caacatctgt gttacagtgg    420
gctgaaaaag gatactacac catgagcaac aacttggtaa ccctggaaaa tgggaaacag    480
ctgaccgtta aaagacaagg actctattat atctatgccc aagtcacctt ctgttccaat    540
cgggaagctt cgagtcaagc tccatttata gccagcctct gcctaaagtc ccccggtaga    600
ttcgagagaa tcttactcag agctgcaaat acccacagtt ccgccaaacc ttgcgggcaa    660
caatccattc acttgggagg agtatttgaa ttgcaaccag gtgcttcggt gtttgtcaat    720
gtgactgatc aagccaagt  gagccatggc actggcttca cgtcctttgg cttactcaaa    780
ctctga                                                              786

<210> SEQ ID NO 17
<211> LENGTH: 261
<212> TYPE: PRT
<213> ORGANISM: Homo sapiens

<400> SEQUENCE: 17

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190
```

Leu Cys Leu Lys Ser Pro Gly Arg Phe Glu Arg Ile Leu Arg Ala
            195                 200                 205

Ala Asn Thr His Ser Ser Ala Lys Pro Cys Gly Gln Gln Ser Ile His
            210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 18
<211> LENGTH: 783
<212> TYPE: DNA
<213> ORGANISM: Mus musculus

<400> SEQUENCE: 18

```
atgatagaaa catacagcca accttccccc agatccgtgg caactggact tccagcgagc    60
atgaagattt ttatgtattt acttactgtt ttccttatca cccaaatgat tggatctgtg   120
cttttttgctg tgtatcttca tagaagattg gataaggtcg aagaggaagt aaaccttcat   180
gaagattttg tattcataaa aaagctaaag agatgcaaca aaggagaagg atctttatcc   240
ttgctgaact gtgaggagat gagaaggcaa tttgaagacc ttgtcaagga tataacgtta   300
aacaaagaag agaaaaaaga aaacagcttt gaaatgcaaa gaggtgatga ggatcctcaa   360
attgcagcac acgttgtaag cgaagccaac agtaatgcag catccgttct acagtggggcc   420
aagaaaggat attataccat gaaaagcaac ttggtaatgc ttgaaaatgg gaaacagctg   480
acggttaaaa gagaaggact ctattatgtc tacactcaag tcaccttctg ctctaatcgg   540
gagccttcga gtcaacgccc attcatcgtc ggcctctggc tgaagcccag cagtggatct   600
gagagaatct tactcaaggc ggcaaatacc cacagttcct cccagctttg cgagcagcag   660
tctgttcact tgggcggagt gtttgaatta caagctggtg cttctgtgtt tgtcaacgtg   720
actgaagcaa gccaagtgat ccacagagtt ggcttctcat cttttggctt actcaaactc   780
tga                                                                 783
```

<210> SEQ ID NO 19
<211> LENGTH: 260
<212> TYPE: PRT
<213> ORGANISM: Mus musculus

<400> SEQUENCE: 19

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
                20                  25                  30

Ile Thr Gln Met Ile Gly Ser Val Leu Phe Ala Val Tyr Leu His Arg
            35                  40                  45

Arg Leu Asp Lys Val Glu Glu Val Asn Leu His Glu Asp Phe Val
        50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

```
Gln Arg Gly Asp Glu Asp Pro Gln Ile Ala Ala His Val Val Ser Glu
            115                 120                 125

Ala Asn Ser Asn Ala Ala Ser Val Leu Gln Trp Ala Lys Lys Gly Tyr
        130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
            195                 200                 205

Asn Thr His Ser Ser Ser Gln Leu Cys Glu Gln Gln Ser Val His Leu
        210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
            245                 250                 255

Leu Leu Lys Leu
        260

<210> SEQ ID NO 20
<211> LENGTH: 930
<212> TYPE: DNA
<213> ORGANISM: Mus musculus

<400> SEQUENCE: 20
atggatcagc acacactgga cgtggaggat accgctgacg ctaggcaccc agctggcacc      60
tcctgccctt ctgatgccgc tctgctgcgc gacacaggac tgctggccga tgccgctctg     120
ctgtctgaca cagtgcggcc aaccaacgcc gctctgccaa ccgatgctgc ttaccctgct     180
gtgaacgtga gggacagaga ggctgcttgg ccacctgccc tgaacttctg cagccgccac     240
cctaagctgt acggcctggt ggccctggtg ctgctgctgc tgatcgctgc ttgcgtgcca     300
atctttaccc ggacagagcc acgccccgct ctgacaatca ccacatcccc caacctgggc     360
accagggaga caacgccga tcaggtgaca ccagtgtctc acatcggctg ccccaacacc     420
acacagcagg aagcccagt gttcgccaag ctgctggcta agaaccaggc cagcctgtgc     480
aacaccacac tgaactggca cagccaggac ggagctggaa gctcctacct gtcccagggc     540
ctgagatacg aggaggataa gaaggagctg gtggtggact cccctggact gtactacgtg     600
ttcctggagc tgaagctgtc tccaaccttt acaaacaccg ccacaaggt gcagggatgg     660 gtgtctctgg tgctgcaggc taagcccag gtggacgatt cgataaccct ggccctgacc     720
gtggagctgt tccttgtag catggagaac aagctggtgg acaggtcttg agccagctg     780 ctgctgctga aggctggcca caggctgtcc gtgggactga gagcctacct gcacggcgcc     840
caggatgctt acagagactg ggagctgagc taccctaaca ccacatcctt cggactgttt     900
ctggtgaagc ctgacaaccc atgggagtga                                     930

<210> SEQ ID NO 21
<211> LENGTH: 765
<212> TYPE: DNA
<213> ORGANISM: Homo sapiens

<400> SEQUENCE: 21
```

```
atggagtacg cctctgacgc cagcctggat ccagaggccc cttggccacc tgcaccaagg    60
gcccgcgcct gccgcgtgct gccctgggcc ctggtggccg gcctgttatt actgctgctg   120
ctggccgccg cctgcgccgt gttcctggca tgtccttggg ccgtgagcgg agccagagcc   180
tccccaggct ctgccgccag ccctcggctg agagagggac cagagctgtc cccagacgat   240
ccagcaggcc tgctggacct gaggcaggga atgtttgccc agctggtggc ccagaacgtg   300
ctgctgatcg acgccccct gtcctggtac tctgatcctg gcctggcgg cgtgtctctg     360
accggcggcc tgagctataa ggaggataca aaggagctgg tggtggccaa ggccggcgtg   420
tactacgtgt cttccagct ggagctgagg agagtggtgg caggagaggg ctctggaagc    480
gtgtccctgg ccctgcacct gcagccctg cggagcgccg caggagccgc cgccctggcc    540
ctgaccgtgg acctgccacc agccagctcc gaggcaagga attccgcctt cggctttcag   600
ggcagactgc tgcacctgtc tgccggacag aggctggag tgcacctgca caccgaggcc    660
agggcccgcc acgcatggca gctgacccag ggagcaacag tgctgggcct gttccgcgtg   720
acacctgaga tcccagcagg cctgcctagc ccacggtccg agtga                   765

<210> SEQ ID NO 22
<211> LENGTH: 1389
<212> TYPE: DNA
<213> ORGANISM: Mus musculus

<400> SEQUENCE: 22
atgctgcctt tcctgtccat gctggtgctg ctggtgcagc cactgggcaa cctgggagcc    60
gagatgaagt ctctgagcca gcgcagcgtg cctaacacct gcacactggt catgtgctcc   120
cctacagaga acggcctgcc aggaagggac ggaagagatg gaagggaggg accaagggga   180
gagaagggcg accccggact gcctggacca atgggactga gcggcctgca gggaccaacc   240
ggccccgtgg gacctaaggg agagaacgga tccgctggag agccaggacc taagggagag   300
agaggactgt ctggaccacc tggactgcca ggaatcccag accagctggg caaggaggga   360
ccatccggca gcagggaaa catcggacca cagggaaagc ctggaccaaa gggagaggct   420
ggacctaagg gagaagtggg cgccccagga atgcagggct ctacaggagc taagggcagc   480
accggaccaa agggagagag gggagccccc ggagtgcagg gagcccctgg caacgctgga   540
gccgctggcc cagccggacc cgctggccct cagggagccc ccggctctag ggaccacca    600
ggcctgaagg gagacagagg cgtgcccgga gatcggggca tcaagggaga gagcggcctg   660
cctgactccg ccgctctgag acagcagatg gaggctctga agggcaagct gcagcggctg   720
gaggtggcct tctcccacta ccagaaggcc gctctgtttc ctgacggaag gacagagccc   780
aggcctgctc tgaccatcac cacatctcca aacctgggca agagagagaa caacgccgat   840
caggtgaccc ccgtgtctca catcggatgc cctaacacca cacagcaggg cagccccgtg   900
tttgccaagc tgctggctaa gaaccaggcc agcctgtgca caccacact gaactggcac   960
tcccaggatg gcgccggaag ctcctacctg tctcagggcc tgcggtacga ggaggacaag  1020
aaggagctgg tggtggatag cccaggcctg tactacgtgt cctggagct gaagctgtcc   1080
cccaccttta caaacaccgg acacaaggtg caggatgggt gagcctggt gctgcaggct   1140
aagccccagg tggacgattt cgacaacctg gccctgaccg tggagctgtt ccttgctct   1200
atggagaaca gctggtgga tagatcctgg agccagctgc tgctgctgaa ggctggacac   1260
cgcctgagcg tgggcctgag gcttacctg cacggagctc aggacgctta cagggattgg  1320
gagctgtcct accctaacac cacatctttc ggcctgtttc tggtgaagcc agacaacccc  1380
``` tgggagtga                                                              1389

<210> SEQ ID NO 23
<211> LENGTH: 1389
<212> TYPE: DNA
<213> ORGANISM: Homo sapiens

<400> SEQUENCE: 23
atgctgctgt tcctgctgtc cgccctggtg ctgctgaccc agcctctggg ctacctggag      60
gccgagatga agacctattc tcaccggaca atgccaagcg cctgcacact ggtcatgtgc     120
agcagcgtgg agtctggcct gccaggaagg gacggaaggg atggaaggga gggacctaga     180
ggcgagaagg gcgaccctgg cctgccagga gcagcaggac aggcaggaat gcccggccag     240
gccggccccg tgggacctaa gggcgacaac ggaagcgtgg gagagccagg accaaagggc     300
gataccggcc cttccggacc acctggacca ccaggcgtgc ctggcccagc cggcagggag     360
ggccctctgg gcaagcaggg caatatcggc ccacagggca agcccggccc taagggcgag     420
gccggcccca gggcgaagt gggcgccect ggcatgcagg aagcgccgg agcccgcggc     480 ctggccggac ctaagggcga gagggcgtg cctggagaga ggggcgtgcc aggaaacaca     540
ggcgcagcag atctgccgg agcaatggga ccccagggca gccctggcgc aggggccct     600 ccaggcctga gggcgacaa gggcatccca ggcgataagg gagcaaaggg agagagcggc     660
ctgccagatg tggcctccct cgccagcag gtggaggccc tgcagggcca ggtgcagcac     720
ctgcaggccg ccttctctca gtacaagaag gtggagctgt ttccaaacgg cgcctgcccc     780
tgggccgtga gcggagcccg ggcctcccca ggctctgccg ccagccctag gctgcgcgag     840
ggaccagagc tgagcccaga cgatccagca ggcctgctgg acctgagaca gggaatgttc     900
gcccagctgg tgcccagaa tgtgctgctg atcgacggcc cactgtcctg gtactctgat     960
ccaggcctgg ccggcgtgtc cctgaccggc ggcctgtctt ataaggagga tacaaaggag    1020
ctggtggtgg ccaaggccgg cgtgtactac gtgttcttcc agctggagct gaggagagtg    1080
gtggcaggag agggatccgg atctgtgagc ctggccctgc acctgcagcc cctgcgtcc    1140 gccgcaggag ccgccgccct ggccctgacc gtggacctgc acctgcctc tagcgaggca    1200 cgcaattccg ccttcggctt tcagggccgg ctgctgcacc tgtctgccgg acagagactg    1260
ggagtgcacc tgcacaccga ggcccgggcc agacacgcct ggcagctgac ccaggggca    1320 acagtgctgg gcctgttag ggtgacacct gagatcccag ccggcctgcc aagccccgc    1380 tccgagtga                                                              1389

<210> SEQ ID NO 24
<211> LENGTH: 522
<212> TYPE: DNA
<213> ORGANISM: Mus musculus

<400> SEQUENCE: 24
atggaggaga tgcctctgag ggagagctcc ccacagaggg ccgagagatg caagaagagc      60
tggctgctgt gcatcgtggc tctgctgctg atgctgctgt gctctctggg caccctgatc     120
tacacaagcc tgaagccaac cgccatcgag tcctgtatgt gaagttcga gctgtctagc     180 tccaagtggc acatgacatc ccccaagcct cactgcgtga acaccacatc tgacggaaag     240
ctgaagatcc tgcagagcgg cacctacctg atctacgaca aggtcatccc cgtggacaag     300
aagtacatca aggataacgc cccctttcgt ggtgcagatct acaagaagaa cgacgtgctg     360

| | |
|---|---|
| cagacactga tgaacgattt tcagatcctg cccatcggcg gagtgtacga gctgcacgct | 420 |
| ggcgacaaca tctacctgaa gttcaactcc aaggatcaca tccagaagac caacacatac | 480 |
| tggggaatca tcctgatgcc agatctgccc tttatctctt ga | 522 |

```
<210> SEQ ID NO 25
<211> LENGTH: 600
<212> TYPE: DNA
<213> ORGANISM: Homo sapiens

<400> SEQUENCE: 25
```

| | |
|---|---|
| atgaccctgc acccaagccc catcacatgc gagttcctgt tttctaccgc cctgatcagc | 60 |
| ccaaagatgt gcctgagcca cctggagaat atgcccctgt cccactctcg gacacaggga | 120 |
| gcccagagaa gctcctggaa gctgtggctg ttctgctcta tcgtgatgct gctgttcctg | 180 |
| tgcagctttt cctggctgat cttcatcttt ctgcagctgg agacagccaa ggagccttgc | 240 |
| atggccaagt ttggccctct gccatccaag tggcagatgg cctctagcga gccccttgc | 300 |
| gtgaacaagg tgagcgactg gaagctggag atcctgcaga acggcctgta cctgatctat | 360 |
| ggccaggtgg cccccaacgc caattacaac gacgtggccc ctttcgaggt gcggctgtat | 420 |
| aagaacaagg atatgatcca gaccctgaca aataagtcta agatccagaa cgtgggcggc | 480 |
| acatacgagc tgcacgtggg cgacaccatc gacctgatct tcaacagcga gcaccaggtg | 540 |
| ctgaagaaca atacatattg gggcatcatc ctgctggcca ccccagtt tatctcctga | 600 |

```
<210> SEQ ID NO 26
<211> LENGTH: 1164
<212> TYPE: DNA
<213> ORGANISM: Mus musculus

<400> SEQUENCE: 26
```

| | |
|---|---|
| atgctgcctt tcctgtctat gctggtgctg ctggtgcagc cactgggcaa cctgggagcc | 60 |
| gagatgaaga gcctgtccca gagatccgtg cccaacacct gcacactggt catgtgctct | 120 |
| cctaccgaga acggcctgcc aggaagggac ggaagagatg gaagggaggg acctcgggga | 180 |
| gagaagggcg acccaggact gcctggacca atgggactga gcggcctgca gggaccaaca | 240 |
| ggccccgtgg gacctaaggg agagaacgga agcgccggag agccaggacc taagggagag | 300 |
| agggactgt ccggaccacc tggactgcct ggaatcccag accagctgg caaggaggga | 360 |
| ccatccggca agcagggaaa catcggacca cagggaaagc ctggaccaaa gggagaggct | 420 |
| ggaccaaagg gagaagtggg cgctcctgga atgcagggct ccaccggagc caagggctct | 480 |
| acaggaccaa aggagagag gggagctccc ggagtgcagg gagcccctgg caacgctgga | 540 |
| gccgctggcc cagccggacc cgctggccct caggagccc caggcagcag ggaccaccc | 600 |
| ggcctgaagg gcgacagggg cgtgccagga gatagggggca tcaagggaga gtctggcctg | 660 |
| ccagacagcg ccgctctgag acagcagatg gaggccctga agggcaagct gcagcggctg | 720 |
| gaggtggctt tctcccacta ccagaaggcc gctctgtttc cagatggcag cctgaagccc | 780 |
| accgccatcg agtcctgcat ggtgaagttt gagctgagct cctctaagtg gcacatgaca | 840 |
| tctcccaagc ctcactgcgt gaacaccaca tctgacggca gctgaagat cctgcagagc | 900 |
| ggcacctacc tgatctacgg ccaggtcatc cccgtggaca agaagtacat caaggataac | 960 |
| gcccctttcg tggtgcagat ctacaagaag aacgacgtgc tgcagacact gatgaacgat | 1020 |
| tttcagatcc tgccaatcgg cggagtgtac gagctgcacg ctggcgacaa catctacctg | 1080 |
| aagttcaact ctaaggatca catccagaag accaacacat actggggcat catcctgatg | 1140 |

```
ccagatctgc cctttatcag ctga                                          1164
```

<210> SEQ ID NO 27
<211> LENGTH: 1152
<212> TYPE: DNA
<213> ORGANISM: Homo sapiens

<400> SEQUENCE: 27

```
atgctgctgt tcctgctgtc tgccctggtg ctgctgaccc agccactggg ctacctggag   60
gccgagatga agacctattc ccaccgcaca atgccttctg cctgcacact ggtcatgtgc  120
agcagcgtgg agagcggcct gccaggaagg gacggaagag atggaaggga gggacccaga  180
ggcgagaagg gcgaccctgg cctgccagga gcagcaggac aggcaggaat gccaggccag  240
gccggccccg tgggccctaa gggcgacaat ggatccgtgg gagagccagg accaaagggc  300
gataccggcc cttctggacc acctggacca ccaggcgtgc ctggaccagc aggaagagag  360
ggacctctgg gcaagcaggg aaacatcgga ccacagggca agccaggccc taagggcgag  420
gccggcccca gggcgaagt gggcgcccct ggcatgcagg atccgccgg agccagggc  480
ctggccggac ctaagggcga gcgcggcgtg cctggagaga gggcgtgcc aggaaataca  540
ggcgcagcag gatctgccgg agcaatggga ccacagggca gccccggcgc cagaggccct  600
ccaggcctga gggcgacaa gggaatccct ggcgataagg gagcaaaggg agagagcggc  660
ctgccagacg tggcctccct gaggcagcag gtggaggccc tgcagggaca ggtgcagcac  720
ctgcaggccg ccttcagcca gtacaagaag gtggagctgt ttccaaatgg cgagacagcc  780
aaggagccct gcatggccaa gttcggccca ctgcccagca gtggcagat ggcctctagc  840
gagccccctt gcgtgaacaa ggtgagcgat tggaagctgg agatcctgca gaacggcctg  900
tacctgatct atggccaggt ggcccccaac gccaattaca cgacgtggc cccttttgag  960
gtgcggctgt ataagaacaa ggatatgatc cagaccctga caaataagtc taagatccag 1020
aacgtgggag gcacctacga gctgcacgtg ggcgacacaa tcgacctgat cttcaacagc 1080
gagcaccagg tgctgaagaa caatacatat tggggcatca tcctgctggc caaccccag 1140
tttatctcct ga                                                     1152
```

<210> SEQ ID NO 28
<211> LENGTH: 597
<212> TYPE: DNA
<213> ORGANISM: Mus musculus

<400> SEQUENCE: 28

```
atggagggcg agggagtgca gcccctggat gagaacctgg agaacggctc ccggcctcgc   60
ttcaagtgga gaagaccct gcggctggtg gtgtctggaa tcaagggcgc cggaatgctg  120
ctgtgcttta tctacgtgtg cctgcagctg agctcctctc ccgccaagga tccccctatc  180
cagaggctga gaggagctgt gaccaggtgc gaggacggac agctgttcat cagctcctac  240
aagaacgagt accagacaat ggaggtgcag aacaacagcg tggtcatcaa gtgtgatggc  300
ctgtacatca tctacctgaa gggatccttc tttcaggagg tgaagatcga cctgcacttt  360
cgggaggatc acaacccaat ctctatcccc atgctgaacg acggcaggag aatcgtgttc  420
acagtggtgg ccagcctggc ttttaaggac aaggtgtacc tgaccgtgaa cgccccagat  480
acactgtgcg agcacctgca gatcaacgac ggagagctga tcgtggtgca gctgaccccct  540
ggctactgtg ctccagaggg atcttaccac agcacagtga accaggtgcc cctgtga     597
```

```
<210> SEQ ID NO 29
<211> LENGTH: 552
<212> TYPE: DNA
<213> ORGANISM: Homo sapiens

<400> SEQUENCE: 29
atggagaggg tgcagcccct ggaggagaac gtgggaaatg ccgcccggcc tagattcgag      60
aggaacaagc tgctgctggt ggcctctgtg atccagggcc tgggcctgct gctgtgcttc     120
acctacatct gtctgcactt ttctgccctg caggtgagcc acagataccc ccgcatccag     180
agcatcaagg tgcagttcac cgagtataag aaggagaagg gctttatcct gacatcccag     240
aaggaggacg agatcatgaa ggtgcagaac aattctgtga tcatcaactg cgatggcttc     300
tacctgatct ccctgaaggg ctattttttct caggaagtga atatcagcct gcactatcag     360
aaggacgagg agccactgtt tcagctgaag aaggtgcgga gcgtgaattc cctgatggtg     420
gccagcctga cctacaagga caaggtgtat ctgaacgtga ccacagataa tacatccctg     480
gacgatttcc acgtgaacgg cggcgagctg atcctgatcc accagaatcc cggcgagttt     540
tgcgtgctgt ga                                                          552

<210> SEQ ID NO 30
<211> LENGTH: 1215
<212> TYPE: DNA
<213> ORGANISM: Mus musculus

<400> SEQUENCE: 30
atgctgccct tcctgtccat gctggtgctg ctggtgcagc ctctgggcaa cctgggagcc      60
gagatgaagt ctctgagcca gagatccgtg ccaaacacct gcacactggt catgtgctct     120
cccaccgaga acggcctgcc tggaagggac ggaagagatg aaggagggg accccgggga     180 gagaagggcg atcctggact gccaggacct atgggactga gcggcctgca gggaccaaca     240
ggccccgtgg gacctaaggg agagaacgga agcgccggag agccaggacc aaagggagag     300
aggggactgt ccggcccacc tggactgcct ggaatccctg accagctgg caaggaggga     360 ccttccggca gcagggaaa catcggacca caggaaagc caggacctaa gggagaggct     420
ggaccaaagg gagaagtggg cgctcccgga atgcagggct ctaccggagc caagggcagc     480
acaggaccta agggagagag gggagctcca ggagtgcagg gagcccccgg caacgctgga     540
gctgctggac cagctggacc agctggccct cagggagccc caggctctag ggaccacca     600 ggcctgaagg gcgacagggg cgtgccagga gatagggca tcaagggaga gagcggcctg     660
ccagattccg ccgctctgag acagcagatg gaggccctga agggcaagct gcagcggctg     720
gaggtggctt tcagccacta ccagaaggcc gctctgtttc ctgacggcag ctcctctcca     780
gccaaggatc ctccaatcca gcggctgcgc ggagctgtga ccaggtgcga ggatggccag     840
ctgttcatca gctcctacaa gaacgagtac cagacaatgg aggtgcagaa caactctgtg     900
gtcatcaagt gtgacggcct gtacatcatc tacctgaagg gcagcttctt tcaggaggtg     960
aagatcgacc tgcactttag agaggatcac aacccaatct ccatcccat gctgaacgac    1020 ggcaggagaa tcgtgttcac cgtggtggcc tctctggctt taaggacaa ggtgtacctg    1080 accgtgaacg cccccgatac actgtgcgag cacctgcaga tcaacgacgg cgagctgatc    1140
gtggtgcagc tgacccctgg atactgtgct ccagagggct cctaccactc tacagtgaac    1200
caggtgcctc tgtga                                                     1215
```

<210> SEQ ID NO 31
<211> LENGTH: 1170
<212> TYPE: DNA
<213> ORGANISM: Homo sapiens

<400> SEQUENCE: 31

```
atgctgctgt tcctgctgag cgccctggtg ctgctgaccc agccactggg ctacctggag     60
gccgagatga agacctattc ccacagaaca atgccttctg cctgcacact ggtcatgtgc    120
agcagcgtgg agtccggcct gccaggaagg gacggcagag atggcaggga gggccccagg    180
ggcgagaagg gcgaccccgg cctgcctgga gcagcaggcc aggccggcat gccaggccag    240
gccggcccag tgggccccaa gggcgacaac ggcagcgtgg gcgagcccgg ccctaagggc    300
gataccggcc cctccggccc ccctggccca cccggcgtgc caggaccagc aggaagggag    360
ggaccactgg gcaagcaggg caatatcgga cctcagggca gcctggacc aaagggagag    420 gcaggaccaa agggagaagt gggcgcccct ggcatgcagg atctgccgg agcccggggc    480 ctggccggcc ccaagggcga gagaggcgtg cccggcgaga gggcgtgcc tggcaacaca    540 ggcgccgccg gctccgccgg cgccatggga cctcagggct ctccaggagc cagaggccct    600
ccaggcctga gggcgacaa gggaatccct ggcgataagg gagcaaaggg agagagcggc    660
ctgccagacg tggcctccct gcggcagcag gtggaggccc tgcagggcca ggtgcagcac    720
ctgcaggccg ccttcagcca gtacaagaag gtggagctgt ttcctaatgg cgtgtctcac    780
cgctacccac ggatccagag catcaaggtg cagttcaccg agtataagaa ggagaagggc    840
tttatcctga catctcagaa ggaggacgag atcatgaagg tgcagaacaa tagcgtgatc    900
atcaactgcg atggcttcta cctgatcagc ctgaagggct attttttccca ggaagtgaat    960 atctctctgc actatcagaa ggatgaggag cctctgtttc agctgaagaa ggtgagatct   1020
gtgaacagcc tgatggtggc ctccctgacc tacaaggaca aggtgtatct gaacgtgacc   1080
acagataata catctctgga cgatttccac gtgaacggcg gcgagctgat cctgatccac   1140
cagaatcccg gcgagttttg cgtgctgtga                                     1170
```

<210> SEQ ID NO 32
<211> LENGTH: 969
<212> TYPE: DNA
<213> ORGANISM: Mus musculus

<400> SEQUENCE: 32

```
atgcagctga agtgtccatg cttcgtgtcc ctgggaacaa gacagcccgt ctggaagaaa     60
ctgcacgtga gctccggctt ctttagcggc ctggggctgt ttctgctgct gctgtctagt    120
ctgtgcgccg cttccgcaga gactgaagtc ggagccatgg tgggcagtaa cgtggtcctg    180
tcatgcatcg acccacaccg acggcatttc aacctgtctg gcctgtacgt gtattggcag    240
attgagaatc ccgaagtgtc agtcacctac tatctgcctt acaagagccc agggatcaac    300
gtggactcaa gctataaaaa tagggggcac ctgtccctgg attctatgaa gcagggaaac    360
ttcagcctgt acctgaaaaa tgtgacccct caggacacac aggagttcac ttgtcgcgtc    420
tttatgaaca ctgcaaccga actggtgaag attctggagg aagtggtccg gctgagagtc    480
gcagccaact ttagcactcc tgtgatctct accagtgatt cctctaatcc aggccaggag    540
cggacatata cttgcatgtc taagaacgga taccccgaac ctaatctgta ttggatcaac    600
accacagaca taagtctgat tgataccgct ctgcagaaca atacagtcta cctgaacaag    660
ctggggctgt atgacgtgat ctctactctg cggctgccat ggaccagtag aggagatgtg    720
```

```
ctgtgctgcg tggagaacgt ggccctgcac cagaatatca cctcaattag ccaggctgag    780
tcctttaccg gcaacaatac aaagaatcct caggagacac ataacaatga actgaaagtg    840
ctggtgccag tgctggccgt cctggctgca gcagctttcg tgtcttttat catctacaga    900
aggacccgcc ctcaccgctc atacactgga cctaagaccg tgcagctgga actgacagac    960
catgcttga                                                            969
```

```
<210> SEQ ID NO 33
<211> LENGTH: 909
<212> TYPE: DNA
<213> ORGANISM: Homo sapiens

<400> SEQUENCE: 33
atgcgtctgg gttcacctgg tctgctgttt ctgctgtttt caagtctgcg tgctgatact     60
caggagaagg aagtccgggc tatggtcgga agtgacgtgg agctgtcatg cgcttgtccc    120
gaagggtccc ggttcgacct gaacgatgtc tacgtgtatt ggcagacctc tgagagtaag    180
accgtggtca cataccacat ccctcagaac tccagcctgg aaaatgtgga ttcaaggtat    240
cggaacagag ccctgatgtc ccctgctggc atgctgcggg agacttctc tctgagactg    300 tttaatgtga caccacagga tgagcagaaa ttccattgcc tggtcctgtc acagtccctg    360
ggatttcagg aggtgctgag tgtcgaagtg actctgcacg tcgccgctaa tttctccgtg    420
cctgtggtca gcgcaccaca tagcccctct caggacgagc tgacctttac atgtacttcc    480
atcaacggct accccgccc taacgtgtac tggattaaca agactgacaa tagcctgctg    540
gatcaggcac tgcagaacga caccgtgttt ctgaatatgc gaggactgta cgatgtggtc    600
agcgtcctgc gtattgccag gaccccatct gtgaacatcg ggtgctgtat tgagaacgtc    660
ctgctgcaga gaatctgac agtggggagc cagactggta atgacatcgg cgagagggat    720
aagattaccg aaaaccccgt gagtacaggc gagaagaacg cagccacatg gtcaatcctg    780
gctgtgctgt gcctgctggt ggtcgtggct gtcgcaattg ctgggtgtg ccgcgatcgg    840 tgtctgcagc actcttatgc cggtgcttgg gcagtgagtc cagagactga actgaccggc    900
catgtctaa                                                            909
```

```
<210> SEQ ID NO 34
<211> LENGTH: 1574
<212> TYPE: DNA
<213> ORGANISM: Mus musculus

<400> SEQUENCE: 34
cttaagatgg aaactgatac tctgctgctc tgggtgctgc tcctctgggt gcctggttca     60
actggggaca ttcgacgggc tgacattgtg atgacccaga ccacactgag cctgcccgtg    120
tccctgggcg accaggccag catctcctgc cggagctccc agtctatcgt gcacagcaac    180
ggaaacacat acctggagtg gtatctgcag aagcctggcc agtccccaaa gctgctgatc    240
tacaaggtgt ccaacaggtt cagcggcgtg cctgaccgct tttctggaag cggctccgga    300
acagatttca ccctgaagat cagcagggtg gaggctgagg acctgggcgt gtactactgc    360
ttccagggat cccacgtgcc ttacacctt ggcggaggca aaagctgga gatcaagaga    420 gccgatgctg ctccaaccgt gtctggaagc ggaggcgggg gttctggagg cggtgggagc    480
ggtggcggag ggtctgaggc taagctgcag gagagcggcc ccgtgctggt gaagcctgga    540
gccagcgtga gatgtcctg taaggcttct ggatacacct tcacagacta ctacatgaac    600
tgggtgaagc agagccacgg caagtccctg gagtggatcg gagtgatcaa cccttacaac    660
```

```
ggcgacacct cttacaacca gaagtttaag ggcaaggcca ccctgacagt ggataagtct      720
agctccaccg cttacatgga gctgaacagc ctgacatccg aggattctgc cgtgtactac      780
tgtgctaggt actacggaag ctggttcgcc tactggggcc agggaacact gatcaccgtg      840
tccacagcca agaccacacc ccctagcgtg taccccctgg ctcctaggtc tagcagaggc      900
tgcaagccat gcatctgtac cgtgcccgag gtgagcagcg tgttcatctt ccacccaag       960 cccaaggacg tgctgaccat cacactgacc cctaaggtga catgcgtggt ggtggatatc     1020
agcaaggacg atccagaggt gcagttctcc tggtttgtgg acgatgtgga ggtgcacacc     1080
gcccagacac agccaaggga ggagcagttc aactccacct ttagatccgt gtctgagctg     1140
cccatcatgc accaggactg gctgaacgga aaggagttca gtgccgggt gaactccgcc      1200 gcttttcctg ctccaatcga aagaccatc tctaagacaa agggccgccc aaaggctcca     1260
caggtgtaca ccatccctcc acccaaggag cagatggcta aggataaggt gagcctgacc     1320
tgtatgatca cagacttctt tcccgaggat atcacagtgg agtggcagtg aacggacag     1380 cctgccgaga actacaagaa cacccagcca atcatggaca cagatggctc ttacttcgtg     1440
tacagcaagc tgaacgtgca gaagtctaac tgggaggctg gcaacacctt cacctgcagc     1500
gtgctgcacg aaggtctcca taatcaccac accgaaaaga gcctcagtca gcccctggg     1560 aaatgaggcg cgcc                                                      1574
```

<210> SEQ ID NO 35
<211> LENGTH: 1484
<212> TYPE: DNA
<213> ORGANISM: Homo sapiens

<400> SEQUENCE: 35

```
cttaagatgg aaactgacac cctgctgctg tgggtcctgc tgctgtgggt gcctggatcc       60
accggcgata tcgtgctgac ccagtctcct ggcacactga gtctgtcacc aggggagcga      120
gcaacactgt cttgtagagc cagccagtct gtgggaagct cctacctggc ttggtatcag      180
cagaagccag gccaggcacc caggctgctg atctacggag ccttcagccg ggccactggc      240
attccagaca ggttctctgg aagtggctca gggaccgact tcaccctgac catcagccga      300
ctggagcccg aagacttcgc cgtgtactat tgccagcagt acggctctag tccttggact      360
tttggacagg gcaccaaagt ggagatcaag cgcggcgggg gaggctctgg gggaggcggg      420
agtggaggcg ggggatcaca ggtccagctg gtggaaagcg gcgggggagt ggtccagcca      480
ggccggagcc tgcggctgag ctgcgccgct tcaggattca cattttcaag ctataccatg      540
cactgggtcc ggcaggcacc agggaaggga ctggagtggg tgaccttcat cagctatgac      600
ggcaacaaca gtattacgc tgattccgtg aaagggaggt ttaccattag ccgcgacaac      660
tccaaaaata cactgtacct gcagatgaac agcctgcggg ccgaggatac tgctatctac      720
tattgcgcaa gaaccgggtg gctgggaccc ttcgactatt ggggccaggg gactctggtc      780
accgtgtcct ctgataagac acacacatgc cctccctgtc ctgcaccaga gctgctgggc      840
gggccatccg tgttcctgtt tccacccaag cctaaagaca ccctgatgat cagccggaca      900
cctgaagtca cttgcgtggt cgtggacgtg agtcacgagg atccagaagt caagtttaac      960
tggtacgtgg atggcgtcga ggtgcataat gccaagacca aacctcgcga ggaacagtac     1020
aatagcacat atcgagtcgt gtccgtcctg actgtgctgc atcaggattg gctgaacggc     1080
aaagagtata agtgcaaagt gagcaataag gcactgcctg ccccaatcga gaaaacaatt     1140
```

| | |
|---|---|
| tccaaggcta aaggccagcc cagggaacct caggtgtaca ctctgcctcc aagtcgcgag | 1200 |
| gaaatgacca agaaccaggt gagcctgacc tgtctggtga aagggttcta tcccatcagac | 1260 |
| attgcagtgg agtgggaaag caatggacag cccgaaaaca attacaagac cacaccccct | 1320 |
| gtgctggaca gcgatggctc cttctttctg tattctaagc tgactgtgga taaaagtcgc | 1380 |
| tggcagcagg ggaacgtctt tagctgttcc gtgatgcatg aggctctgca caatcattac | 1440 |
| acacagaagt ctctgagtct gtcacccggc aaatgaggcg cgcc | 1484 |

<210> SEQ ID NO 36
<211> LENGTH: 632
<212> TYPE: DNA
<213> ORGANISM: Artificial Sequence
<220> FEATURE:
<223> OTHER INFORMATION: CMV promoter

<400> SEQUENCE: 36

| | |
|---|---|
| gttgacattg attattgact agttattaat agtaatcaat tacgggtca ttagttcata | 60 |
| gcccatatat ggagttccgc gttacataac ttacggtaaa tggcccgcct ggctgaccgc | 120 |
| ccaacgaccc ccgcccattg acgtcaataa tgacgtatgt tcccatagta acgccaatag | 180 |
| ggactttcca ttgacgtcaa tgggtggagt atttacggta aactgcccac ttggcagtac | 240 |
| atcaagtgta tcatatgcca agtacgcccc ctattgacgt caatgacggt aaatggcccg | 300 |
| cctggcatta tgcccagtac atgaccttat gggactttcc tacttggcag tacatctacg | 360 |
| tattagtcat cgctattacc atggtgatgc ggttttggca gtacatcaat gggcgtggat | 420 |
| agcggtttga ctcacgggga tttccaagtc tccaccccat tgacgtcaat gggagtttgt | 480 |
| tttggcacca aaatcaacgg gactttccaa aatgtcgtaa caactccgcc ccattgacgc | 540 |
| aaatgggcgg taggcgtgta cggtgggagg tctatataag cagagctctc tggctaacta | 600 |
| gagaacccac tgcttactgg cttatcgaaa tt | 632 |

<210> SEQ ID NO 37
<211> LENGTH: 394
<212> TYPE: DNA
<213> ORGANISM: Artificial Sequence
<220> FEATURE:
<223> OTHER INFORMATION: RSV promoter

<400> SEQUENCE: 37

| | |
|---|---|
| tgtacgggcc agatatacgc gtatctgagg ggactagggt gtgtttaggc gaaaagcggg | 60 |
| gcttcggttg tacgcggtta ggagtcccct caggatatag tagtttcgct tttgcatagg | 120 |
| gagggggaaa tgtagtctta tgcaatacac ttgtagtctt gcaacatggt aacgatgagt | 180 |
| tagcaacatg ccttacaagg agagaaaaag caccgtgcat gccgattggt ggaagtaagg | 240 |
| tggtacgatc gtgccttatt aggaaggcaa cagacaggtc tgacatggat tggacgaacc | 300 |
| actgaattcc gcattgcaga gataattgta tttaagtgcc tagctcgata caataaacgc | 360 |
| catttgacca ttcaccacat tggtgtgcac ctcc | 394 |

<210> SEQ ID NO 38
<211> LENGTH: 188
<212> TYPE: DNA
<213> ORGANISM: Artificial Sequence
<220> FEATURE:
<223> OTHER INFORMATION: BGH polyA

<400> SEQUENCE: 38

| | |
|---|---|
| ctgtgccttc tagttgccag ccatctgttg tttgcccctc ccccgtgcct tccttgaccc | 60 |

```
tggaaggtgc cactcccact gtcctttcct aataaaatga ggaaattgca tcgcattgtc    120
tgagtaggtg tcattctatt ctgggggtg gggtggggca ggacagcaag ggggaggatt    180
gggaagac                                                             188
```

<210> SEQ ID NO 39
<211> LENGTH: 249
<212> TYPE: DNA
<213> ORGANISM: Artificial Sequence
<220> FEATURE:
<223> OTHER INFORMATION: SV40 late polyA

<400> SEQUENCE: 39

```
gacatgataa gatacattga tgagtttgga caaaccacaa ctagaatgca gtgaaaaaaa    60
tgctttattt gtgaaatttg tgatgctatt gctttatttg tgaaatttgt gatgctattg   120
ctttatttgt aaccattata agctgcaata acaagttaa caacaacaat tgcattcatt    180
ttatgtttca ggttcagggg gaggtgtggg aggttttta aagcaagtaa aacctctaca    240
aatgtggta                                                            249
```

<210> SEQ ID NO 40
<211> LENGTH: 345
<212> TYPE: DNA
<213> ORGANISM: Artificial Sequence
<220> FEATURE:
<223> OTHER INFORMATION: SV40 enhancer promoter

<400> SEQUENCE: 40

```
gctgtggaat gtgtgtcagt tagggtgtgg aaagtcccca ggctcccag caggcagaag    60 tatgcaaagc atgcatctca attagtcagc aaccaggtgt ggaaagtccc caggctcccc   120
agcaggcaga agtatgcaaa gcatgcatct caattagtca gcaaccatag tcccgcccct   180
aactccgccc atcccgcccc taactccgcc cagttccgcc cattctccgc cccatggctg   240
actaattttt tttatttatg cagaggccga ggccgcctcg gcctctgagc tattccagaa   300
gtagtgagga ggcttttttg gaggcctagg cttttgcaaa aagct                    345
```

<210> SEQ ID NO 41
<211> LENGTH: 99
<212> TYPE: DNA
<213> ORGANISM: Artificial Sequence
<220> FEATURE:
<223> OTHER INFORMATION: Rabbit beta-globin polyA

<400> SEQUENCE: 41

```
gacctctggc taataaagga aatttatttt cattgcaata gtgtgttgga atttttgtg    60 tctctcactc ggaaggacat atgggagggc aaatcattt                           99
```

<210> SEQ ID NO 42
<211> LENGTH: 723
<212> TYPE: DNA
<213> ORGANISM: Artificial Sequence
<220> FEATURE:
<223> OTHER INFORMATION: GFP

<400> SEQUENCE: 42

```
accatggtga gcaagggcga ggagctgttc accggggtgg tgcccatcct ggtcgagctg    60
gacggcgacg taaacggcca caagttcagc gtgtccggcg agggcgaggg cgatgccacc   120
tacggcaagc tgaccctgaa gttcatctgc accaccggca agctgcccgt gccctggccc   180
```

```
accctcgtga ccaccctgac ctacggcgtg cagtgcttca gccgctaccc cgaccacatg    240
aagcagcacg acttcttcaa gtccgccatg cccgaaggct acgtccagga gcgcaccatc    300
ttcttcaagg acgacggcaa ctacaagacc cgcgccgagg tgaagttcga gggcgacacc    360
ctggtgaacc gcatcgagct gaagggcatc gacttcaagg aggacggcaa catcctgggg    420
cacaagctgg agtacaacta caacagccac aacgtctata tcatggccga caagcagaag    480
aacggcatca aggtgaactt caagatccgc cacaacatcg aggacggcag cgtgcagctc    540
gccgaccact accagcagaa cacccccatc ggcgacggcc ccgtgctgct gcccgacaac    600
cactacctga gcacccagtc cgccctgagc aaagacccca acgagaagcg cgatcacatg    660
gtcctgctgg agttcgtgac cgccgccggg atcactctcg gcatggacga gctgtacaag    720
taa                                                                  723
```

```
<210> SEQ ID NO 43
<211> LENGTH: 454
<212> TYPE: DNA
<213> ORGANISM: Artificial Sequence
<220> FEATURE:
<223> OTHER INFORMATION: MoMuLV LTR

<400> SEQUENCE: 43
ttaattaagt aacgccattt tgcaaggcat ggaaaaatac ataactgaga atagagaagt     60
tcagatcaag gtcaggaaca gatggaacag ctgaatatgg gccaaacagg atatctgtgg    120
taagcagttc ctgccccggc tcagggccaa gaacagatgg aacagctgaa tatgggccaa    180
acaggatatc tgtggtaagc agttcctgcc ccggctcagg gccaagaaca gatggtcccc    240
agatgcggtc cagccctcag cagtttctag agaaccatca gatgtttcca gggtgcccca    300
aggacctgaa atgaccctgt gccttatttg aactaaccaa tcagttcgct tctcgcttct    360
gttcgcgcgc ttctgctccc cgagctcaat aaaagagccc acaacccctc actcggggcg    420
ccagtcctcc gattgactga gtcgcccgct taag                                454
```

```
<210> SEQ ID NO 44
<211> LENGTH: 1349
<212> TYPE: DNA
<213> ORGANISM: Artificial Sequence
<220> FEATURE:
<223> OTHER INFORMATION: EF1alpha promoter

<400> SEQUENCE: 44
ttaattaaga gtaattcata caaaaggact cgcccctgcc ttggggaatc ccagggaccg     60
tcgttaaact cccactaacg tagaacccag atcgctgcg t tcccgccc cctcacccgc    120 ccgctctcgt catcactgag gtggagaaga gcatgcgtga ggctccggtg cccgtcagtg    180
ggcagagcgc acatcgccca gtcccccga aagttgggg ggagggtcg gcaattgaac    240 cggtgcctag agaaggtggc gcggggtaaa ctgggaaagt gatgtcgtgt actggctccg    300
cctttttccc gagggtgggg gagaaccgta tataagtgca gtagtcgccg tgaacgttct    360
ttttcgcaac gggtttgccg ccagaacaca ggtaagtgcc gtgtgtggtt cccgcgggcc    420
tggcctcttt acgggttatg gcccttgcgt gccttgaatt acttccacgc ccctggctgc    480
agtacgtgat tcttgatccc gagcttcggg ttggaagtgg gtgggagagt tcgaggcctt    540
gcggttaagg agcccc ttcg cctcgtgctt gagttgaggc ctggcttggg cgctggggcc    600
gccgcgtgcg aatctggtgg caccttcgcg cctgtctcgc tgcttcgat aagtctctag    660 ccatttaaaa ttttgatga cctgctgcga cgctttttt ctggcaagat agtcttgtaa    720
```

```
atgcgggcca agatctgcac actggtattt cggttttggg ggccgcgggc ggcgacgggg        780
cccgtgcgtc ccagcgcaca tgttcggcga ggcggggcct gcgagcgcgg ccaccgagaa        840
tcggacgggg gtagtctcaa gctggccggc ctgctctggt gcctggcctc gcgccgccgt        900
gtatcgcccc gccctgggcg gcaaggctgg cccggtcggc accagttgcg tgagcggaaa        960
gatggccgct tcccggccct gctgcaggga gctcaaaatg gaggacgcgg cgctcgggag       1020
agcgggcggg tgagtcaccc acacaaagga aaagggcctt tccgtcctca gccgtcgctt       1080
catgtgactc cacggagtac cgggcgccgt ccaggcacct cgattagttc tcgagctttt       1140
ggagtacgtc gtctttaggt tggggggagg ggttttatgc gatggagttt ccccacactg       1200
agtgggtgga gactgaagtt aggccagctt ggcacttgat gtaattctcc ttggaatttg       1260 cccttttga gtttggatct tggttcattc tcaagcctca gacagtggtt caaagttttt       1320
ttcttccatt tcaggtgtcg tgacttaag                                         1349

<210> SEQ ID NO 45
<211> LENGTH: 481
<212> TYPE: DNA
<213> ORGANISM: Artificial Sequence
<220> FEATURE:
<223> OTHER INFORMATION: HGH polyA

<400> SEQUENCE: 45
gacgggtggc atccctgtga cccctcccca gtgcctctcc tggccctgga agttgccact         60
ccagtgccca ccagccttgt cctaataaaa ttaagttgca tcattttgtc tgactaggtg        120
tccttctata atattatggg gtggaggggg gtggtatgga gcaaggggca agttgggaag        180
acaacctgta gggcctgcgg ggtctattgg gaaccaagct ggagtgcagt ggcacaatct        240
tggctcactg caatctccgc ctcctgggtt caagcgattc tcctgcctca gcctcccgag        300
ttgttgggat tccaggcatg catgaccagg ctcagctaat ttttgttttt ttggtagaga        360
cggggtttca ccatattggc caggctggtc tccaactcct aatctcaggt gatctaccca        420
ccttggcctc ccaaattgct gggattacag gcgtgaacca ctgctccctt ccctgtcctt        480
t                                                                       481
```

ENGINEERED VIRUS

CROSS-REFERENCE TO RELATED APPLICATIONS

This application is a continuation of U.S. Non-Provisional patent application Ser. No. 16/068,830 filed Jul. 9, 2018, which is a national phase application under 35 U.S.C. § 371 to International Application No. PCT/GB2017/050038 filed Jan. 9, 2017, which claims the benefit of priority to Great Britain Patent Application Serial Nos. 1600380.8, 1600381.6 and 160382.4 all filed Jan. 8, 2016, all of which are incorporated herein by reference in their entirety.

INCORPORATION OF SEQUENCE LISTING

The instant application contains a Sequence Listing, named "SeqLst_KEMP_P0086USC1.TXT" (73,728 bytes; created Feb. 1, 2021) which has been submitted electronically in ASCII format and is hereby incorporated by reference in its entirety.

FIELD OF THE INVENTION

The invention relates to an oncolytic immunotherapeutic agent and to the use of the oncolytic immunotherapeutic agent in treating cancer.

BACKGROUND TO THE INVENTION

Viruses have a unique ability to enter cells at high efficiency. After entry into cells, viral genes are expressed and the virus replicates. This usually results in the death of the infected cell and the release of the antigenic components of the cell as the cell ruptures as it dies. As a result, virus mediated cell death tends to result in an immune response to these cellular components, including both those derived from the host cell and those encoded by or incorporated into the virus itself and enhanced due to the recognition by the host of so called damage associated molecular patterns (DAMPs) which aid in the activation of the immune response.

Viruses also engage with various mediators of the innate immune response as part of the host response to the recognition of a viral infection through e.g. toll-like receptors and cGAS/STING signalling and the recognition of pathogen associated molecular patterns (PAMPs) resulting in the activation of interferon responses and inflammation which are also immunogenic signals to the host. These immune responses may result in the immunogenic benefit to cancer patients such that immune responses to tumor antigens provide a systemic overall benefit resulting in the treatment of tumors which have not been infected with the virus, including micro-metastatic disease, and providing vaccination against relapse.

The combined direct ('oncolytic') effects of the virus, and immune responses against tumor antigens (including non-self 'neo-antigens', i.e. derived from the particular mutated genes in individual tumors) is termed 'oncolytic immunotherapy'.

Viruses may also be used as delivery vehicles ('vectors') to express heterologous genes inserted into the viral genome in infected cells. These properties make viruses useful for a variety of biotechnology and medical applications. For example, viruses expressing heterologous therapeutic genes may be used for gene therapy. In the context of oncolytic immunotherapy, delivered genes may include those encoding specific tumor antigens, genes intended to induce immune responses or increase the immunogenicity of antigens released following virus replication and cell death, genes intended to shape the immune response which is generated, genes to increase the general immune activation status of the tumor, or genes to increase the direct oncolytic properties (i.e. cytotoxic effects) of the virus. Importantly, viruses have the ability to deliver encoded molecules which are intended to help to initiate, enhance or shape the systemic anti-tumor immune response directly and selectively to tumors, which may have benefits of e.g. reduced toxicity or of focusing beneficial effects on tumors (including those not infected by the virus) rather than off-target effects on normal (i.e. non-cancerous) tissues as compared to the systemic administration of these same molecules or systemic administration of other molecules targeting the same pathways.

It has been demonstrated that a number of viruses including, for example, herpes simplex virus (HSV) have utility in the oncolytic treatment of cancer. HSV for use in the oncolytic treatment of cancer must be disabled such that it is no longer pathogenic, but can still enter into and kill tumor cells. A number of disabling mutations to HSV, including disruption of the genes encoding ICP34.5, ICP6, and/or thymidine kinase, have been identified which do not prevent the virus from replicating in culture or in tumor tissue in vivo, but which prevent significant replication in normal tissue. HSVs in which only the ICP34.5 genes have been disrupted replicate in many tumor cell types in vitro, and replicate selectively in tumor tissue, but not in surrounding tissue, in mouse tumor models. Clinical trials of ICP34.5 deleted, or ICP34.5 and ICP6 deleted, HSV have also shown safety and selective replication in tumor tissue in humans.

As discussed above, an oncolytic virus, including HSV, may also be used to deliver a therapeutic gene in the treatment of cancer. An ICP34.5 deleted virus of this type additionally deleted for ICP47 and encoding a heterologous gene for GM-CSF has also been tested in clinical trials, including a phase 3 trial in melanoma in which safety and efficacy in man was shown. GM-CSF is a pro-inflammatory cytokine which has multiple functions including the stimulation of monocytes to exit the circulation and migrate into tissue where they proliferate and mature into macrophages and dendritic cells. GM-CSF is important for the proliferation and maturation of antigen presenting cells, the activity of which is needed for the activation of an anti-tumor immune response. The trial data demonstrated that tumor responses could be seen in injected tumors, and to a lesser extent in uninjected tumors. Responses tended to be highly durable (months-years), and a survival benefit appeared to be achieved in responding patients. Each of these indicated engagement of the immune system in the treatment of cancer in addition to the direct oncolytic effect. However, this and other data with oncolytic viruses generally showed that not all tumors respond to treatment and not all patients achieve a survival advantage. Thus, improvements to the art of oncolytic therapy are clearly needed.

Recently it has been shown that oncolytic immunotherapy can result in additive or synergistic therapeutic effects in conjunction with immune checkpoint blockade (i.e. inhibition or 'antagonism' of immune checkpoint pathways, also termed immune co-inhibitory pathways). Checkpoint (immune inhibitory pathway) blockade is intended to block host immune inhibitory mechanisms which usually serve to prevent the occurrence of auto-immunity. However, in cancer patients these mechanisms can also serve to inhibit the induction of or block the potentially beneficial effects of any immune responses induced to tumors.

Systemic blockade of these pathways by agents targeting CTLA-4, PD-1 or PD-L1 have shown efficacy in a number of tumor types, including melanoma and lung cancer. However, unsurprisingly, based on the mechanism of action, off target toxicity can occur due to the induction of autoimmunity. Even so, these agents are sufficiently tolerable to provide considerable clinical utility. Other immune co-inhibitory pathway and related targets for which agents (mainly antibodies) are in development include LAG-3, TIM-3, VISTA, CSF1R, IDO, CEACAM1, CD47. Optimal clinical activity of these agents, for example PD1, PDL1, LAG-3, TIM-3, VISTA, CSF1R, IDO, CD47, CEACAM1, may require systemic administration or presence in all tumors due to the mechanism of action, i.e. including targeting of the interface of immune effector cells with tumors or other immune inhibitory mechanisms in/of tumors. In some cases, more localised presence in e.g. just some tumors or in some lymph nodes may also be optimally effective, for example agents targeting CTLA-4.

An alternative approach to increasing the anti-tumor immune response in cancer patients is to target (activate) immune co-stimulatory pathways. i.e. in contrast to inhibiting immune co-inhibitory pathways. These pathways send activating signals into T cells and other immune cells, usually resulting from the interaction of the relevant ligands on antigen presenting cells (APCs) and the relevant receptors on the surface of T cells and other immune cells. These signals, depending on the ligand/receptor, can result in the increased activation of T cells and/or APCs and/or NK cells and/or B cells, including particular sub-types, increased differentiation and proliferation of T cells and/or APCs and/or NK cells and/or B cells, including particular sub-types, or suppression of the activity of immune inhibitory T cells such as regulatory T cells. Activation of these pathways would therefore be expected to result in enhanced anti-tumor immune responses, but it might also be expected that systemic activation of these pathways, i.e. activation of immune responses generally rather than anti-tumor immune responses specifically or selectively, would result in considerable off target toxicity in non-tumor tissue, the degree of such off target toxicity depending on the particular immune co-stimulatory pathway being targeted. Nevertheless agents (mainly agonistic antibodies, or less frequently the soluble ligand to the receptor in question) targeting immune co-stimulatory pathways, including agents targeting GITR, 4-1-BB, OX40, CD40 or ICOS, and intended for systemic use (i.e. intravenous delivery) are in or have been proposed for clinical development.

For many of these approaches targeting immune co-inhibitory or co-inhibitory pathways to be successful, pre-existing immune responses to tumors are needed, i.e. so that a pre-existing immune response can be potentiated or a block to an anti-tumor immune response can be relieved. The presence of an inflamed tumor micro-environment, which is indicative of such an ongoing response, is also needed. Pre-existing immune responses to tumor neo-antigens appear to be particularly important for the activity of immune co-inhibitory pathway blockade and related drugs. Only some patients may have an ongoing immune response to tumor antigens including neoantigens and/or an inflamed tumor microenvironment, both of which are required for the optimal activity of these drugs. Therefore, oncolytic agents which can induce immune responses to tumor antigens, including neoantigens, and/or which can induce an inflamed tumor microenvironment are attractive for use in combination with immune co-inhibitory pathway blockade and immune potentiating drugs. This likely explains the promising combined anti-tumor effects of oncolytic agents and immune co-inhibitory pathway blockade in mice and humans that have so far been observed.

The above discussion demonstrates that there is still much scope for improving oncolytic agents and cancer therapies utilising oncolytic agents, anti-tumor immune responses and drugs which target immune co-inhibitory or co-stimulatory pathways.

SUMMARY OF THE INVENTION

The invention provides oncolytic viruses expressing GM-CSF and at least one molecule targeting an immune co-stimulatory pathway. GM-CSF aids in the induction of an inflammatory tumor micro-environment and stimulates the proliferation and maturation of antigen presenting cells, including dendritic cells, aiding the induction of an anti-tumor immune responses. These immune responses are amplified through activation of an immune co-stimulatory pathway or pathways using an immune co-stimulatory pathway activating molecule or molecules also delivered by the oncolytic virus.

The use of an oncolytic virus to deliver molecules targeting immune co-stimulatory pathways to tumors focuses the amplification of immune effects on anti-tumor immune responses, and reduces the amplification of immune responses to non-tumor antigens. Thus, immune cells in tumors and tumor draining lymph nodes are selectively engaged by the molecules activating immune co-stimulatory pathways rather than immune cells in general. This results in enhanced efficacy of immune co-stimulatory pathway activation and anti-tumor immune response amplification, and can also result in reduced off target toxicity. It is also important for focusing the effects of combined systemic immune co-inhibitory pathway blockade and immune co-stimulatory pathway activation on tumors, i.e. such that the amplified immune responses from which co-inhibitory blocks are released are antitumor immune responses rather than responses to non-tumor antigens.

The invention utilizes the fact that, when delivered by an oncolytic virus, the site of action of co-stimulatory pathway activation and of GM-CSF expression is in the tumor and/or tumor draining lymph node, but the results of such activation (an amplified systemic anti-tumor-immune response) are systemic. This targets tumors generally, and not only tumors to which the oncolytic virus has delivered the molecule or molecules targeting an immune co-stimulatory pathway or pathways and GM-CSF. Oncolytic viruses of the invention therefore provide improved treatment of cancer through the generation of improved tumor focused immune responses. The oncolytic virus of the invention also offers improved anti-tumor immune stimulating effects such that the immune-mediated effects on tumors which are not destroyed by oncolysis, including micro-metastatic disease, are enhanced, resulting in more effective destruction of these tumors, and more effective long term anti-tumor vaccination to prevent future relapse and improve overall survival.

Anti-tumor efficacy is improved when an oncolytic virus of the invention is used as a single agent and also when the virus is used in combination with other anti-cancer modalities, including chemotherapy, treatment with targeted agents, radiation and, in preferred embodiments, immune checkpoint blockade drugs (i.e. antagonists of an immune co-inhibitory pathway) and/or agonists of an immune co-stimulatory pathway.

Accordingly, the present invention provides an oncolytic virus comprising: (i) a GM-CSF-encoding gene; and (ii) an immune co-stimulatory pathway activating molecule or immune co-stimulatory pathway activating molecule-encoding gene. The virus may encode more than one immune co-stimulatory pathway activating molecule/gene.

The immune co-stimulatory pathway activating molecule is preferably GITRL, 4-1-BBL, OX40L, ICOSL or CD40L or a modified version of any thereof or a protein capable of blocking signaling through CTLA-4, for example an antibody which binds CTLA-4. Examples of modified versions include agonists of a co-stimulatory pathway that are secreted rather than being membrane bound, and/or agonists modified such that multimers of the protein are formed.

The virus may be a modified clinical isolate, such as a modified clinical isolate of a virus, wherein the clinical isolate kills two or more tumor cell lines more rapidly and/or at a lower dose in vitro than one or more reference clinical isolates of the same species of virus.

The virus is preferably a herpes simplex virus (HSV), such as HSV1. The HSV typically does not express functional ICP34.5 and/or functional TCP47 and/or expresses the US11 gene as an immediate early gene.

The invention also provides:
- a pharmaceutical composition comprising a virus of the invention and a pharmaceutically acceptable carrier or diluent;
- the virus of the invention for use in a method of treating the human or animal body by therapy;
- the virus of the invention for use in a method of treating cancer, wherein the method optionally comprises administering a further anti-cancer agent;
- a product of manufacture comprising a virus of the invention in a sterile vial, ampoule or syringe;
- a method of treating cancer, which comprises administering a therapeutically effective amount of a virus or a pharmaceutical composition of the invention to a patient in need thereof, wherein the method optionally comprises administering a further anti-cancer agent which is optionally an antagonist of an immune co-inhibitory pathway, or an agonist of an immune co-stimulatory pathway;
- use of a virus of the invention in the manufacture of a medicament for use in a method of treating cancer, wherein the method optionally comprises administering a further anti-cancer agent which is optionally an antagonist of an immune co-inhibitory pathway, or an agonist of an immune co-stimulatory pathway;
- a method of treating cancer, which comprises administering a therapeutically effective amount of an oncolytic virus, an inhibitor of the indoleamine 2,3-dioxygenase (IDO) pathway and a further antagonist of an immune co-inhibitory pathway, or an agonist of an immune co-stimulatory pathway to a patient in need thereof.

BRIEF DESCRIPTION OF THE FIGURES

FIGS. 11A-11C shows the antitumor effects of Virus 16 in Balb/c mice harboring mouse CT26 tumors in the left and right flanks. Groups of 10 mice were then treated with: Vehicle (3 injections into right flank tumors every other day); 5×10 exp 6 pfu of Virus 16 (mRP1) injected in the right flank tumor every other day; anti-mouse PD1 alone (10 mg/kg i.p. every three days, BioXCell clone RMP1-14); anti-mouse CTLA-4 (3 mg/kg i.p every three days, BioXCell clone 9D9); anti-mouse PD1 together with Virus 16; anti-mouse CTLA4 together with Virus 16; 1-methyl trypotophan (I-MT; IDO inhibitor (5 mg/ml in drinking water)); anti-mouse PD1 together with 1-methyl trypotophan; or anti-mouse PD1 together with 1-methyl trypotophan and Virus 16. Effects on tumor size were observed for a further 30 days. Greater tumor reduction was seen in animals treated with combinations of virus and checkpoint bockade than with the single treatment groups. FIG. 11A shows that using Virus 16 and anti-PD1 in combination has a better anti-tumor effect than using either anti-PD1 or the virus alone. FIG. 11B shows that the anti-tumor effect of Virus 16 in combination with anti-CTLA-4 was better than the anti-tumor effect of either Virus 16 or anti-CTLA-4 alone. FIG. 11C shows that enhanced tumor reduction was observed using Virus 16 together with both anti-PD1 and IDO inhibition as compared to anti-PD1 and 1-MT inhibition in the absence of the virus.

FIGS. 12A-12D shows the enhanced anti-tumor activity of Virus 16 in combination with immune checkpoint blockade in mouse A20 tumors in both flanks of Balb/c mice as compared to either virus alone or checkpoint blockade alone (anti-PD1).

BRIEF DESCRIPTION OF THE SEQUENCE LISTING

Figure 1:
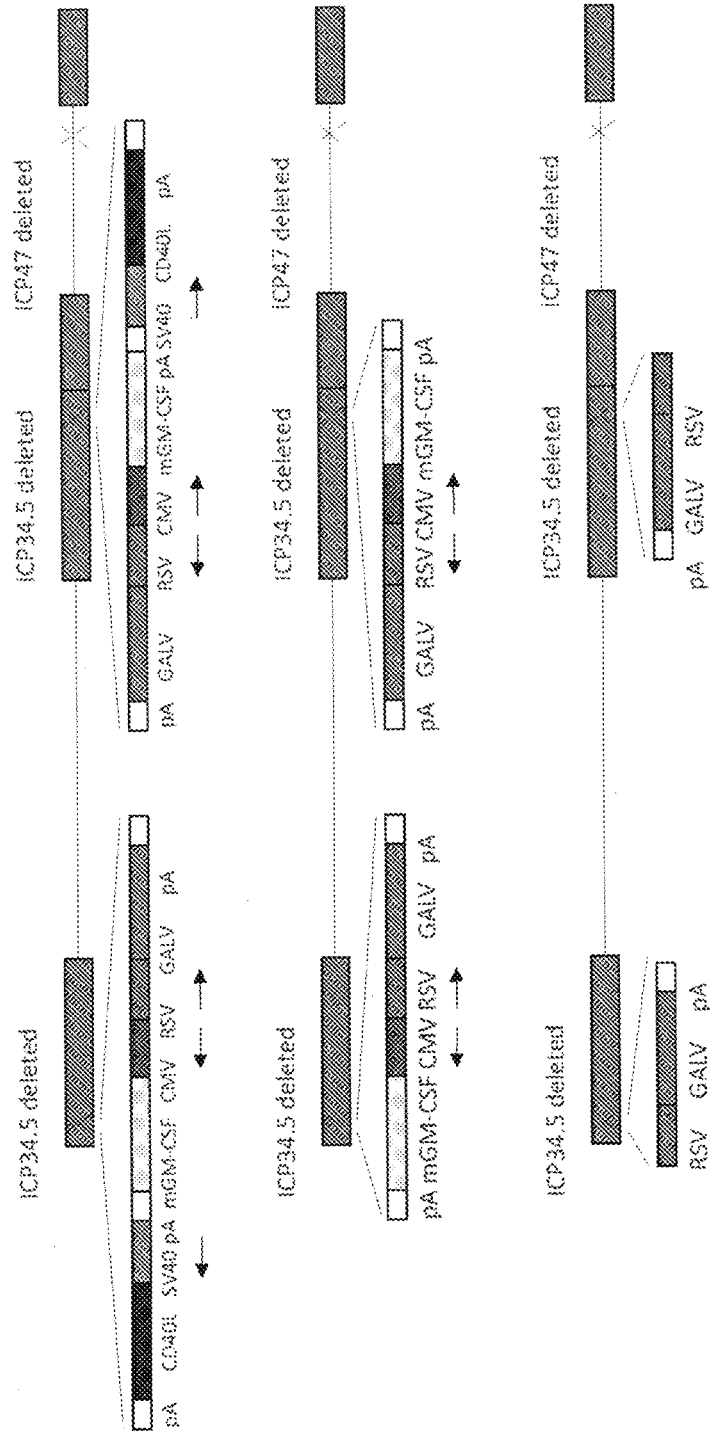
FIG. 1 depicts the structure of an exemplary virus of the invention that comprises a gene encoding GM-CSF and a gene encoding CD40L.

SEQ ID NO: 1 is the nucleotide sequence of mouse GM-CSF.
SEQ ID NO: 2 is the nucleotide sequence of a codon optimized version of mouse GM-CSF.
SEQ ID NO: 3 is the nucleotide sequence of human GM-CSF.
SEQ ID NO: 4 is the nucleotide sequence of a codon optimized version of human GM-CSF.
SEQ ID NO: 5 is the amino acid sequence of mouse GM-CSF.
SEQ ID NO: 6 is the amino acid sequence of human GM-CSF.
SEQ ID NO: 7 is the nucleotide sequence of GALV-R-.
SEQ ID NO: 8 is the nucleotide sequence of a codon optimized version of GALV-R-(the first three nucleotides are optional) SEQ ID NO: 9 is the amino acid sequence of GALV-R-.
SEQ ID NO: 10 is the nucleotide sequence of a codon optimized version of a human membrane bound version of CD40L.
SEQ ID NO: 11 is the amino acid sequence of a human membrane bound version of CD40L.
SEQ ID NO: 12 is the nucleotide sequence of a codon optimized version of a multimeric secreted version of human CD40L.
SEQ ID NO: 13 is the amino acid sequence of a multimeric secreted version of human CD40L.
SEQ ID NO: 14 is the nucleotide sequence of a codon optimized version of a multimeric secreted version of mouse CD40L.
SEQ ID NO: 15 is the amino acid sequence of a multimeric secreted version of mouse CD40L.
SEQ ID NO: 16 is a codon optimized version of the nucleotide sequence of wild-type human CD40L.
SEQ ID NO: 17 is the amino acid sequence of wild-type human CD40L.
SEQ ID NO: 18 is a codon optimized version of the nucleotide sequence of wild-type mouse CD40L.
SEQ ID NO: 19 is the amino acid sequence of wild-type mouse CD40L.
SEQ ID NO: 20 is the nucleotide sequence of a codon optimized version of murine 4-1BBL.
SEQ ID NO: 21 is the nucleotide sequence of a codon optimized version of human 4-1BBL.
SEQ ID NO: 22 is the nucleotide sequence of a codon optimized version of secreted mouse 4-1BBL.
SEQ ID NO: 23 is the nucleotide sequence of a codon optimized version of human secreted 4-1BBL.
SEQ ID NO: 24 is the nucleotide sequence of a codon optimized version of murine GITRL.
SEQ ID NO: 25 is the nucleotide sequence of a codon optimized version of human GITRL.
SEQ ID NO: 26 is the nucleotide sequence of a codon optimized version of secreted murine GITRL.
SEQ ID NO: 27 is the nucleotide sequence of a codon optimized version of secreted human GITRL.
SEQ ID NO: 28 is the nucleotide sequence of a codon optimized version of murine OX40L.
SEQ ID NO: 29 is the nucleotide sequence of a codon optimized version of human OX40L.
SEQ ID NO: 30 is the nucleotide sequence of a codon optimized version of secreted murine OX40L.
SEQ ID NO: 31 is the nucleotide sequence of a codon optimized version of secreted human OX40L.
SEQ ID NO: 32 is the nucleotide sequence of a codon optimized version of murine ICOSL.
SEQ ID NO: 33 is the nucleotide sequence of a codon optimized version of human ICOSL.
SEQ ID NO: 34 is the nucleotide sequence of a murine scFv CTLA-4 antibody. The first six and last eight nucleotides are restriction sites added for cloning purposes.
SEQ ID NO: 35 is the nucleotide sequence of a murine scFv CTLA-4 antibody.
The first six and last eight nucleotides are restriction sites added for cloning purposes.
SEQ ID NO: 36 is the nucleotide sequence of the CMV promoter.
SEQ ID NO: 37 is the nucleotide sequence of the RSV promoter.

SEQ ID NO: 38 is the nucleotide sequence of BGH polyA.

SEQ ID NO: 39 is the nucleotide sequence of SV40 late polyA.

SEQ ID NO: 40 is the nucleotide sequence of the SV40 enhancer promoter.

SEQ ID NO: 41 is the nucleotide sequence of rabbit beta-globulin (RBG) polyA.

SEQ ID NO: 42 is the nucleotide sequence of GFP.

SEQ ID NO: 43 is the nucleotide sequence of the MoMuLV LTR promoter.

SEQ ID NO: 44 is the nucleotide sequence of the EF1a promoter.

SEQ ID NO: 45 is the nucleotide sequence of HGH polyA.

DETAILED DESCRIPTION OF THE INVENTION

Oncolytic Virus

The virus of the invention is oncolytic. An oncolytic virus is a virus that infects and replicates in tumor cells, such that the tumor cells are killed. Therefore, the virus of the invention is replication competent. Preferably, the virus is selectively replication competent in tumor tissue. A virus is selectively replication competent in tumor tissue if it replicates more effectively in tumor tissue than in non-tumor tissue. The ability of a virus to replicate in different tissue types can be determined using standard techniques in the art.

The virus of the invention may be any virus which has these properties, including a herpes virus, pox virus, adenovirus, retrovirus, rhabdovirus, paramyxovirus or reovirus, or any species or strain within these larger groups. Viruses of the invention may be wild type (i.e. unaltered from the parental virus species), or with gene disruptions or gene additions. Which of these is the case will depend on the virus species to be used. Preferably the virus is a species of herpes virus, more preferably a strain of HSV, including strains of HSV1 and HSV2, and is most preferably a strain of HSV1. In particularly preferred embodiments the virus of the invention is based on a clinical isolate of the virus species to be used. The clinical isolate may have been selected on the basis of it having particular advantageous properties for the treatment of cancer.

The clinical isolate may have surprisingly good anti-tumor effects compared to other strains of the same virus isolated from other patients, wherein a patient is an individual harbouring the virus species to be tested. The virus strains used for comparison to identify viruses of the invention may be isolated from a patient or an otherwise healthy (i.e. other than harboring the virus species to be tested) volunteer, preferably an otherwise healthy volunteer. HSV1 strains used to identify a virus of the invention are typically isolated from cold sores of individuals harboring HSV1, typically by taking a swab using e.g. Virocult (Sigma) brand swab/container containing transport media followed by transport to the facility to be used for further testing.

After isolation of viruses to be compared from individuals, stocks of the viruses are typically prepared, for example by growing the isolated viruses on BHK or vero cells. Preferably, this is done following no more than 3 cycles of freeze thaw between taking the sample and it being grown on, for example, BHK or vero cells to prepare the virus stock for further use. More preferably the virus sample has undergone 2 or less than 2 cycles of freeze thaw prior to preparation of the stock for further use, more preferably one cycle of freeze thaw, most preferably no cycles of freeze thaw. Lysates from the cell lines infected with the viruses prepared in this way after isolation are compared, typically by testing for the ability of the virus to kill tumor cell lines in vitro. Alternatively, the viral stocks may be stored under suitable conditions, for example by freezing, prior to testing. Viruses of the invention have surprisingly good anti-tumor effects compared to other strains of the same virus isolated from other individuals, preferably when compared to those isolated from >5 individuals, more preferably >10 other individuals, most preferably >20 other individuals.

The stocks of the clinical isolates identified for modification to produce viruses of the invention (i.e. having surprisingly good properties for the killing of tumor cells as compared to other viral strains to which they were compared) may be stored under suitable conditions, before or after modification, and used to generate further stocks as appropriate.

A clinical isolate is a strain of a virus species which has been isolated from its natural host. The clinical isolate has preferably been isolated for the purposes of testing and comparing the clinical isolate with other clinical isolates of that virus species for a desired property, in the case of viruses of the invention that being the ability to kill human tumor cells. Clinical isolates which may be used for comparison also include those from clinical samples present in clinical repositories, i.e. previously collected for clinical diagnostic or other purposes. In either case the clinical isolates used for comparison and identification of viruses of the invention will preferably have undergone minimal culture in vitro prior to being tested for the desired property, preferably having only undergone sufficient culture to enable generation of sufficient stocks for comparative testing purposes. As such, the viruses used for comparison to identify viruses of the invention may also include deposited strains, wherein the deposited strain has been isolated from a patient, preferably an HSV1 strain isolated from the cold sore of a patient.

The virus may be a modified clinical isolate, wherein the clinical isolate kills two or more tumor cell lines more rapidly and/or at a lower dose in vitro than one or more reference clinical isolate of the same species of virus. Typically, the clinical isolate will kill two or more tumor cell lines within 72 hours, preferably within 48 hours, more preferably within 24 hours, of infection at multiplicities of infection (MOI) of less than or equal to 0.1, preferably less than or equal to an MOI of 0.01, more preferably less than or equal to an MOI of 0.001. Preferably the clinical isolate will kill a broad range of tumor cell lines, such as 2, 3, 4, 5, 6, 7, 8, 9, 10 or, for example, all of the following human tumor cell lines: U87MG (glioma), HT29 (colorectal), LNCaP (prostate), MDA-MB-231 (breast), SK-MEL-28 (melanoma), Fadu (squamous cell carcinoma), MCF7 (breast), A549 (lung), MIAPACA-2 (pancreas), CAPAN-1 (pancreas), HT1080 (fibrosarcoma).

Thus, the virus of the invention may be capable of killing cells from two or more, such as 3, 4, 5, 6, 7 or more, different types of tumor such as two or more, such as 3, 4, 5, 6, 7 or more, solid tumors, including but not limited to colorectal tumor cells, prostate tumor cells, breast tumor cells, ovarian tumor cells, melanoma cells, squamous cell carcinoma cells, lung tumor cells, pancreatic tumor cells, sarcoma cells and/or fibrosarcoma cells.

Tumor cell line killing can be determined by any suitable method. Typically, a sample is first isolated from a patient, preferably, in the case of HSV1, from a cold sore, is used to infect BHK cells, or another suitable cell line such as vero cells. Positive samples are typically identified by the presence of a cytopathic effect (CPE) 24-72 hours post infection, such as 48 hours post infection, and confirmed to be the target viral species by, for example, immunohistochemistry or PCR. Viral stocks are then generated from the positive samples. A sample from the viral stock is typically tested and compared to other samples generated in the same way using swabs from different patients. Testing may be carried out by determining the level of CPE achieved at a range of multiplicity of infection (MOI) and at various times post infection.

For example, cell lines at 80% confluency may be infected with the viral sample at MOI of 1, 0.1, 0.01 and 0.001 and duplicate plates incubated for 24 and 48 hours at 37° C., 5% $CO_2$ prior to determination of the extent of viral cell killing. This may be determined by, for example, fixing the cells with glutaraldehyde and staining with crystal violet using standard methods. The level of cell lysis may then be assessed by standard methods such as gross observation, microscopy (cell counts) and photography. The method may be repeated with the cells being incubated for shorter time periods, such as 8, 12 or 16 hours, or longer time periods, such as 72 hours, before cell killing is determined, or at additional MOIs such as 0.0001 or less.

Growth curve experiments may also be conducted to assess the abilities of different clinical isolates to replicate in tumor cell lines in vitro. For example, cell lines at 80% confluency may be infected with the viral sample at MOI of 1, 0.1, 0.01 and 0.001 are incubated at 37° C., 5% $CO_2$ and the cells lysed, typically by freeze/thawing, at 0, 8, 16, 24 and 48 hours post infection prior to determination of the extent of viral cell killing. This may be determined by, for example, assessing viral titres by a standard plaque assay.

A clinical isolate of the invention can kill infected tumor cell lines more rapidly and/or at a lower MOI than the other clinical isolates to which it is compared, preferably 2, 3, 4, 5 or 10 or more, other clinical isolates of the same virus species. The clinical isolate of the invention typically kills a 10%, 25% or 50% greater proportion of the tumor cells present at a particular MOI and time point than at least one, preferably 2, 3, 4, 5 or 10 or more, other clinical isolates of the same virus type at the same MOI and time point to which it was compared. The clinical isolate of the invention typically kills the same or a greater proportion of tumor cells at a MOI that is half or less than half that of the MOI at which one or more, preferably 2, 3, 4, 5,10 or 15 or more, other clinical isolates of the same virus species used for the comparison at the same time point, typically at 12, 24 and/or 48 hours, kills the same proportion of tumor cells. Preferably, a clinical isolate of the invention typically kills the same or a greater proportion of tumor cells at a MOI that is 5 or 10 times lower than the MOI at which one or more, preferably 2, 3, 4, 5, 10 or 15 or more, other clinical isolates of the same virus used for the comparison at the same time point, typically at 12, 24 and/or 48 hours kills the same proportion of tumor cells. The improved tumor cell killing abilities of a virus of the invention are typically achieved compared to at least 50%, 75% or 90% of the other clinical isolates of the same viral species used for the comparison. The virus is preferably compared to at least 4 other virus strains, such as, for example, 7, 9, 19, 39 or 49 other virus strains of the same species.

The isolated strains may be tested in batches, for example of 4-8 viral strains at a time, on, for example, 4-8 of the tumor cell lines at a time. For each batch of experiments, the degree of killing achieved is ranked on each cell line for the best (i.e. least surviving cells at each time point/MOI) to the worst (i.e. most surviving cells for each time point/MOI) for the viruses being compared in that experiment. The virus strains from each experiment which perform the best across the range of tumor cell line tested (i.e. that consistently ranked as one of the best at killing the cell lines) may then be compared head to head in further experiments using other clinical isolates and/ore other tumor cell lines to identify the best virus strains in the total of, for example, >20 virus strains sampled. Those ranked as the best overall are the viruses of the invention.

In a preferred embodiment, the virus of the invention is a strain selected from:
strain RH018A having the provisional accession number ECCAC 16121904;
strain RH004A having the provisional accession number ECCAC 16121902;
strain RH031A having the provisional accession number ECCAC 16121907;
strain RH040B having the provisional accession number ECCAC 16121908;
strain RH015A having the provisional accession number ECCAC 16121903;
strain RH021A having the provisional accession number ECCAC 16121905;
strain RH023A having the provisional accession number ECCAC 16121906; and strain RH047A having the provisional accession number ECCAC 16121909.

More preferably, the virus of the invention is a strain selected from:
strain RH018A having the provisional accession number ECCAC 16121904;
strain RH004A having the provisional accession number ECCAC 16121902;
strain RH031 A having the provisional accession number ECCAC 16121907;
strain RH040B having the provisional accession number ECCAC 16121908; and
strain RH015A having the provisional accession number ECCAC 16121903;

Most preferably, the virus of the invention is strain RH018A having the accession number EACC 16121904.

An HSV of the invention is capable of replicating selectively in tumors, such as human tumors. Typically, the HSV replicates efficiently in target tumors but does not replicate efficiently in non-tumor tissue. This HSV may comprise one or more mutations in one or more viral genes that inhibit replication in normal tissue but still allow replication in tumors. The mutation may, for example, be a mutation that prevents the expression of functional ICP34.5, ICP6 and/or thymidine kinase by the HSV.

In one preferred embodiment, the ICP34.5-encoding genes are mutated to confer selective oncolytic activity on the HSV. Mutations of the ICP34.5-encoding genes that prevent the expression of functional ICP34.5 are described in Chou et al. (1990) Science 250:1262-1266, Maclean et al. (1991) J. Gen. Virol. 72:631-639 and Liu et al. (2003) Gene Therapy 10:292-303, which are incorporated herein by reference. The ICP6-encoding gene and/or thymidine kinase-encoding gene may also be inactivated, as may other genes provided that such inactivation does not prevent the virus infecting or replicating in tumors.

The HSV may contain a further mutation or mutations which enhance replication of the HSV in tumors. The resulting enhancement of viral replication in tumors not only results in improved direct 'oncolytic' tumor cell killing by the virus, but also enhances the level of heterologous (i.e. a gene inserted into the virus, in the case of viruses of the invention genes encoding GM-CSF and an immune costimulatory pathway activating molecule(s)) gene expression and increases the amount of tumor antigen released as tumor cells die, both of which may also improve the immunogenic properties of the therapy for the treatment of cancer. For example, in a preferred embodiment of the invention, deletion of the ICP47-encoding gene in a manner that places the US11 gene under the control of the immediate early promoter that normally controls expression of the ICP47 encoding gene leads to enhanced replication in tumors (see Liu et al., 2003, which is incorporated herein by reference).

Other mutations that place the US11 coding sequence, which is an HSV late gene, under the control of a promoter that is not dependent on viral replication may also be introduced into a virus of the invention. Such mutations allow expression of US11 before HSV replication occurs and enhance viral replication in tumors. In particular, such mutations enhance replication of an HSV lacking functional ICP34.5-encoding genes.

Accordingly, in one embodiment the HSV of the invention comprises a US11 gene operably linked to a promoter, wherein the activity of the promoter is not dependent on viral replication. The promoter may be an immediate early (IE) promoter or a non-HSV promoter which is active in mammalian, preferably human, tumor cells. The promoter may, for example, be a eukaryotic promoter, such as a promoter derived from the genome of a mammal, preferably a human. The promoter may be a ubiquitous promoter (such as a promoter of β-actin or tubulin) or a cell-specific promoter, such as tumor-specific promoter. The promoter may be a viral promoter, such as the Moloney murine leukaemia virus long terminal repeat (MMLV LTR) promoter or the human or mouse cytomegalovirus (CMV) IE promoter. HSV immediate early (IE) promoters are well known in the art. The HSV1E promoter may be the promoter driving expression of ICP0, ICP4, ICP22, ICP27 or ICP47.

The genes referred to above the functional inactivation of which provides the property of tumor selectivity to the virus may be rendered functionally inactive by any suitable method, for example by deletion or substitution of all or part of the gene and/or control sequence of the gene or by insertion of one or more nucleic acids into or in place of the gene and/or the control sequence of the gene. For example, homologous recombination methods, which are standard in the art, may be used to generate the virus of the invention. Alternatively bacterial artificial chromosome (BAC)-based approaches may be used.

As used herein, the term "gene" is intended to mean the nucleotide sequence encoding a protein, i.e. the coding sequence of the gene. The various genes referred to above may be rendered non-functional by mutating the gene itself or the control sequences flanking the gene, for example the promoter sequence. Deletions may remove one or more portions of the gene, the entire gene or the entire gene and all or some of the control sequences. For example, deletion of only one nucleotide within the gene may be made, resulting in a frame shift. However, a larger deletion may be made, for example at least about 25%, more preferably at least about 50% of the total coding and/or non-coding sequence. In one preferred embodiment, the gene being rendered functionally inactive is deleted. For example, the entire gene and optionally some of the flanking sequences may be removed from the virus. Where two or more copies of the gene are present in the viral genome both copies of the gene are rendered functionally inactive.

A gene may be inactivated by substituting other sequences, for example by substituting all or part of the endogenous gene with a heterologous gene and optionally a promoter sequence. Where no promoter sequence is substituted, the heterologous gene may be inserted such that it is controlled by the promoter of the gene being rendered non-functional. In an HSV of the invention it is preferred that the ICP34.5 encoding-genes are rendered non-functional by the insertion of a heterologous gene or genes and a promoter sequence or sequences operably linked thereto, and optionally other regulatory elements such as polyadenylation sequences, into each the ICP34.5-encoding gene loci.

A virus of the invention is used to express GM-CSF and an immune co-stimulatory pathway activating molecule in tumors. This is typically achieved by inserting a heterologous gene encoding GM-CSF and a heterologous gene encoding the immune co-stimulatory pathway activating molecule in the genome of a selectively replication competent virus wherein each gene is under the control of a promoter sequence. As replication of such a virus will occur selectively in tumor tissue, expression of the GM-CSF and the immune co-stimulatory activating protein by the virus is also enhanced in tumor tissue as compared to non-tumor tissue in the body. Enhanced expression occurs where expression is greater in tumors as compared to other tissues of the body. Proteins expressed by the oncolytic virus would also be expected to be present in oncolytic virus-infected tumor draining lymph nodes, including due to trafficking of expressed protein and of virus in and on antigen presenting cells from the tumor. Accordingly, the invention provides benefits of expression of both GM-CSF and an immune co-stimulatory pathway activating molecule selectively in tumors and tumor draining lymph nodes combined with the anti-tumor effect provided by oncolytic virus replication.

The virus of the invention comprises GM-CSF. The sequence of the gene encoding GM-CSF may be codon optimized so as to increase expression levels of the respective proteins in target cells as compared to if the unaltered sequence is used.

The virus of the invention comprises one or more immune co-stimulatory pathway activating molecules and/or one or more genes encoding an immune co-stimulatory pathway activating molecule. Immune co-stimulatory pathway activating molecules include proteins and nucleic acid molecules (e.g. aptamer sequences). Examples of immune co-stimulatory pathway activating molecules include CD40 ligand, GITR ligand, 4-1-BB ligand, OX40 ligand, ICOS ligand, flt3 ligand, TL1A, CD30 ligand, CD70 and single chain antibodies targeting the respective receptors for these molecules (CD40, GITR, 4-1-BB, OX40, ICOS, flt3, DR3, CD30, CD27). The CD40L, GITRL, 4-1-BBL, OX40L, ICOSL, ft3L, TLIA, CD30L or CD70L may be a modified version of any thereof, such as a soluble version.

Activators of immune co-stimulatory pathways include mutant or wild type, soluble, secreted and/or membrane bound ligands, and agonistic antibodies including single chain antibodies. Viruses of the invention preferably encode one or more of CD40L, ICOSL, 4-1-BBL, GITRL or OX40L.

The inhibitor of a co-inhibitory pathway may be a CTLA-4 inhibitor. The CTLA-4 inhibitor is typically a molecule such as a peptide or protein that binds to CTLA-4 and reduces or blocks signaling through CTLA-4, such as by reducing activation by B7. By reducing CTLA-4 signalling, the inhibitor reduces or removes the block of immune stimulatory pathways by CTLA-4.

The CTLA-4 inhibitor is preferably an antibody or an antigen binding fragment thereof. The term "antibody" as referred to herein includes whole antibodies and any antigen binding fragment (i.e., "antigen-binding portion") or single chains thereof. An antibody refers to a glycoprotein comprising at least two heavy (H) chains and two light (kappa) (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (C1q) of the classical complement system.

The antibody is typically a monoclonal antibody. The antibody may be a chimeric antibody. The antibody is preferably a humanised antibody and is more preferably a human antibody.

The term "antigen-binding fragment" of an antibody refers to one or more fragments of an antibody that retain the ability to specifically bind to CTLA-4. The antigen-binding fragment also retains the ability to inhibit CTLA-4 and hence to reduce or remove the CTLA-4 blockade of a stimulatory immune response. Examples of suitable fragments include a Fab fragment, a F(ab')$_2$ fragment, a Fab' fragment, a Fd fragment, a Fv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody. In a preferred embodiment, the antibody is an scFv. Examples of suitable scFv molecules are disclosed in, for example, WO2007/123737 and WO2014/066532, which are incorporated herein by reference. The scFv may be encoded by the nucleotide sequence shown in SEQ ID NO: 34 the nucleotide sequence shown in SEQ ID NO: 35.

Viruses of the invention may encode one or more immune co-stimulatory pathway activating molecules, preferably 1, 2, 3 or 4 immune co-stimulatory pathway activating molecules, more preferably 1 or 2 immune co-stimulatory pathway activating molecules.

For example, the virus may comprise genes encoding:
CD40L and one or more of ICOSL, 4-1-BBL, GITRL, OX40L and a CTLA-4 inhibitor;
ICOSL and one or more of CD40L, 4-1-BBL, GITRL, OX40L and a CTLA-4 inhibitor;
4-1-BBL and one or more of CD40L, ICOSL, GITRL, OX40L and a CTLA-4 inhibitor;
GITRL and one or more of CD40L, ICOSL, 4-1-BBL, OX40L and a CTLA-4 inhibitor;
OX40L and one or more of CD40L, ICOSL, 4-1-BBL, GITRL and a CTLA-4 inhibitor;
a CTLA-4 inhibitor and one or more of CD40L, ICOSL, 4-1-BBL, GITRL and OX40L.

The sequence of the gene encoding the immune co-stimulatory activating molecule may be codon optimized so as to increase expression levels of the respective protein(s) in target cells as compared to if the unaltered sequence is used.

The virus of the invention may comprise one or more further heterologous genes in addition to GM-CSF and an immune co-stimulatory pathway activating molecule, including, in a preferred embodiment, a fusogenic protein such as GALVR-.

The fusogenic protein may be any heterologous protein capable of promoting fusion of a cell infected with the virus of the invention to another cell. A fusogenic protein, preferably a wild type or modified viral glycoprotein (i.e. modified to increase its fusogenic properties), is a protein which is capable in inducing the cell to cell fusion (syncitia formation) of cells in which it is expressed. Examples of fusogenic glycoproteins include VSV-G, syncitin-1 (from human endogenous retrovirus-W (HERV-W)) or syncitin-2 (from HERVFRDE1), paramyxovirus SV5-F, measles virus-H, measles virus-F, RSV-F, the glycoprotein from a retrovirus or lentivirus, such as gibbon ape leukemia virus (GALV), murine leukemia virus (MLV), Mason-Pfizer monkey virus (MPMV) and equine infectious anemia virus (EIAV) with the R transmembrane peptide removed (R-versions). In a preferred embodiment the fusogenic protein is from GALV and has the R- peptide removed (GALV-R-).

The virus of the invention may optionally comprise multiple copies of the fusogenic protein-encoding gene, preferably 1 or 2 copies. The virus may comprise two or more different fusogenic proteins, including any of the fusogenic proteins listed above.

The fusogenic protein or proteins optionally expressed by a virus of the invention may be identical to a naturally occurring protein, or may be a modified protein.

The fusogenic protein-encoding gene (fusogenic gene) may have a naturally occurring nucleic acid sequence or a modified sequence. The sequence of the fusogenic gene may, for example, be modified to increase the fusogenic properties of the encoded protein, or to provide codon optimisation and therefore increase the efficiency of expression of the encoded protein.

The invention also provides a virus, such as a pox virus or a HSV, preferably HSV1, which expresses at least three heterologous genes, wherein each of the three heterologous genes is driven by a different promoter selected from the CMV promoter, the RSV promoter, the EF1a promoter, the SV40 promoter and a retroviral LTR promoter. The virus may, for example, express four heterologous genes, wherein each of the four heterologous genes is driven by a different promoter selected from the CMV promoter, the RSV promoter, the EF1a promoter, the SV40 promoter and a retroviral LTR promoter. The retroviral LTR is preferably from MMLV (SEQ ID NO:43), also known as MoMuLV. The heterologous genes may be terminated by poly adenylation sequences. The poly adenylation sequences may be the same or different. Preferably each heterologous gene is terminated by a different poly adenylation sequence, which is preferably selected from the BGH, SV40, HGH and RBG poly adenylation sequences.

The invention also provides a virus, such as a pox virus or a HSV, preferably HSV1, which expresses at least three heterologous genes, wherein each of the three heterologous genes is terminated by a different poly adenylation sequence selected from the BGH, SV40, HGH and RBG poly adenylation sequences. The virus may, for example, express four heterologous genes terminated by each of the BGH, SV40, HGH and RBG poly adenylation sequences, respectively.

Production of Virus

Viruses of the invention are constructed using methods well known in the art. For example plasmids (for smaller viruses and single and multiple genome component RNA viruses) or BACs (for larger DNA viruses including herpes viruses) encoding the viral genome to be packaged, including the genes encoding the fusogenic and immune stimulating molecules under appropriate regulatory control, can be constructed by standard molecular biology techniques and transfected into permissive cells from which recombinant viruses can be recovered.

Alternatively, in a preferred embodiment plasmids containing DNA regions flanking the intended site of insertion can be constructed, and then co-transfected into permissive cells with viral genomic DNA such that homologous recombination between the target insertion site flanking regions in the plasmid and the same regions in the parental virus occur. Recombinant viruses can then be selected and purified through the loss or addition of a function inserted or deleted by the plasmid used for modification, e.g. insertion or deletion of a marker gene such as GFP or lacZ from the parental virus at the intended insertion site. In a most preferred embodiment the insertion site is the ICP34.5 locus of HSV, and therefore the plasmid used for manipulation contains HSV sequences flanking this insertion site, between which are an expression cassette encoding GM-CSF and the immune co-stimulatory pathway activating molecule. In this case, the parental virus may contain a cassette encoding GFP in place of ICP34.5 and recombinant virus plaques are selected through the loss of expression of GFP. In a most preferred embodiment the US11 gene of HSV is also expressed as an IE gene. This may be accomplished through deletion of the ICP47-encoding region, or by other means.

The GM-CSF encoding sequences and immune co-stimulatory pathway activating molecule encoding sequences are inserted into the viral genome under appropriate regulatory control. This may be under the regulatory control of natural promoters of the virus species of the invention used, depending on the species and insertion site, or preferably under the control of heterologous promoters. Suitable heterologous promoters include mammalian promoters, such as the IEF2a promoter or the actin promoter. More preferred are strong viral promoters such as the CMV IE promoter, the RSV LTR, the MMLV LTR, other retroviral LTR promoters, or promoters derived from SV40. Preferably each exogenous gene (e.g. encoding the GM-CSF and immune co-stimulatory pathway activating molecule) will be under separate promoter control, but may also be expressed from a single RNA transcript, for example through insertion of an internal ribosome entry sites (IRES) between protein coding sequences. RNA derived from each promoter is typically terminated using a polyadenylation sequence (e.g. mammalian sequences such as the bovine growth hormone (BGH) poly A sequence, synthetic polyadenylation sequences, the rabbit betaglobin polyadenylation sequence, or viral sequences such as the SV40 early or late polyadenylation sequence).

Pharmaceutical Compositions

The invention provides a pharmaceutical composition comprising the virus and a pharmaceutically acceptable carrier or diluent. Suitable carriers and diluents include isotonic saline solutions, for example phosphate-buffered saline. The composition may further comprise other constituents such as sugars or proteins to improve properties such as stability of the product. Alternatively a lyophilized formulation may be used, which is reconstituted in a pharmaceutically acceptable carrier or diluent before use.

The choice of carrier, if required, is frequently a function of the route of delivery of the composition. Within this invention, compositions may be formulated for any suitable route and means of administration. Pharmaceutically acceptable carriers or diluents are those used in compositions suitable for intra-tumoral administration, intravenous/intraarterial administration, administration into the brain or administration into a body cavity (e.g. bladder, pleural cavity or by intraperitoneal administration). The composition may be administered in any suitable form, preferably as a liquid.

The present invention also provides a product of manufacture comprising a virus of the invention in a sterile vial, ampoule or syringe.

Medical Uses/Methods of Treatment

The invention provides the virus of the invention for use in the treatment of the human or animal body by therapy, particularly for use in a method of treating cancer. The cancer is typically in a mammal, preferably in a human. The virus kills infected tumour cells by lysis and by causing infected tumor cells to fuse with one another. The virus of the invention also elicits a systemic anti-tumor immune response, augmented through the expression of GM-CSF and the immune co-stimulatory pathway activating molecule, which also kills cancer cells.

The invention also provides a method of treating cancer, the method comprising administering a therapeutically effective amount of the virus of the invention to an individual in need thereof.

The invention additionally provides the use of the virus of the invention in the manufacture of a medicament for treating cancer.

The virus of the invention is particularly useful in treating any solid tumor including any adenocarcinoma, carcinoma, melanoma or sarcoma. For example, the virus of the invention is useful in treating head and neck, prostate, breast, ovarian, lung, liver, endometrial, bladder, gall bladder, pancreas, colon, kidney, stomach/gastric, esophageal, or cervical cancers, mesothelioma, melanoma or other skin cancer, lymphoma, glioma or other cancer of the nervous system, or sarcomas such as soft tissue sarcoma.

The virus of the invention may be used to treat malignant tumors, including tumors that have metastasised from the site of the original tumor. In this embodiment, the virus may be administered to the primary tumor or to one or more secondary tumors.

The virus of the invention may be administered in combination with other therapeutic agents, including chemotherapy, targeted therapy, immunotherapy (including immune checkpoint blockade, i.e. administration of one or more antagonist of an immune co-inhibitory pathway, and/or one or more agonist of an immune co-stimulatory pathway) and/or in combination with radiotherapy and/or in combination with any combination of these. The therapeutic agent is preferably an anti-cancer agent.

The virus of the invention may be administered in combination with a second virus, such as a second oncolytic virus.

For example, the therapeutic agent may comprise an immunogen (including a recombinant or naturally occurring antigen, including such an antigen or combination of antigens delivered as DNA or RNA in which it/they are encoded), to further stimulate an immune response, such as a cellular or humoral immune response, to tumor cells, particularly tumor neoantigens. The therapeutic agent may be an agent intended to increase or potentiate an immune response, such as a cytokine, an agent intended to inhibit an immune checkpoint pathway or stimulate an immune potentiating pathway or an agent which inhibits the activity of regulatory T cells (Tregs) or myeloid derived suppressor cells (MDSCs).

The therapeutic agent may be an agent known for use in an existing cancer therapeutic treatment. The therapeutic agent may be radiotherapy or a chemotherapeutic agent. The therapeutic agent may be selected from cyclophosmamide, alkylating-like agents such as cisplatin or melphalan, plant alkaloids and terpenoids such as vincristine or paclitaxel (Taxol), antimetabolites such as 5-fluorouracil, topoisomerase inhibitors type I or II such as camptothecin or doxorubicin, cytotoxic antibiotics such as actinomycin, anthracyclines such as epirubicin, glucocorticoids such as triamcinolone, inhibitors of protein, DNA and/or RNA synthesis such as methotrexate and dacarbaxine, histone deacetylase (HDAC) inhibitors, or any other chemotherapy agent.

The therapeutic agent may be one, or a combination of: immunotherapeutics or immunomodulators, such as TLR agonists; agents that down-regulate T-regulatory cells such as cyclophosphamide; or agents designed to block immune checkpoints or stimulate immune potentiating pathways, including but not limited to monoclonal antibodies, such as a CTLA-4 inhibitor, a PD-1 inhibitor, a PD-L1 inhibitor, a LAG-3 inhibitor, a TIM-3 inhibitor, a VISTA inhibitor, a CSF1R inhibitor, an IDO inhibitor, a CEACAM1 inhibitor, a GITR agonist, a 4-1-BB agonist, a KIR inhibitor, a SLAMF7 inhibitor, an OX40 agonist, a CD40 agonist, an ICOS agonist or a CD47 inhibitor. In a preferred embodiment, the therapeutic agent is a CTLA-4 inhibitor such as an anti-CTLA-4 antibody, a PD1 inhibitor, such as an anti-PD-1 antibody or a PD-L1 inhibitor such as an anti-PD-L1 antibody. Such inhibitors, agonists and antibodies can be generated and tested by standard methods known in the art.

Immunotherapeutic agents may also include bi-specific antibodies, cell based-therapies based on dendritic cells, NK cells or engineered T cells such CAR-T cells or T cells expressing engineered T cell receptors. Immunotherapeutic agents also include agents that target a specific genetic mutation which occurs in tumors, agents intended to induce immune responses to specific tumor antigens or combinations of tumor antigens, including neoantigens and/or agents intended to activate the STING/cGAS pathway, TLR or other innate immune response and/or inflammatory pathway, including intra-tumoral agents.

For example, a virus of the invention may be used: in combination with dacarbazine, a BRAF inhibitor and or CTLA-4, PD1 or PD-L1 blockade to treat melanoma; in combination with taxol, doxorubicin, vinorelbine, cyclophosphamide and/or gemcitabine to treat breast cancer; in combination with 5-fluorouracil and optionally leucovorin, irinoteacan and/or oxaliplatin to treat colorectal cancer; in combination with taxol, carboplatin, vinorelbine and/or gemcitabine, PD-1 or PD-L1 blockade to treat lung cancer; in combination with cisplatin and/or radiotherapy to treat head and neck cancer.

The therapeutic agent may be an inhibitor of the idoleamine 2,3-dioxygenase (IDO) pathway. Examples of IDO inhibitors include epacadostat (INCB024360), 1-methyltryptophan, Indoximod (1-methyly-D-tryptophan), GDC-0919 or F001287.

The mechanism of action of IDO in suppressing antitumor immune responses may also suppress immune responses generated following oncolytic virus therapy. IDO expression is induced by toll like receptor (TLR) activation and interferon-γ both of which may result from oncolytic virus infection. One embodiment of the use of oncolytic virus therapy for cancer treatment includes combination of an oncolytic virus, including a virus expressing GM-CSF and an immune co-stimulatory pathway activating molecule or molecules with an inhibitor of the IDO pathway and optionally one or more antagonist of an immune co-inhibitory pathway and/or one or more agonist of an immune co-stimulatory pathway, including those targeting CTLA-4, PD-1 and/or PD-L1.

The invention also provides a method of treating cancer, which comprises administering a therapeutically effective amount of an oncolytic virus, an inhibitor of the indoleamine 2,3-dioxygenase (IDO) pathway and a further antagonist of an immune co-inhibitory pathway, and/or an agonist of an immune co-stimulatory pathway to a patient in need thereof.

The oncolytic virus is preferably a modified clinical isolate. The oncolytic virus is preferably a pox virus, more preferably a HSV, such as a HSV1 and/or a HSV rendered functionally inactive for ICP34.5 and/or ICP47.

The oncolytic virus may express an immune stimulating molecule, such as GM-CSF and/or a co-stimulatory pathway encoding molecule such as CD40L, GITRL, OX4OL, 4-I-BBL or ICO5L, and/or an inhibitor of CTLA-4, and/or a fusogenic protein, such as the GALV fusogenic glycoprotein with the R sequence mutated or deleted.

The further antagonist of an immune co-inhibitory pathway is preferably an antagonist of CTLA-4, an antagonist of PD1 or an antagonist of PD-L1. For example, the further antagonist of an immune co-inhibitory pathway may be an inhibitor of the interaction between PD1 and PD-L1.

Where a therapeutic agent and/or radiotherapy is used in conjunction with a virus of the invention, administration of the virus and the therapeutic agent and/or radiotherapy may be contemporaneous or separated by time. The composition of the invention may be administered before, together with or after the therapeutic agent or radiotherapy. The method of treating cancer may comprise multiple administrations of the virus of the invention and/or of the therapeutic agent and/or radiotherapy. In preferred embodiments, in the case of combination with immune checkpoint blockade or other immune potentiating agents, the virus of the invention is administered once or multiple times prior to the concurrent administration of the immune checkpoint blockade or other immune potentiating agent or agents thereafter, or concurrent with the administration of the immune checkpoint blockade or other immune potentiating agent or agents without prior administration of the virus of the invention.

The virus of the invention may be administered to a subject by any suitable route. Typically, a virus of the invention is administered by direct intra-tumoral injection. Intra-tumoral injection includes direct injection into superficial skin, subcutaneous or nodal tumors, and imaging guided (including CT, MRI or ultrasound) injection into deeper or harder to localize deposits including in visceral organs and elsewhere. The virus may be administered into a body cavity, for example into the pleural cavity, bladder or by intra-peritoneal administration. The virus may be injected into a blood vessel, preferably a blood vessel supplying a tumor.

Therapeutic agents which may be combined with a virus of the invention can be administered to a human or animal subject in vivo using a variety of known routes and techniques. For example, the composition may be provided as an injectable solution, suspension or emulsion and administered via parenteral, subcutaneous, oral, epidermal, intradermal, intramuscular, interarterial, intraperitoneal, intravenous injection using a conventional needle and syringe, or using a liquid jet injection system. The composition may be administered topically to skin or mucosal tissue, such as nasally, intratrachealy, intestinally, sublingually, rectally or vaginally, or provided as a finely divided spray suitable for respiratory or pulmonary administration. In preferred embodiments, the compositions are administered by intravenous infusion, orally, or directly into a tumor.

The virus and/or therapeutic agent may be administered to a subject in an amount that is compatible with the dosage composition that will be therapeutically effective. The administration of the virus of the invention is for a "therapeutic" purpose. As used herein, the term "therapeutic" or "treatment" includes any one or more of the following as its objective: the prevention of any metastasis or further metastasis occurring; the reduction or elimination of symptoms; the reduction or complete elimination of a tumor or cancer, an increase in the time to progression of the patient's cancer; an increase in time to relapse following treatment; or an increase in survival time.

Therapeutic treatment may be given to Stage I, II, III, or IV cancers, preferably Stage II, III or IV, more preferably Stage III or IV, pre- or post-surgical intervention (i.e. following recurrence or incomplete removal of tumors following surgery), preferably before any surgical intervention (either for resection of primary or recurrent/metastatic disease), or following recurrence following surgery or following incomplete surgical removal of disease, i.e. while residual tumor remains.

Therapeutic treatment may be carried out following direct injection of the virus composition into target tissue which may be the tumor, into a body cavity, or a blood vessel. As a guide, the amount of virus administered is in the case of HSV in the range of from $10^4$ to $10^{10}$ pfu, preferably from $10^5$ to $10^9$ pfu. In the case of HSV, an initial lower dose (e.g. $10^4$ to $10^7$ pfu) may be given to patients to seroconvert patients who are seronegative for HSV and boost immunity in those who are seropositive, followed by a higher dose then being given thereafter (e.g. $10^6$ to $10^9$ pfu). Typically up to 20 ml of a pharmaceutical composition consisting essentially of the virus and a pharmaceutically acceptable suitable carrier or diluent may be used for direct injection into tumors, or up to 50 ml for administration into a body cavity (which may be subject to further dilution into an appropriate diluent before administration) or into the bloodstream. However for some oncolytic therapy applications larger or smaller volumes may also be used, depending on the tumor and the administration route and site.

The routes of administration and dosages described are intended only as a guide since a skilled practitioner will be able to determine readily the optimum route of administration and dosage. The dosage may be determined according to various parameters, especially according to the location of the tumor, the size of the tumor, the age, weight and condition of the patient to be treated and the route of administration. Preferably the virus is administered by direct injection into the tumor or into a body cavity. The virus may also be administered by injection into a blood vessel. The optimum route of administration will depend on the location and size of the tumor. Multiple doses may be required to achieve an immunological or clinical effect, which, if required, will be typically administered between 2 days to 12 weeks apart, preferably 3-days to 3 weeks apart. Repeat doses up to 5 years or more may be given, preferably for up to one month to two years dependent on the speed of response of the tumor type being treated and the response of a particular patient, and any combination therapy which may also be being given.

The following Examples illustrate the invention.

Example 1. Construction of a Virus of the Invention

The virus species used to exemplify the invention is HSV, specifically HSV1. The strain of HSV1 used for exemplification is identified through the comparison of more than 20 primary clinical isolates of HSV1 for their ability to kill a panel of human tumor-derived cell lines and choosing the virus strain with the greatest ability to kill a broad range of these rapidly, and at low dose. Tumor cell lines used for this comparison include U87MG (glioma), HT29 (colorectal), LNCaP (prostate), MDA-MB-231 (breast), SK-MEL-28 (melanoma), Fadu (squamous cell carcinoma), MCF7 (breast), A549 (lung), MIAPACA-2 (pancreas), CAPAN-1 (pancreas), and/or HT1080 (fibrosarcoma).

Specifically, each primary clinical isolate of HSV is titrated onto each of the cell lines used for screening at MOIs such as 1, 0.1, 0.01 and 0.001 and assessed for the extent of cell death at time points such as 24 and 48 hrs at each dose. The extent of cell killing may be assessed by e.g. microscopic assessment of the proportion of surviving cells at each time point, or e.g. a metabolic assay such as an MTT assay. The exemplary virus of the invention is then constructed by deletion of ICP47 from the viral genome using homologous recombination with a plasmid containing regions flanking HSV1 nucleotides 145300 to 145582 (HSV1 nucleotides 145300 to 145582 being the sequences to be deleted; HSV1 strain 17 sequence Genbank file NC 001806.2) between which are encoded GFP. GFP expressing virus plaques are selected, and GFP then removed by homologous recombination with the empty flanking regions and plaques which do not express GFP are selected. This results in an ICP47 deleted virus in which US11 is expressed as an IE protein as it is now under the control of the TCP47 promoter. ICP34.5 is then deleted using homologous recombination with a plasmid containing regions flanking HSV1 nucleotides 124953 to 125727 (HSV1 nucleotides 124953 to 125727 being the sequences to be deleted; HSV1 strain 17 sequence Genbank file NC 001806.2) between which GFP is encoded. GFP expressing virus plaques are again selected, and GFP then removed by homologous recombination with the same flanking regions but between which are now an expression cassette comprising a codon optimized version of the mouse GM-CSF sequence, a codon optimized version of the GALV R- sequence and codon optimized version of mouse soluble multimeric CD40L driven by a CMV, an RSV and an SV40 promoter. Non-GFP expressing plaques are selected.

The structure of the resulting virus is shown in FIG. 1. The mGM-CSF, CD40L and GALV-R- sequences are shown in SEQ ID NOs 2, 14 and 8 respectively. The structure of the resulting virus is confirmed by restriction digestion and Southern blot, GM-CSF and CD40L expression is confirmed by ELISA, and GALV-R- expression is confirmed by infection of human HT1080 tumor cells and the observation of syncitial plaques.

Viruses are also constructed using similar procedures which only have inserted the gene for GALVR- or mouse GM-CSF and GALV-R-, but without CD40L. The structures of these viruses are also shown in FIG. 1.

For human use, hGM-CSF and hCD40L are used, the sequence for codon optimised versions of which are shown in SEQ ID NO 4 and 13.

Example 2. The Effect of the Combined Expression of GM-CSF and an Immune Co-Stimulatory Pathway Activating Molecule from an Oncolytic Virus in Mouse Tumor Models The GALV R- protein causes cell to cell fusion in human cells but not in mouse cells because the PiT-1 receptor required for cell fusion to occur has a sequence in mice which does not allow cell fusion to occur. As a result mouse tumor cells expressing human PiT-1 are first prepared using methods standard in the art. Human PiT-1 is cloned into a lentiviral vector also comprising a selectable marker gene. The vector is transfected into target CT26 mouse colorectal cancer tumor cells and clones resistant to the selectable marker are selected to generate CT26/PiT-1 cells. PiT-1 expression is confirmed by western blotting in untransfected cells and in cells transfected with the PiT-1 expressing lentivirus and by transfection of a plasmid expressing GALV-R- and confirmation that cell fusion occurs.

The utility of the invention is demonstrated by administering CT26/PiT-1 cells into both flanks of Balb/c mice and allowing the CT26/PiT-1 tumors to grow to approximately 0.5 cm in diameter.

The following treatments are then administered to groups of mice (five per group), into one flank of each mouse only 3 times per week for two weeks:
- 50 µl of saline (1 group);
- 50 µl of $10^5$ pfu/ml, $10^6$ pfu/ml, or $10^7$ pfu/ml of the HSV with only GALVR-inserted (3 groups);
- 50 µl of $10^5$ pfu/ml, $10^7$ pfu/ml, or $10^7$ pfu/ml of the HSV with only GALVR- and mouse GM-CSF inserted (3 groups);
- 50 µl of $10^5$ pfu/ml, $10^6$ pfu/ml, or $10^7$ pfu/ml of the virus with GALVR- and both mouse GM-CSF and CD40L inserted (3 groups).

Effects on tumor growth are then observed for up to one month. Superior tumor control and shrinkage in both injected and uninjected tumors with the virus expressing GM-CSF and CD40L as compared to the other groups is observed, including through an improved dose response curve.

Example 3. The Effect of Combined Expression of GM-CSF and an Immune Co-Stimulatory Pathway Activating Molecule from an Oncolytic Virus on the Therapeutic Effect of Immune Checkpoint Blockade in Mouse Tumor Models The experiment in Example 2 above is repeated but mice are additionally dosed bi-weekly by the intra-peritoneal route with an antibody targeting mouse PD-1 (10 mg/kg; Bioxcell RMP-1-14 on the same days as virus dosing) or an antibody targeting mouse CTLA-4 (10 mg/kg; Bioxcell 9H10 on the same days as virus dosing). An additional group of mice is added which receive no antibody treatment. More specifically, groups of mice receive (1) saline. (2) HSV with GALVR- inserted as in Example 2, (3) HSV with GM-CSF and GALV-R- inserted as in Example 2, (4) HSV with GM-CSF, CD40L and GALV-R-inserted as in Example 2, (5) PD-1 antibody, (6) CTLA-4 antibody, (7) HSV with GALV-R- inserted plus PD-1 antibody, (8) HSV with GALV-R- inserted gene plus CTLA-4 antibody. (9) HSV with GM-CSF and GALV-R- and PD-1 antibody or (10) HSV with GM-CSF and GALV-R- and CTLA-4 antibody (11) HSV with GM-CSF, CD40L and GALV-R- and PD-1 antibody or (12) HSV with GM-CSF, CD40L and GALV-R- and CTLA-4 antibody. Superior tumor control and shrinkage in both injected and uninjected tumors with the virus expressing GM-CSF and CD40L together with the anti-PD-1 antibody or the anti-CTLA-4 antibody as compared to the other groups is observed, including through an improved dose response curve.

Example 4. Collection of Clinical Isolates

The virus species used to exemplify the invention is HSV, specifically HSV1. To exemplify the invention, 181 volunteers were recruited who suffered from recurrent cold sores. These volunteers were given sample collection kits (including Sigma Virovult collection tubes), and used these to swab cold sores when they appeared following which these samples were shipped to Replimune, Oxford UK. From June 2015-February 2016, swabs were received from 72 volunteers. A sample of each swab was used to infect BHK cells. Of these 36 live virus samples were recovered following plating out and growth on BHK cells. These samples are detailed in Table 1.

TABLE 1

Details of Tested Swab Samples & Result

| Sample Number | Virus retrieved |
| --- | --- |
| RH001A | No |
| RH001B | |
| RH002A | Yes |
| RH003A | No |
| RH004A | Yes |
| RH004B | |
| RH005A | No |
| RH005B | |
| RH006A | No |
| RH006B | |
| RH007A | Yes |
| RH007B | |
| RH007C | |
| RH008A | No |
| RH008B | |
| RH008C | |
| RH009A | No |
| RH009B | |
| RH010A | No |
| RH011A | No |
| RH011B | |
| RH011C | |
| RH012A | No |
| RH013A | No |
| RH014A | Yes |
| RH014B | |
| RH015A | Yes |
| RH016A | No |
| RH016B | |
| RH017A | Yes |
| RH018A | Yes |
| RH018B | |
| RH018C | |
| RH019A | No |
| RH019B | |
| RH019C | |
| RH020A | Yes-RH020A only |
| RH020B | |
| RH020C | |
| RH021A | Yes |
| RH021B | |
| RH022A | Yes |

TABLE 1-continued

Details of Tested Swab Samples & Result

| Sample Number | Virus retrieved |
|---|---|
| RH022B | |
| RH023A | Yes |
| RH024A | No |
| RH025A | Yes-RH025B only |
| RH025B | |
| RH026A | Yes |
| RH027A | No |
| RH027B | |
| RH027C | |
| RH028A | No |
| RH028B | |
| RH028C | |
| RH029A | No |
| RH030A | No |
| RH031A | Yes-RH031A to |
| RH031B | RH031D |
| RH031C | |
| RH031D | |
| RH031E | |
| RH031F | |
| RH032A | No |
| RH033A | No |
| RH033B | |
| RH033C | |
| RH034A | No |
| RH034B | |
| RH034C | |
| RH035A | No |
| RH036A | Yes |
| RH037A | Yes |
| RH038A | Yes |
| RH039A | No |
| RH039B | |
| RH039C | |
| RH040A | Yes |
| RH040B | |
| RH040C | |
| RH041A | Yes |
| RH042A | Yes |
| RH043A | No |
| RH043B | |
| RH043C | |
| RH044A | No |
| RH045A | No |
| RH046A | Yes |
| RH047A | Yes-RH047A and |
| RH047B | RH047C |
| RH047C | |
| RH048A | No |
| RH049A | No |
| RH049B | |
| RH049C | |
| RH050A | No |
| RH051A | Yes |
| RH051B | |
| RH052A | Yes-RH052A only |
| RH052B | |
| RH053A | No |
| RH054A | No |
| RH055A | No |
| RH055B | |
| RH056A | Yes |
| RH057A | No |
| RH058A | Yes |
| RH058B | |
| RH059A | No |
| RH060A | No |
| RH061A | Yes |
| RH062A | No |
| RH063A | No |
| RH064A | Yes |
| RH065A | Yes |
| RH065B | |
| RH066A | No |
| RH067A | No |
| RH067B | |
| RH068A | No-contaminated |
| RH069A | No |
| RH069A | |
| RH070A | Yes |
| RH071A | Yes |
| RH072A | No |
| RH073A | Yes |
| RH073B | |
| RH074A | No |
| RH074B | |
| RH075A | No |
| RH076A | No |
| RH078A | No |
| RH078B | |
| RH079B | Yes |
| RH079B | |
| RH080A | No |
| RH081A | Yes |
| RH082A | No |
| RH082B | |
| RH083A | Yes |
| RH083B | |
| RH084A | Yes |
| RH084B | |
| RH084C | |
| RH085A | No |
| RH086A | No |
| RH087A | Yes-RH078B only |
| RH087B | |

Designations A, B, C etc. indicate multiple swabs from the same volunteer.

Example 5. Identification of Clinical Isolates with Improved Anti-Tumor Effects

The abilities of the primary clinical isolates of HSV1 to kill a panel of human tumor-derived cell lines was tested. The tumor cell lines used for this comparison were HT29 (colorectal), MDA-MB-231 (breast), SK-MEL-28 (melanoma), Fadu (squamous cell carcinoma), MCF7 (breast), A549 (lung), MIAPACA-2 (pancreas) and HT1080 (fibrosarcoma). The cell lines were used to test for the level of CPE achieved at a range of MOI and times post infection for each of the primary clinical isolates.

Experiments were conducted in parallel using 5 to 8 of the new viruses strains at the same time. The virus strains were plated out in duplicate at a range of MOIs (0.001-1), and the extent of CPE following crystal violet staining was assessed at 24 and 48 hours following infection. The viral strains which were most effective at killing the tumor cell lines were scored, and the most effective two or three strains from each screen of 5-8 strains were identified and compared in parallel in a further experiment to identify the top strains for further development.

The initial screens demonstrated substantial variability in the ability of the different strains to kill the different tumor cell lines. Of an initial 29 strains tested, 8 strains of interest were identified in the initial screens for further comparison. These were strains RH004A, RH015A, RH018A, RH021A, RH023A, RH31A, RH040A, and RH047A.

Figure 2:
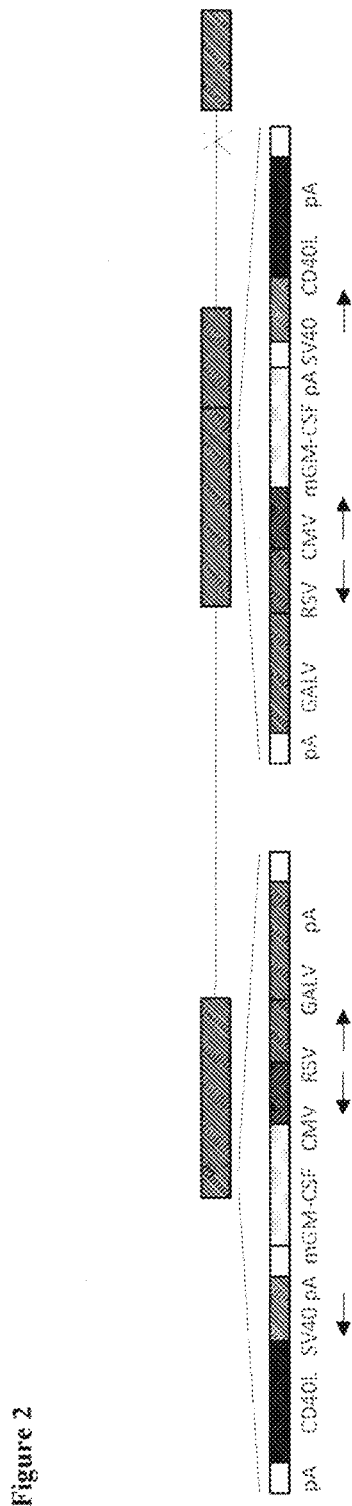
FIG. 2 shows the differential abilities of the eight top ranking HSV1 clinical isolate strains as assessed by crystal violet staining 24 hours or 48 hours after infection with a MOI of 0.1, 0.01 or 0.001 as indicated in the Figure to kill Fadu, SK-mel-28, A549, HT1080, MIA-PA-CA-2, HT29 and MDA-MB-231 human tumor cell lines. The virus strains ranked first and second on each cell line are indicated. The virus RH018A was ranked first on each of the Fadu, HT1080, MIA-PA-CA-2 and HT29 cell lines and second on each of the SK-mel-28, A549 and MDA-MB-231 cell lines. RH004A was ranked joint first with RH018A and RH015A on the HT29 cell line, first on the SK-mel-28 and A549 cell lines and second on the Fadu cell line. RH023A was ranked first on the MDA-MB-231 cell line and second on the HT1080 cell line. RH031A was ranked second on each of the MIA-PA-CA-2 and HT29 cell lines. RH040A was ranked joint second on the HT29 cell line.

The 8 strains for further comparison were tested in parallel on the panel of tumor cell lines, and their relative ability to kill these tumor cell lines was assessed following crystal violet staining and observation for CPE. FIG. 2 shows a representative time point and MOI for these viruses on each of the viruses on each of the cell lines demonstrating the differential ability of the viruses to kill the target tumor cell lines observed.

There was substantial variation amongst the strains, and it was found that while a particular strain may be particularly effective at killing one cell line, it is not necessarily particularly effective at killing other cell lines too, further demonstrating the degree of variability in the ability of clinical strains of HSV to kill tumor cells of different types.

Figure 3:
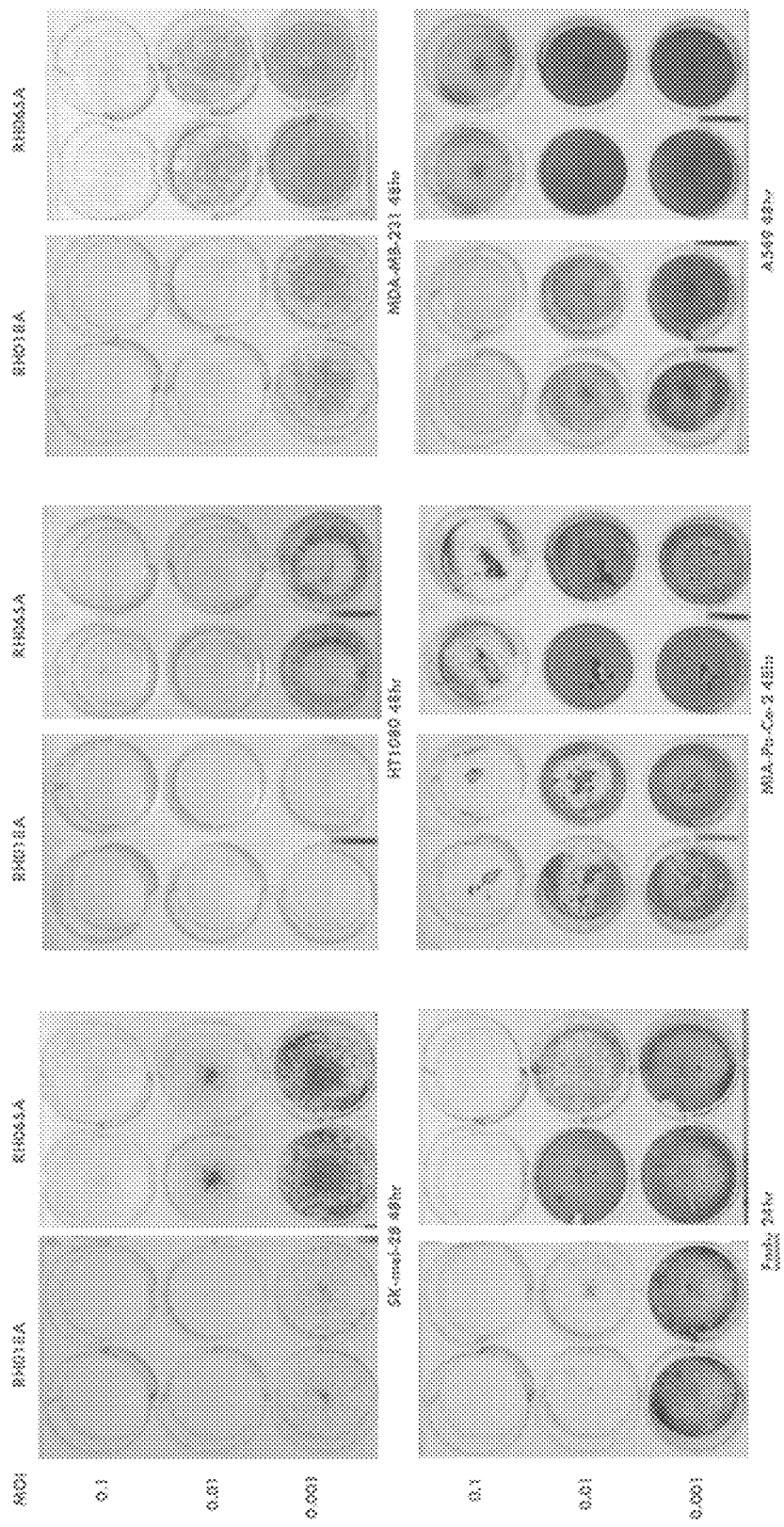
FIG. 3 shows a comparison between strain RH018A, the strain ranked first of all the strains tested, with an 'average' strain from the screen (i.e. strain RH065A). Approximately 10 fold less of strain RH018A was needed to kill an equal proportion of cells than was needed of strain RH065A as shown by crystal violet staining 24 or 48 hours post infection with MOIs of 0.1, 0.01 and 0.001 in SK-mel-28, HT1080. MDA-MB-231, Fadu, MIA-PA-CA-2 and A549 cell lines.
Figure 4A:
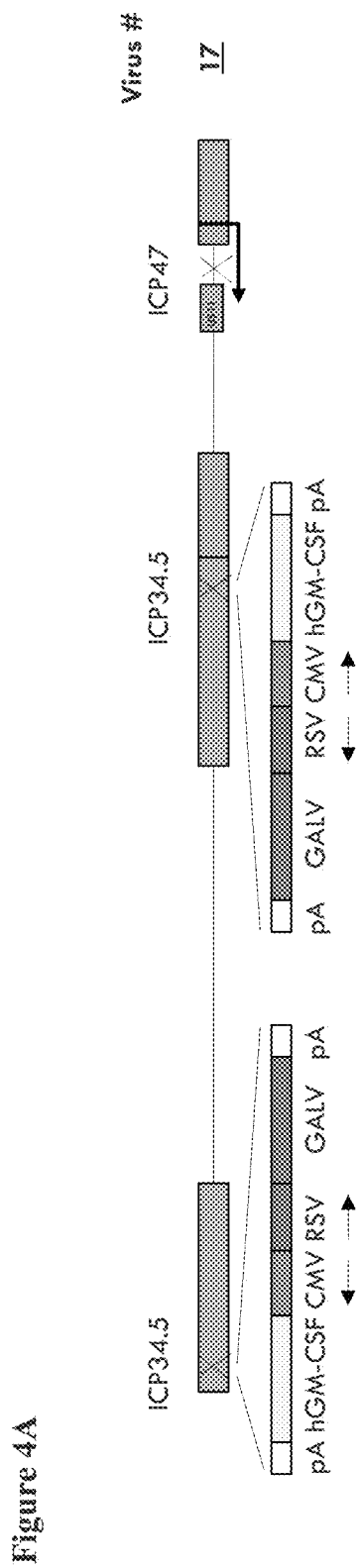
FIGS. 4A-4F and 5A-5F depict structures of HSV1 viruses modified by the deletion of ICP34.5 and ICP47 such that the US11 gene is under control of the ICP457 immediate early promoter and containing heterologous genes in the ICP34.5 locus. The viruses were constructed using the RH018A strain unless otherwise stated in the Figure.
Figure 4B:
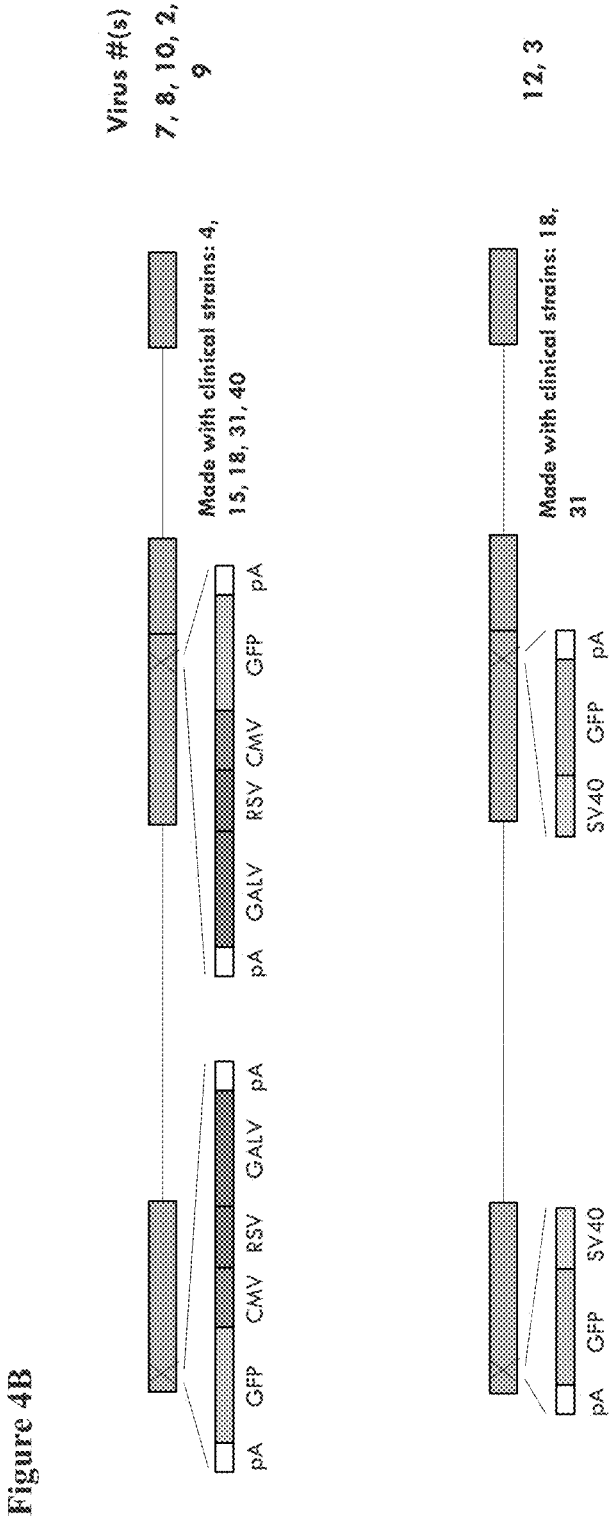
Figure 4C:
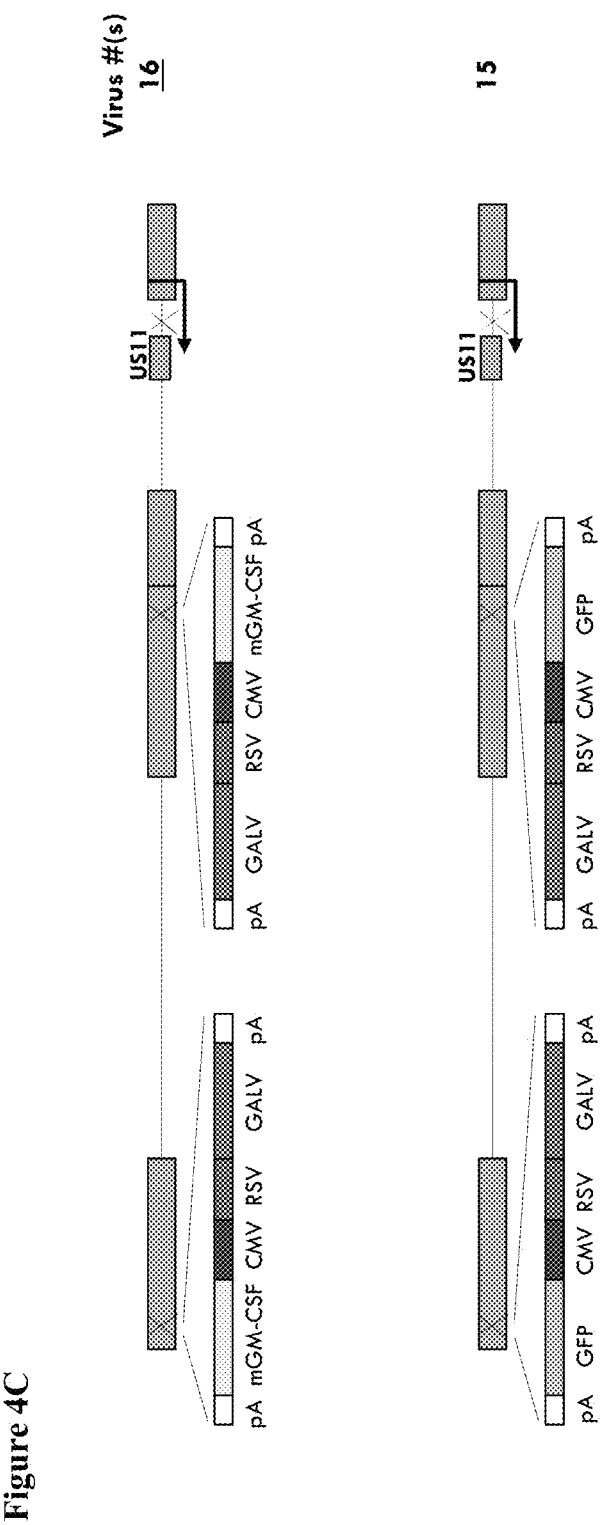
Figure 4D:
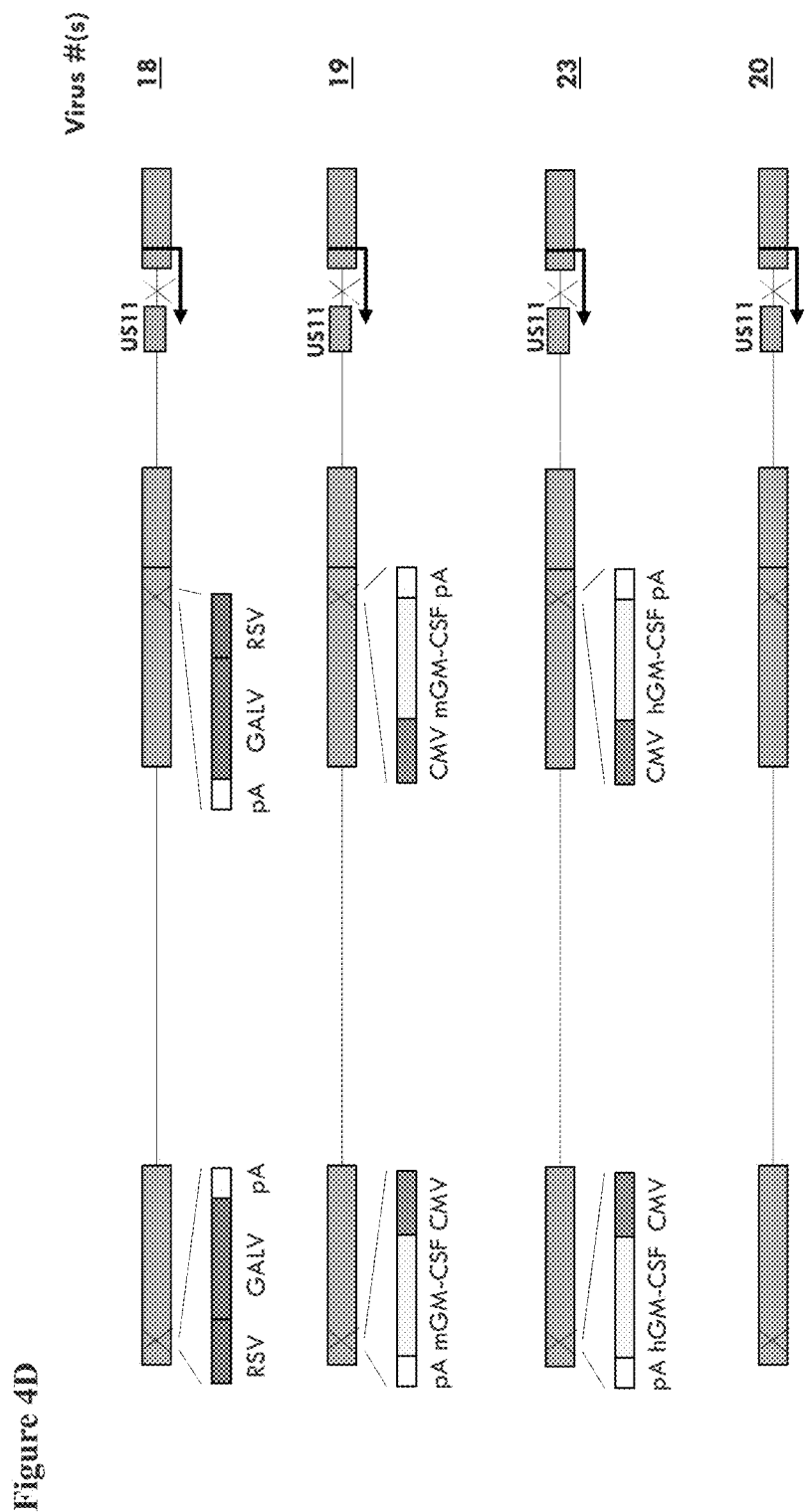
Figure 4E:
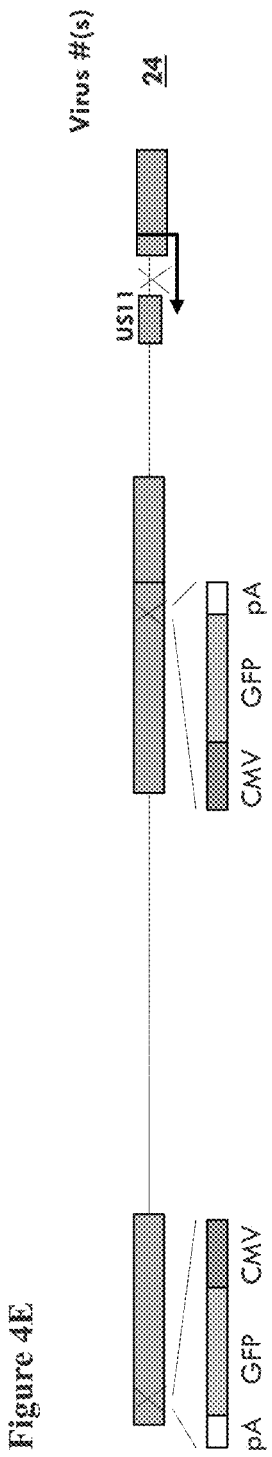
Figure 4F:
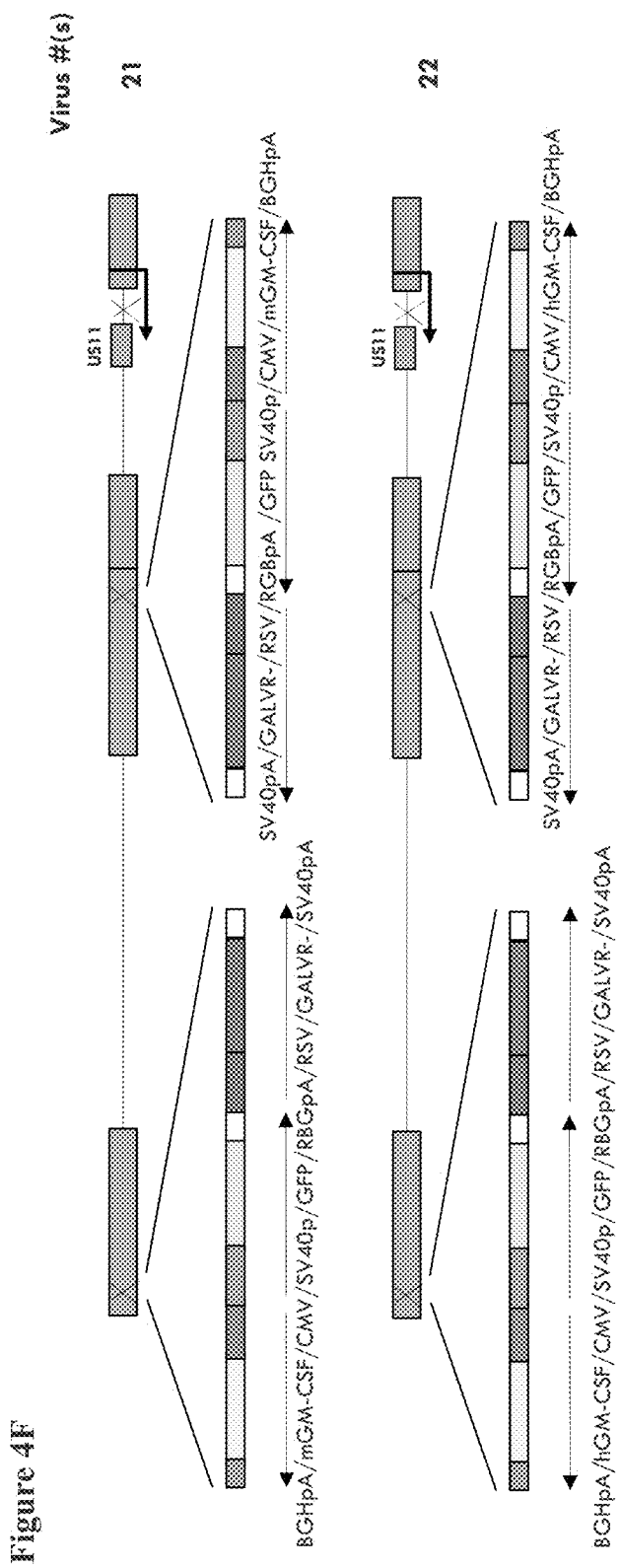
Figure 5A:
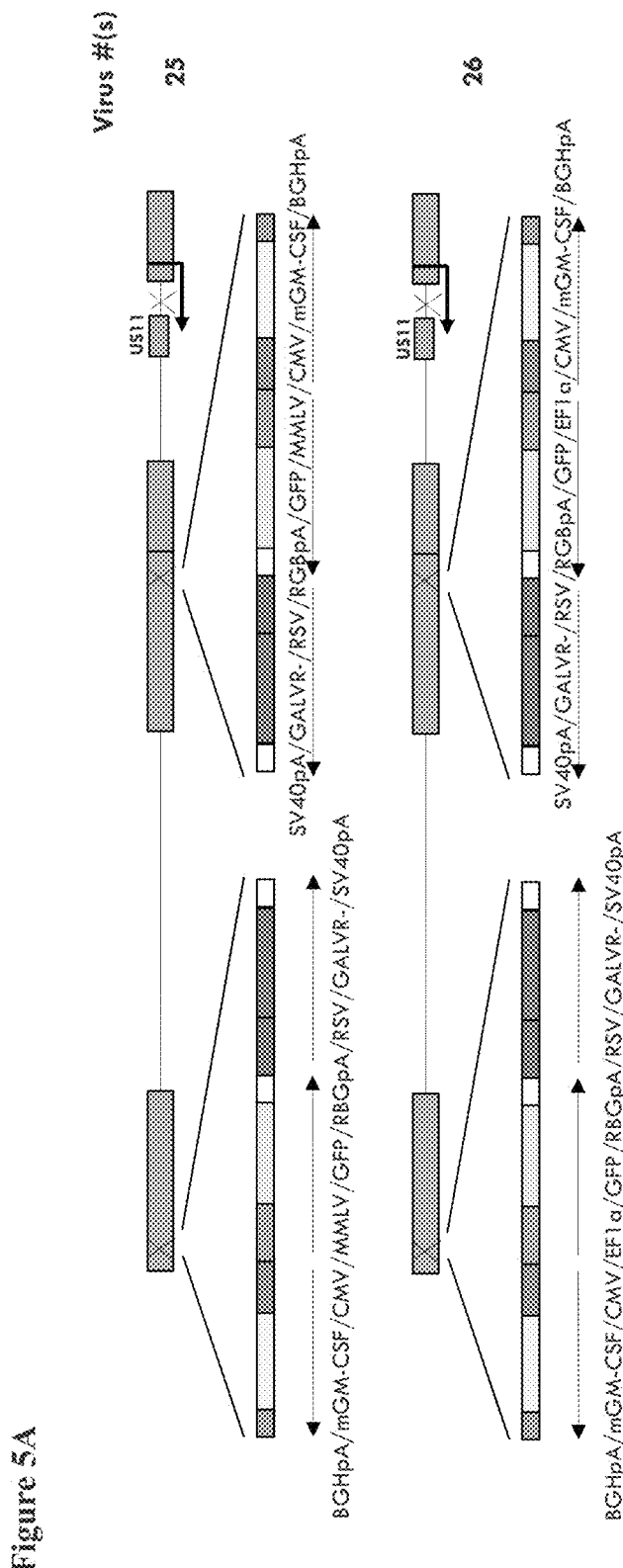
Figure 5B:
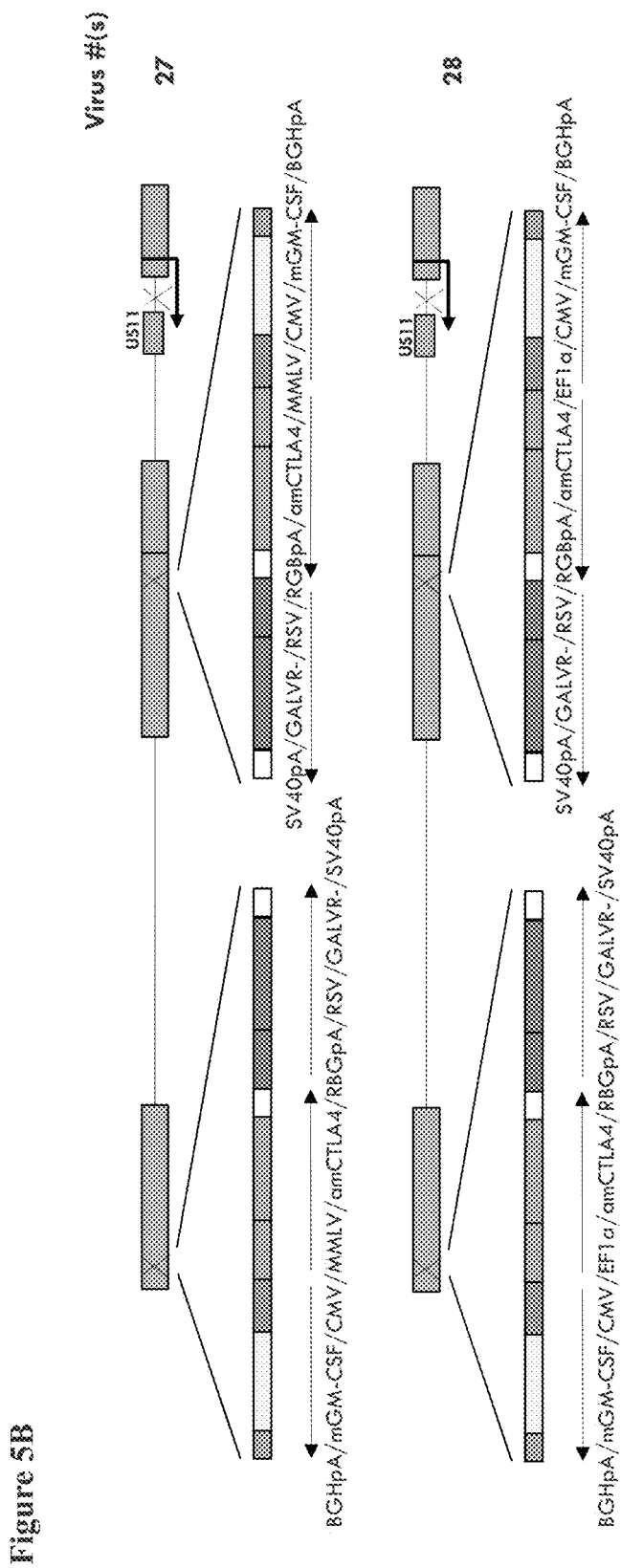
Figure 5C:
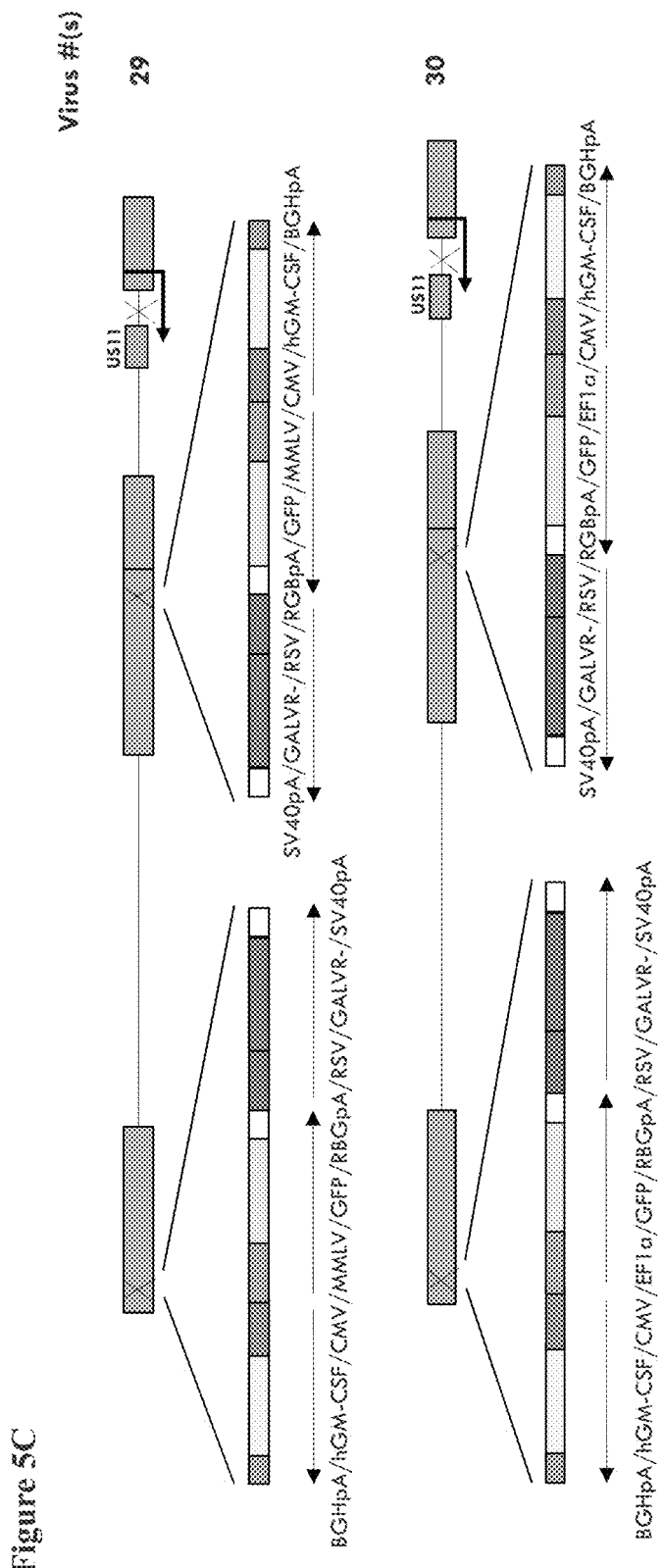
Figure 5D:
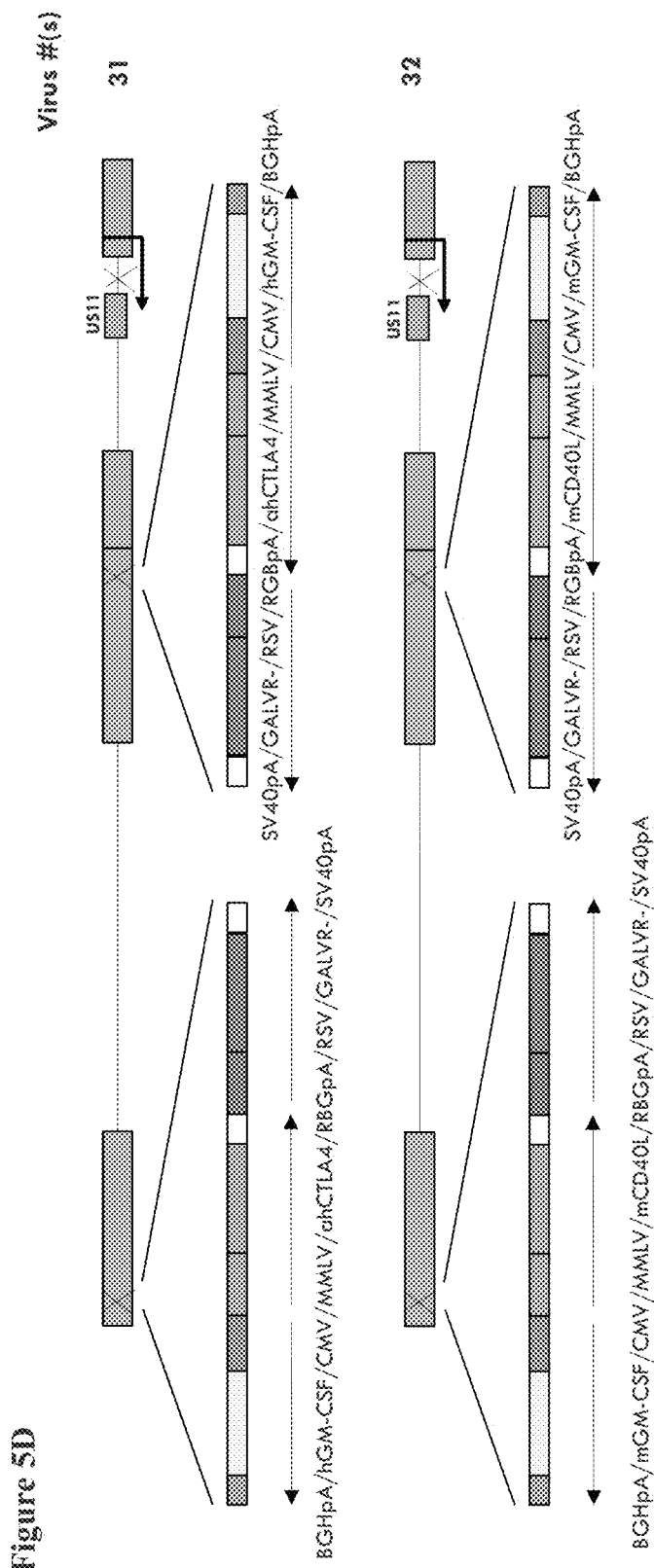
Figure 5E:
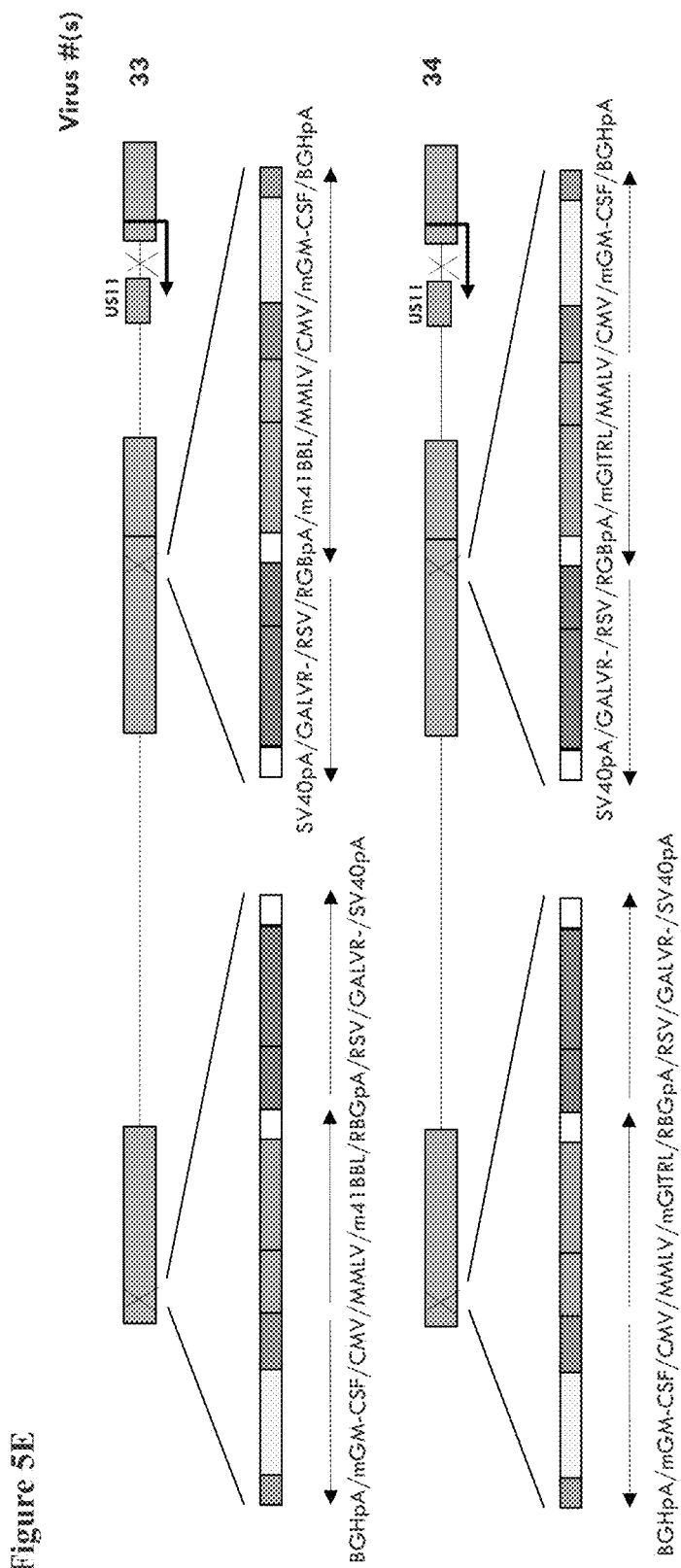
Figure 5F:
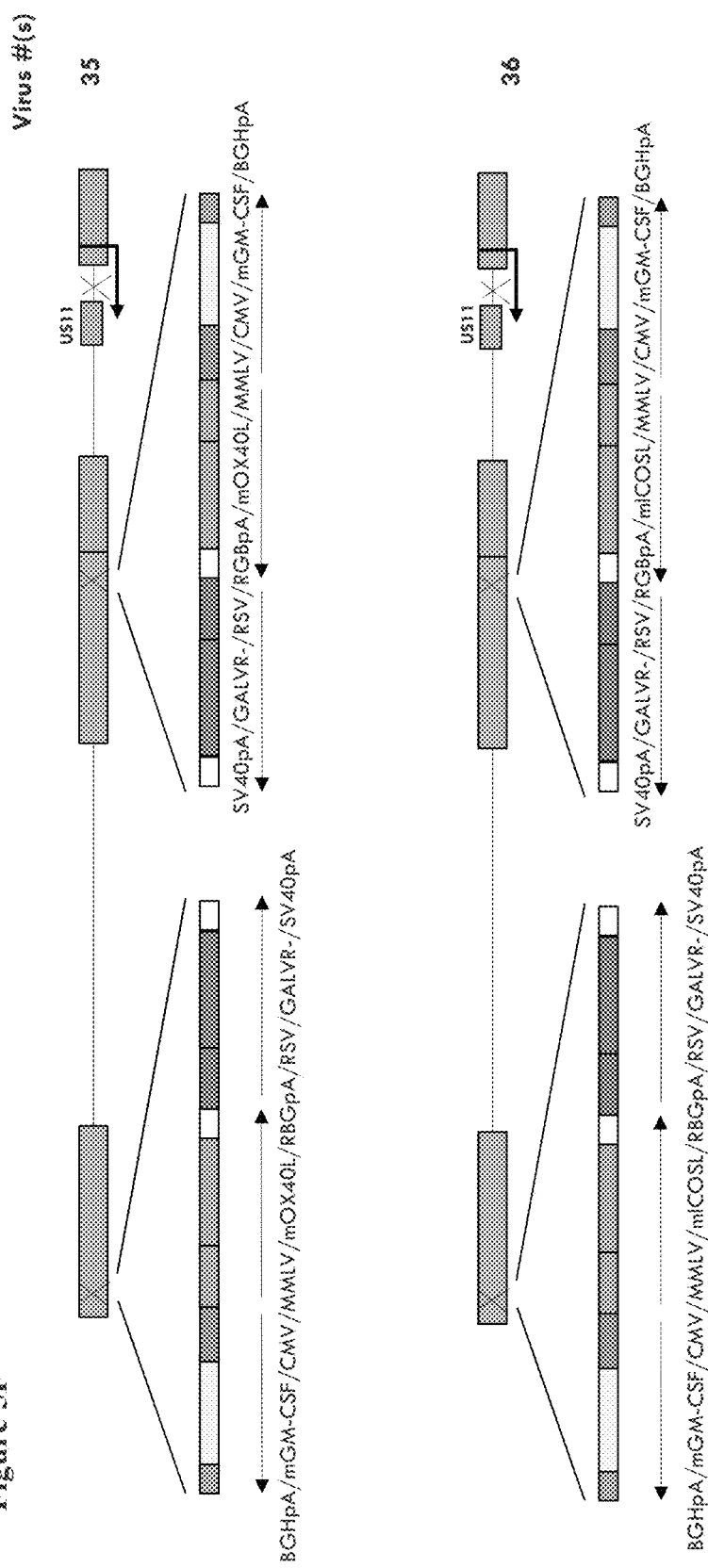

FIG. 3 also indicates which of the virus strains was both best and second best at killing each of the cell lines, enabling the virus strains to be rank ordered as to their overall relative ability to kill the panel of cell lines as a whole. This analysis demonstrated that strains RH004A, RH015A, RH018A, RH031A and RH040A were relatively more effective than the other strains, and these five strains were chosen for potential further development as oncolytic agents. Of these top five strains, the relative rank order based on their abilities to kill across the panel of cell lines was RH018A>RH004A>RH031A>RH040A>RH015A.

More specifically, in these experiments, the tumor cell lines were used to seed multi-well tissue culture plates so that they were about 80% confluent on the day of infection. Representative wells from each tumor cell line were trypsinised and the number of cells in the well determined. These cell counts are used to determine the volume of each clinical isolate required to give an MOI of 1, 0.1, 0.01 and 0.001. Separate wells of a tumor cell line were infected with the clinical isolate at these MOI. All infections are carried out in quadruplicate. Duplicate wells were incubated for 24 hours and duplicate wells were incubated for 48 hours, both at 37° C., 5% $CO_2$, prior to fixation of the cells with glutaraldehyde and staining with crystal violet. The level of cell lysis was then assessed by gross observation, microscopy (cell counts) and photography.

Strain RH018A, the strain ranked first of all the strains tested was compared to an 'average' strain from the screen (i.e. a strain which was not in the top 8, but was also not in the group of strains which were least effective and killing the panel of tumor cell lines). This comparison showed that Strain RH018A was approximately 10 fold more effective than this average strain (Strain RH065A) at killing the tumor cell lines (i.e. approximately 10 fold less of Strain RH018A was needed to kill an equal proportion of cells than was needed of Strain RH065A). This is shown in FIG. 3.

Example 6. Modification of Clinical Isolates

In this Example the clinical isolates selected in Example 5 were modified by deletion of ICP34.5 from the viral genome using homologous recombination with a plasmid containing regions flanking the TCP34.5 encoding gene (nucleotides 143680-145300 and 145,582-147,083; HSV1 strain 17 sequence Genbank file NC 001806.2) between which are encoded GFP and the GALV-R-fusogenic glycoprotein. The structure of this virus, (Virus 10) is shown in FIGS. 4A-4F.

Additional viruses based on Strain RH018A were also constructed in which both ICP34.5 and ICP47 (using flanking regions containing nucleotides 123464-124953 and 125727-126781; HSV1 strain 17 sequence Genbank file NC 001806.2) were deleted (resulting in placement of US11 under the control of the ICP47 promoter). To construct these viruses, GFP expressing virus plaques, with GFP expressed in place of ICP47 were first selected. GFP was then removed by homologous recombination with the empty flanking regions, and plaques not expressing GFP were selected. This resulted in an ICP47 deleted virus in which US11 is expressed as an IE protein as it is now under the control of the ICP47 promoter. ICP34.5 was then deleted using homologous recombination with a plasmid containing regions flanking HSV1 nucleotides 143680-145300 and 145,582-147,083; HSV1 strain 17 sequence Genbank file NC 001806.2) between which GFP is encoded. GFP expressing virus plaques were again selected, and GFP then removed by homologous recombination with the same flanking regions but between which are now an expression cassette comprising the genes to be inserted. The viruses that were constructed are shown in FIGS. 1, 4 and 5. These included a codon optimized version of the mouse GM-CSF sequence and a codon optimized version of the GALV R- sequence driven by the CMV IE promoter and RSV promoter respectively, in a back to back orientation and again selecting virus plaques which do not express GFP. This virus construction was performed using methods which are standard in the art.

The mGM-CSF and GALV-R- sequences are shown in SEQ ID NOs 2 and 8 respectively. The structure of the resulting virus was confirmed by PCR, GM-CSF expression was confirmed by ELISA, and GALV-R- expression was confirmed by infection of human HT1080 tumor cells and the observation of syncitial plaques.

Figure 6:
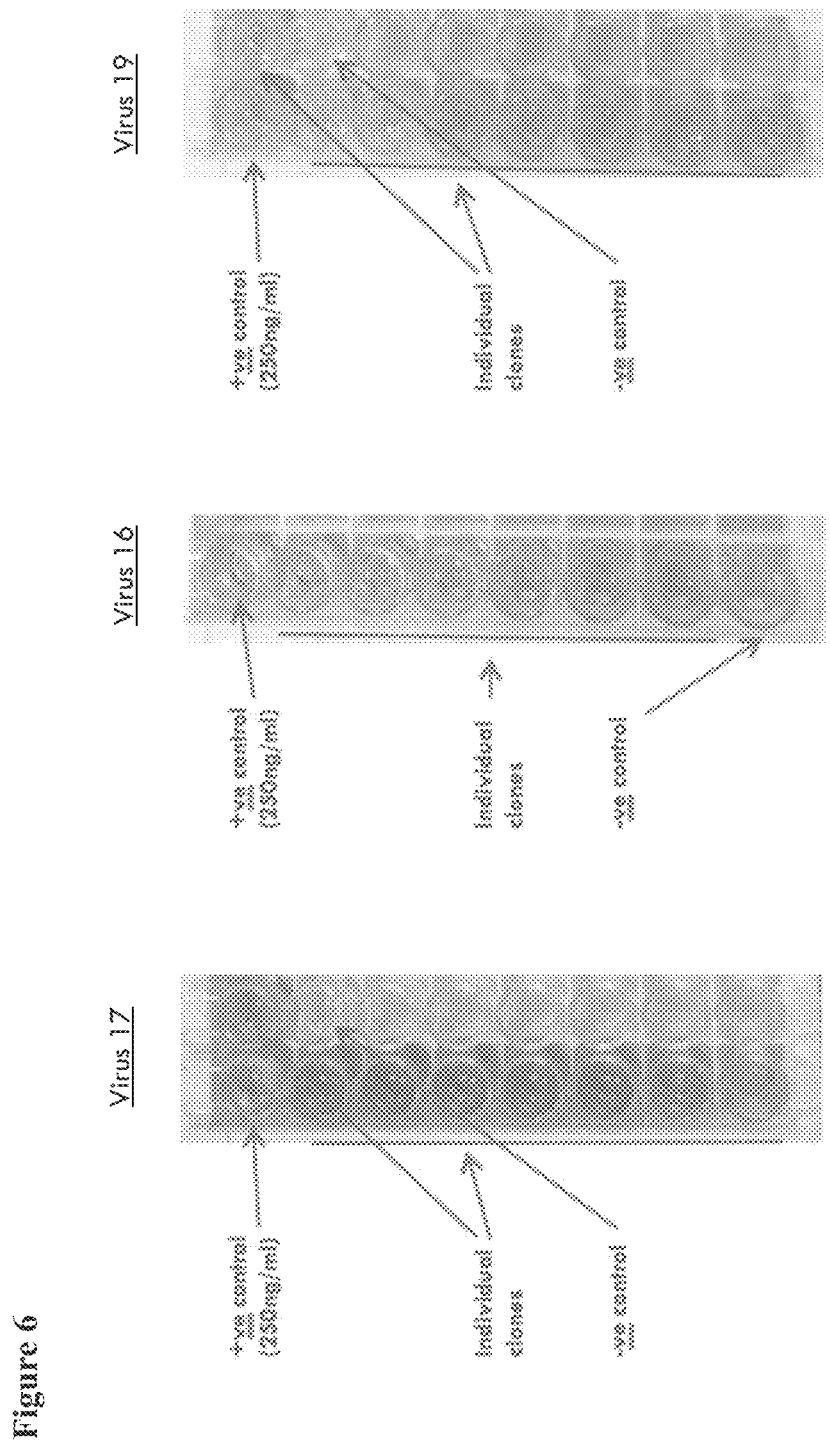
FIG. 6 shows the results of an ELISA to detect expression of human or mouse GM-CSF in supernatants from BHK cells infected with virus 16 (mGM-CSF and GALVR-), virus 17 (hGM-CSF and GALVR-) and virus 19 (mGM-CSF).

For human use, hGM-CSF is used, the sequence for a codon optimised version of which is shown in SEQ ID NO 4. The structure of this virus is shown in FIGS. 4A-4F. Expression of mouse or human GM-CSF from viruses 16, 17 and 19 is shown in FIG. 6.

Figure 7A:
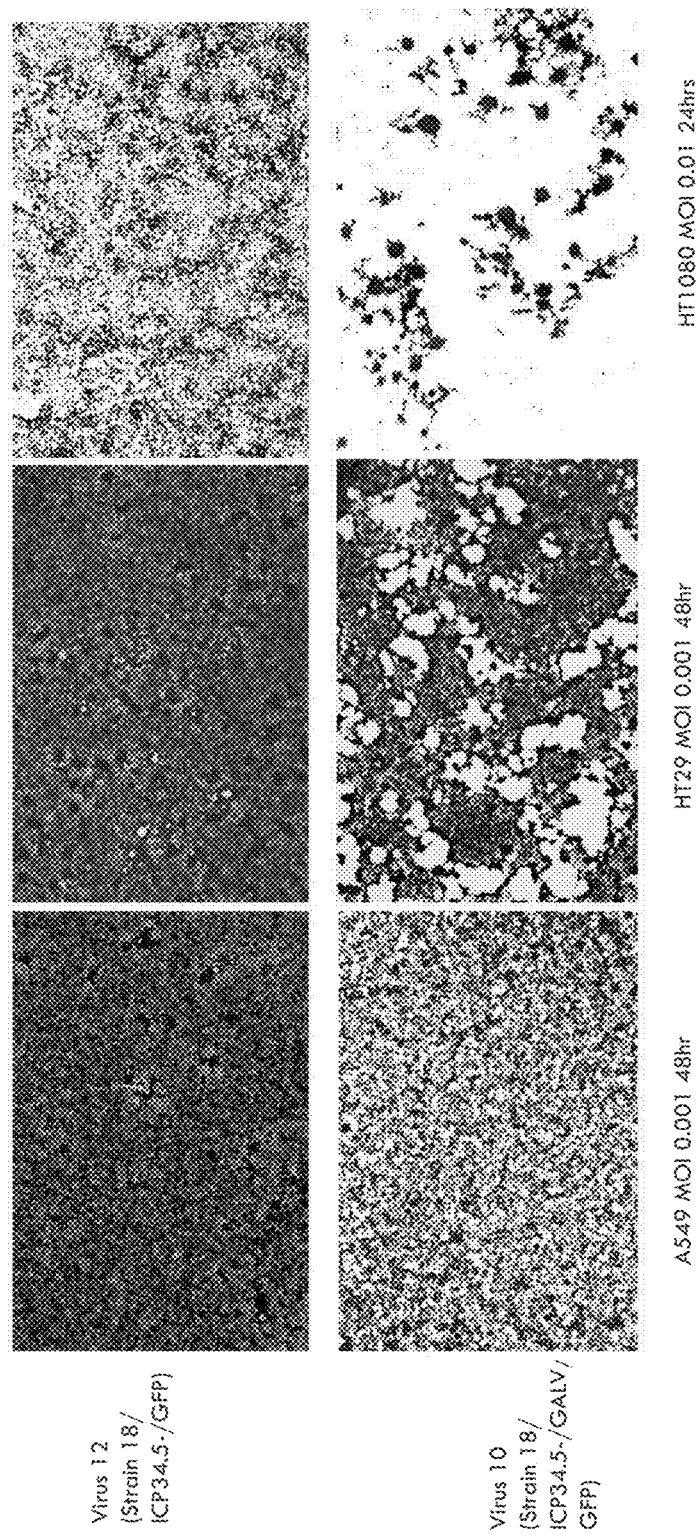
FIGS. 7A-7B is a comparison between the cell-killing abilities of strain RH018A in which ICP34.5 is deleted and which expresses GALVR- and GFP (virus 10) with a virus that expresses only GFP (virus 12) as determined by crystal violet staining in three cell lines at low magnification.
Figure 7B:
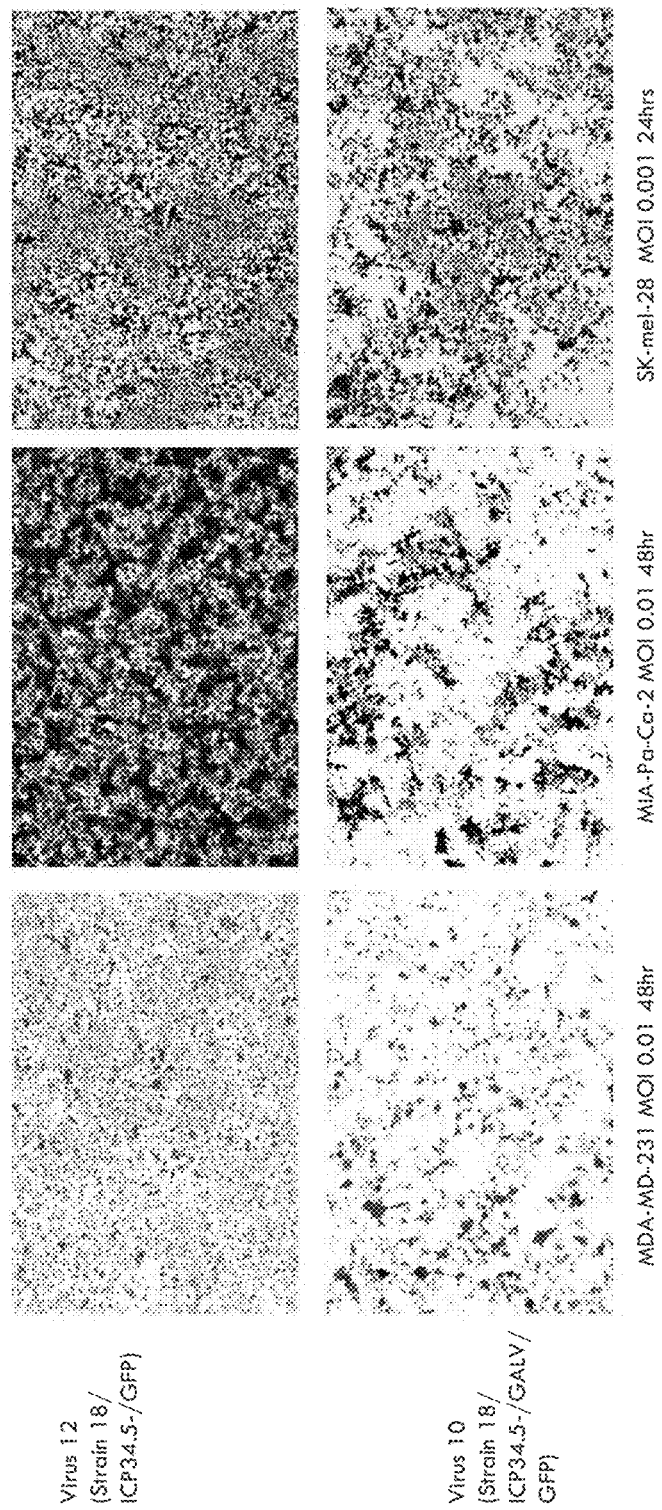

Example 7. A Virus of the Invention Modified for Oncolytic Use and Expressing a Fusogenic Glycoprotein Shows Enhanced Tumor Cell Killing In Vitro as Compared to a Virus which does not Express a Fusogenic Glycoprotein Virus 10 (see FIGS. 4A-4F), based on clinical Strain RH018A in which ICP34.5 is deleted and which expresses GALVR- and GFP, was compared in vitro to a virus which expresses only GFP (Virus 12). Virus 10 showed enhanced killing on a panel of human tumor cell lines as compared to Virus 12, as shown in FIGS. 7A-7B.

Figure 8A:
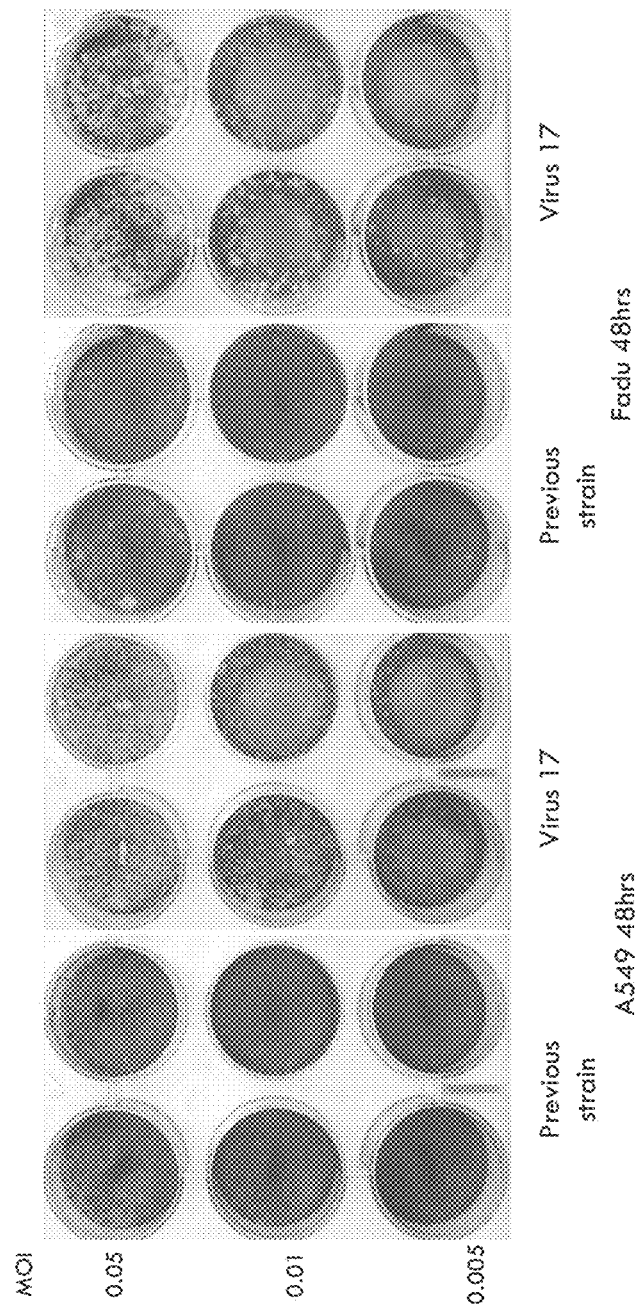
FIGS. 8A-8B is a comparison between the cell-killing abilities of strain RH018A in which ICP34.5 and ICP47 are deleted and which expresses GALVR- and GM-CSF (virus 17) with a prior art strain with the same modifications as determined by crystal violet staining in four cell lines.
Figure 8B:
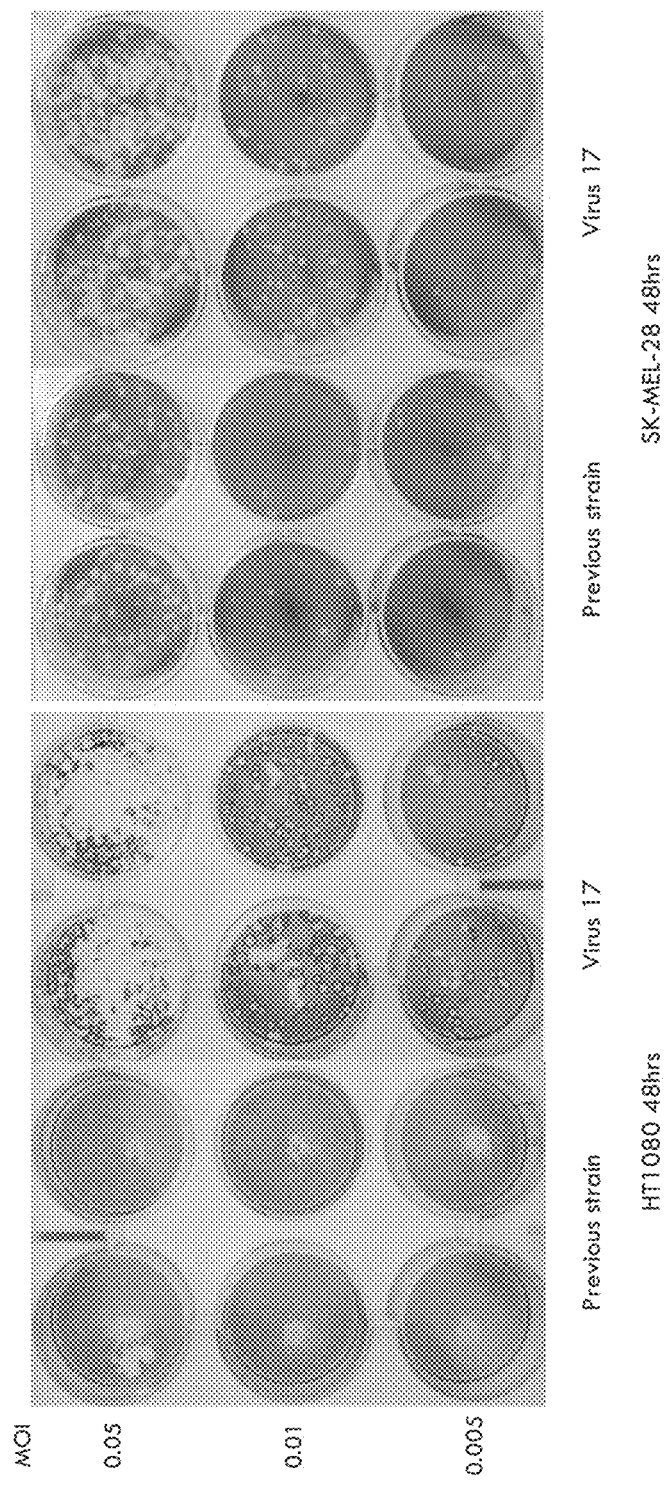

Example 8. A Virus of the Invention Modified for Oncolytic Use Shows Enhanced Tumor Cell Killing as Compared to a Similarly Modified Virus which is not of the Invention Virus 17 (see FIGS. 4A-4F), based on clinical Strain RH018A in which ICP34.5 and ICP47 are deleted and which expresses GALVR- and GM-CSF, was compared in vitro to a known virus which was also deleted for ICP34.5 and ICP47 but which was not derived from a strain of the invention and which expresses only GM-CSF. Virus 17 showed enhanced killing on a panel of human tumor cell lines as compared to the previous virus, as shown in FIGS. 8A-8B.

Figure 9:
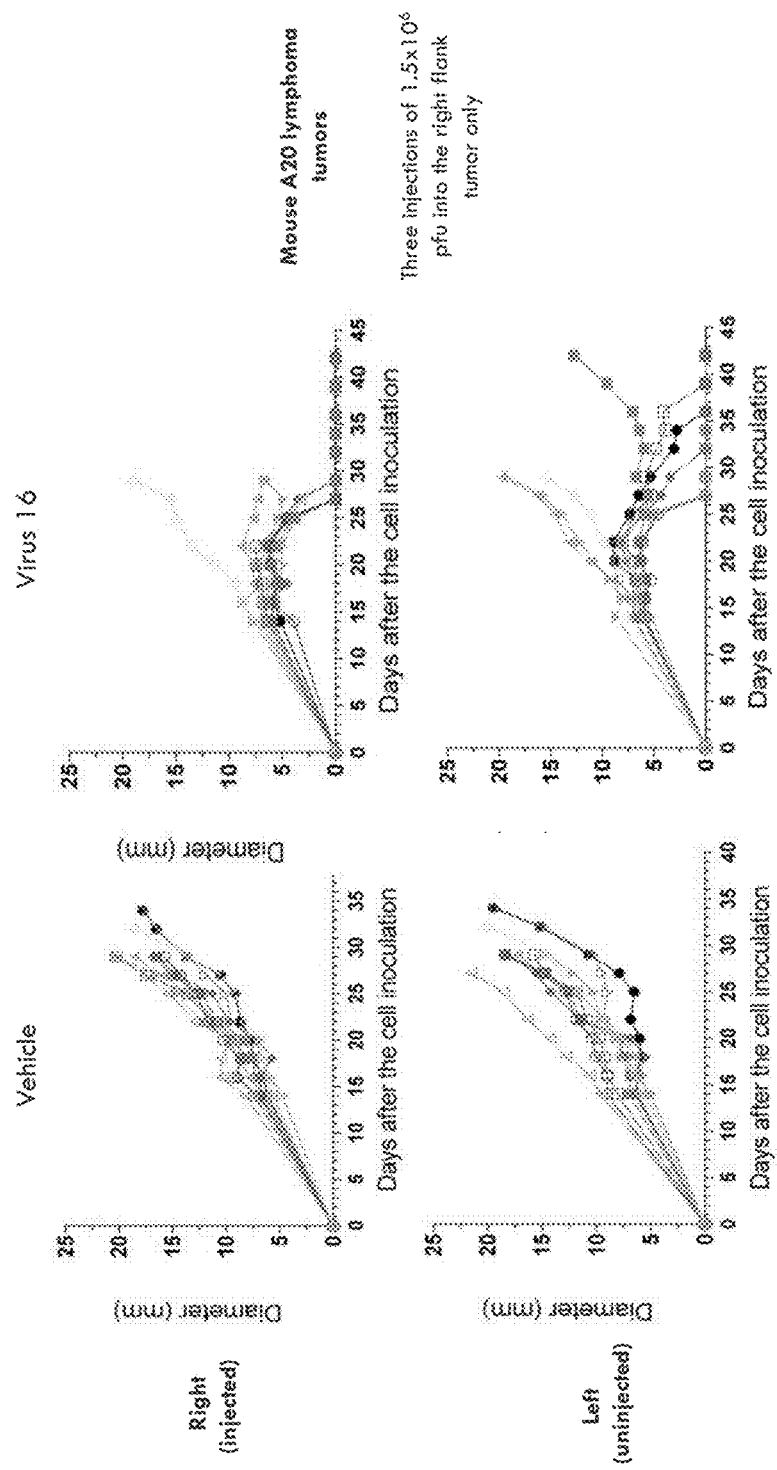
FIG. 9 shows the effectiveness of Virus 16 (ICP34.5 and ICP47 deleted expressing GALVR- and mGM-CSF) in treating mice harbouring A20 lymphoma tumors in both flanks. Tumors on the right flanks were injected with the virus or vehicle and the effects on tumor size was observed for 30 days. The virus was effective against both injected tumors and non-injected tumors.

Example 9. A Virus of the Invention Modified for Oncolytic Use Effectively Treats Mouse Tumors In Vivo Virus 16 was tested in mice harboring A20 lymphoma tumors in the left and right flanks. One million tumor cells were first implanted in both flanks of Balb/c mice and tumors allowed to grow to 0.5-0.7 cm in diameter. Tumors on the right flank were then injected 3 times (every other day) with either vehicle (10 mice) or 5×10 exp 6 pfu of Virus 16 (10 mice), and effects on tumor size observed for a further 30 days. This demonstrated that both injected and uninjected tumors were effectively treated with Virus 16 (see FIG. 9).

Example 10. The Effect of the Combined Expression of a Fusogenic Protein and an Immune Stimulatory Molecule from an Oncolytic Virus of the Invention in a Rat Tumor Model The GALV R- protein causes cell to cell fusion in human cells but not in mouse cells. However, GALV R- does cause fusion in rat cells.

The utility of the invention was further demonstrated by administering 9L cells into the flanks of Fischer 344 rats and allowing the 9L tumors to grow to approximately 0.5 cm in diameter.

The following treatments were then administered to groups of rats (ten per group), into one flank only of each rat three times per week for three weeks:
50 µl of vehicle;
50 µl of $10^7$ pfu/ml of Virus 19 (expresses mGM-CSF but not GALV R-);
50 µl of $10^7$ pfu/ml of Virus 16 (expresses both mouse GM-CSF and GALV-R-).

Figure 10:
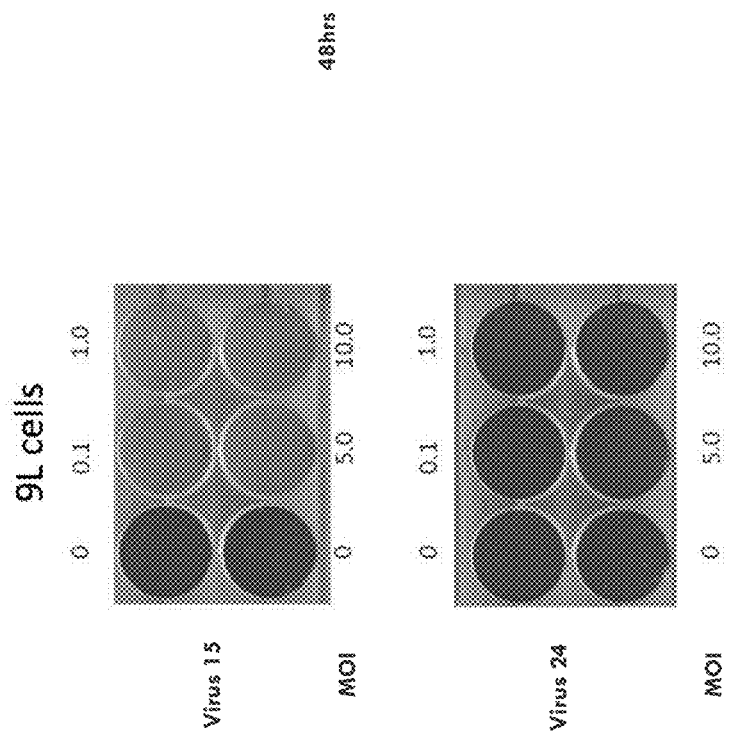
FIG. 10 demonstrates the effects of Virus 15 (ICP34.5 and ICP47 deleted expressing GALVR- and GFP) and Virus 24 (ICP34.5 and ICP47 deleted expressing GFP) on rat 9L cells in vitro as assessed by crystal violet staining. The virus expressing GALV (Virus 15) showed enhanced killing of rat 9L cells in vitro as compared to a virus which does not express GALV (Virus 24).
Figure 15:
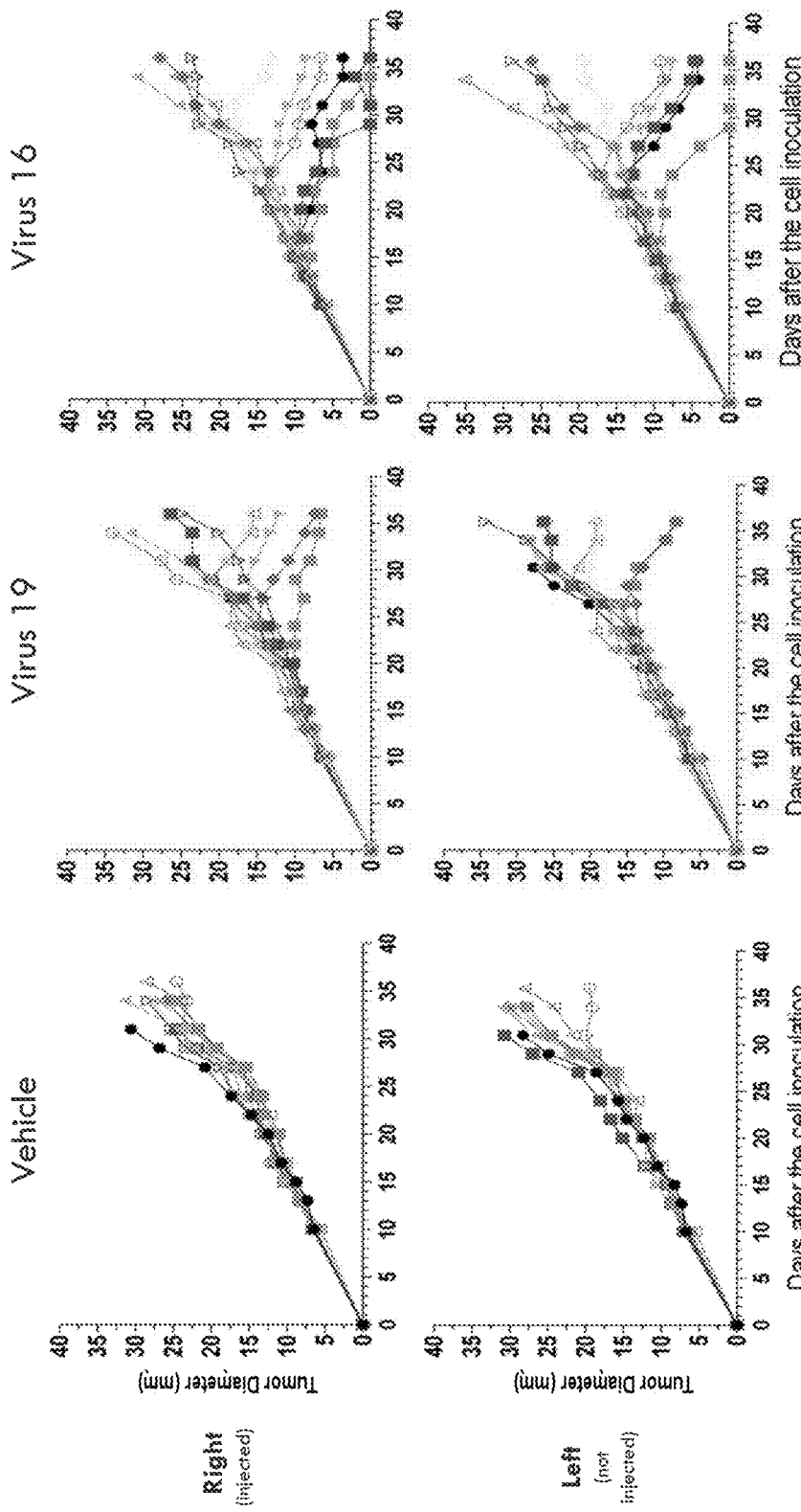
FIG. 15 demonstrates the effects of viruses of the invention expressing GALVR-on 9L cells in the flanks of Fischer 344 rats. The following treatments were administered to groups of rats (ten per group), into one flank of each rat only three times per week for three weeks: 50 µl of vehicle; 50 µl of 10$^7$ pfu/ml of Virus 19 (expresses mGM-CSF but not GALV R-); or 50 µl of 10$^7$ pfu/ml of Virus 16 (expresses both mouse GM-CSF and GALV-R-). Effects on tumor growth were then observed for a further 30 days. Superior tumor control and shrinkage was observed with the virus expressing GM-CSF and GALV-R- as compared to the virus expressing GM-CSF alone.

Effects on tumor growth were then observed for a further ≈30 days. This demonstrated superior tumor control and shrinkage with the virus expressing GALV-R- in both injected and uninjected tumors, demonstrating improved systemic effects. This is shown in FIG. 15. FIG. 10 shows that a virus expressing GALV (Virus 15) also shows enhanced killing of rat 91 cells in vitro as compared to a virus which does not express GALV (Virus 24).

Figure 11B:
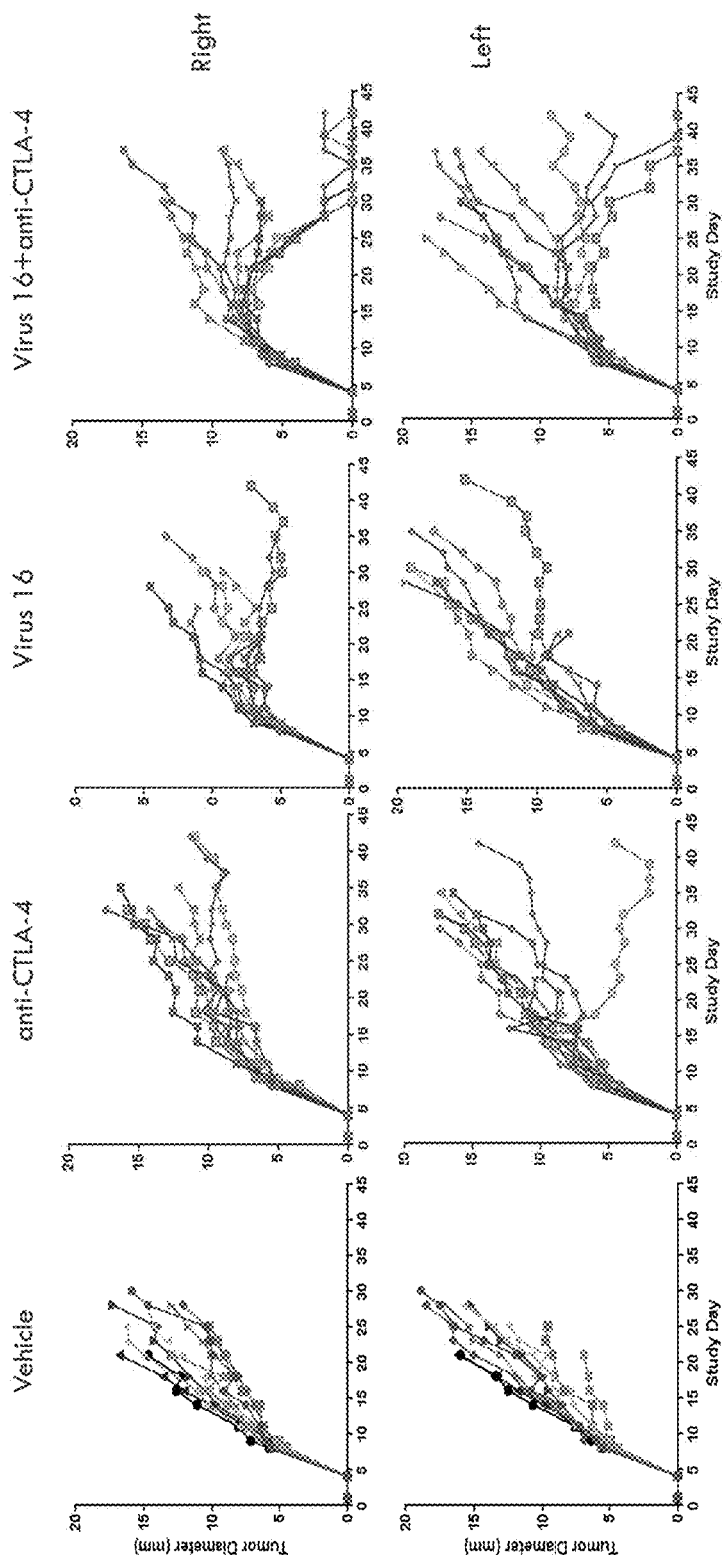
Figure 12A:
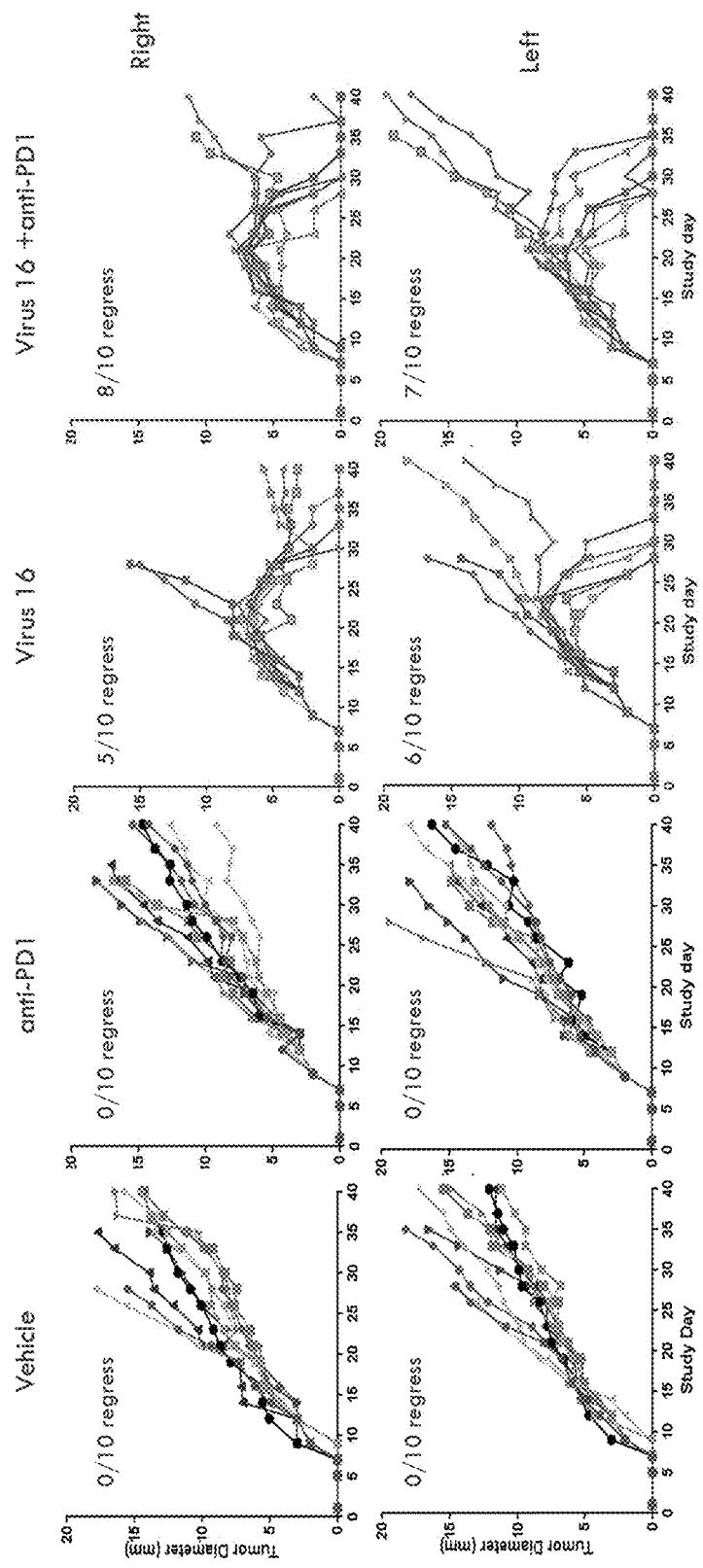
Figure 12B:
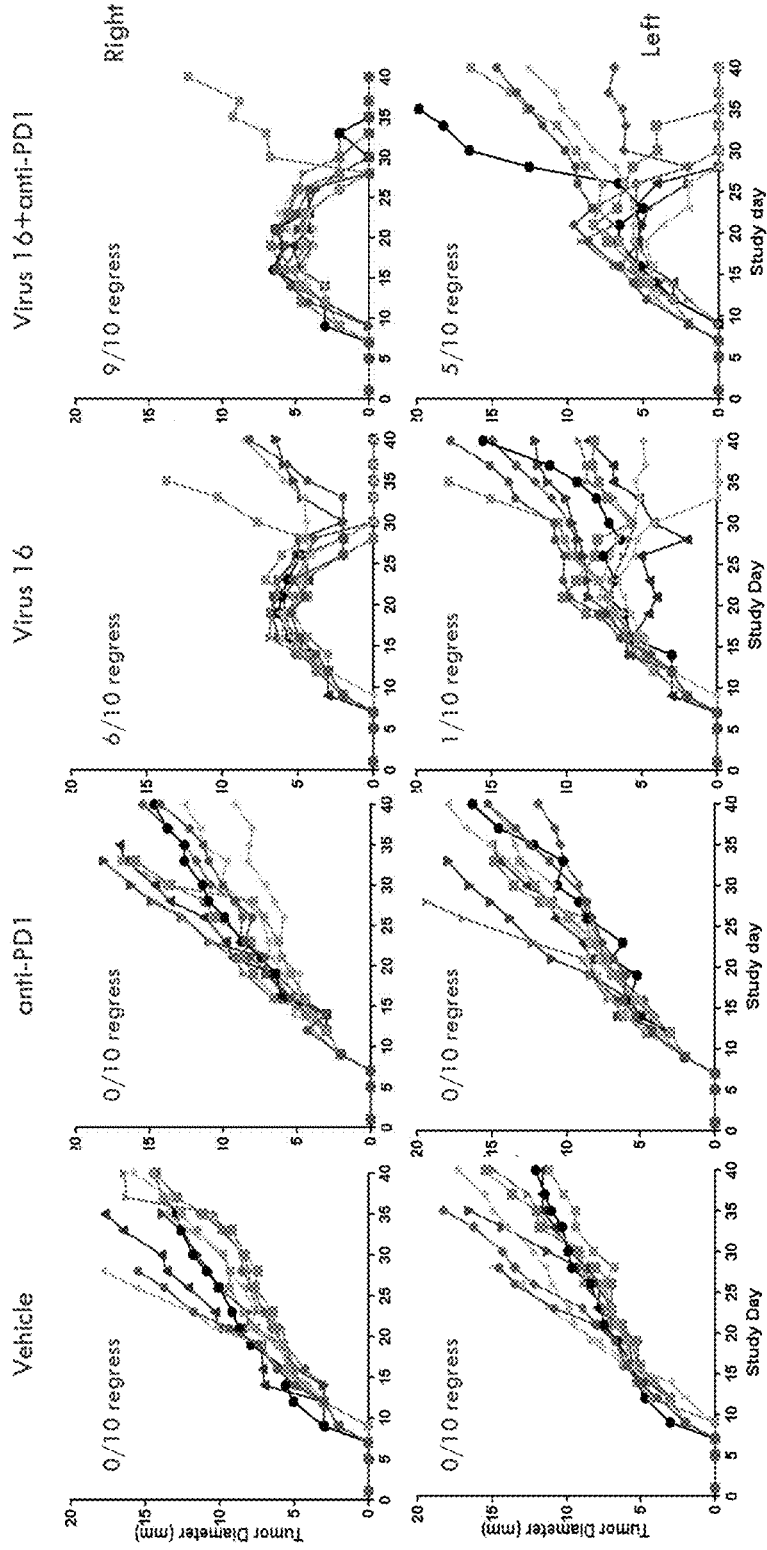
Figure 12C:
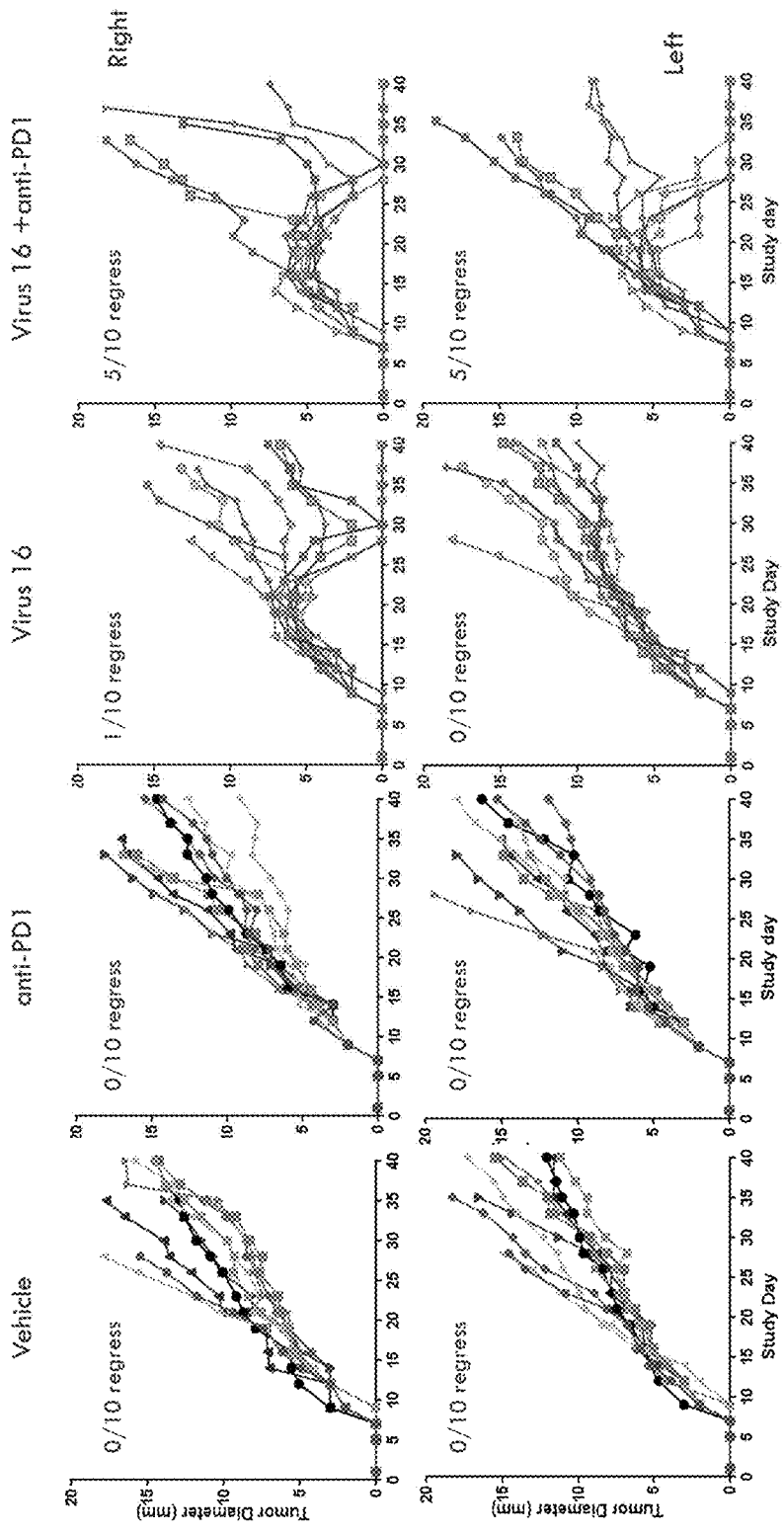

Example 11. A Virus of the Invention Modified for Oncolytic Use is Synergistic with Immune Checkpoint Blockade in Mouse Tumor Models Virus 16 was tested in mice harboring CT26 tumors in the left and right flanks. One million tumor cells were first implanted in both flanks of Balb/c mice and tumors allowed to grow to 0.5-0.6 cm in diameter.
Groups of 10 mice were then treated with:
Vehicle (3 injections into right flank tumors every other day);
5×10 exp 6 pfu of Virus 16 injected in the right flank tumor every other day;
anti-mouse PD1 alone (10 mg/kg i.p. every three days, BioXCell clone RMP1-14);
anti-mouse CTLA-4 (3 mg/Kg i.p every three days, BioXCell clone 9D9);
anti-mouse PD1 together with Virus 16;
anti-mouse CTLA4 together with Virus 16;
1-methyl trypotophan (IDO inhibitor (5 mg/ml in drinking water));
anti-mouse PD1 together with 1-methyl trypotophan;
anti-mouse PD1 together with 1-methyl trypotophan and Virus 16;

Effects on tumor size were observed for a further 30 days. A greater tumor reduction in animals treated with combinations of virus and checkpoint blockade was demonstrated than in animals treated with the single treatment groups (see FIGS. 11A-11C). Enhanced tumor reduction with Virus 16 together with both anti-PD1 and IDO inhibition was also demonstrated as compared to Virus 16 together with only anti-PD1 (see FIGS. 11A-11C).

Enhanced activity of Virus 16 in combination with immune checkpoint blockade was also seen in A20 tumors (FIGS. 12A-12D).

Example 12. The Effect of the Expression of a Fusogenic Protein from an Oncolytic Virus of the Invention in Human Xenograft Models in Immune Deficient Mice The GALV R- protein causes cell to cell fusion in human cells but not in mouse cells. However, human xenograft tumors grown in immune deficient mice can be used to assess the effects of GALV expression on anti-tumor efficacy.

The utility of the invention was therefore further demonstrated by administering A549 human lung cancer cells into the flanks of nude mice and allowing the tumors to grow to approximately 0.5 cm in diameter.

The following treatments were then administered to groups of mice (ten per group), into tumor containing flank of each mouse three times over one week:
50 µl of vehicle;
50 µl of $10^7$ pfu/ml of Virus 16 (expresses both mouse GM-CSF and GALV-R-);
50 µl of $10^6$ pfu/ml of Virus 16;
50 µl of $10^5$ pfu/ml of Virus 16;
50 µl of $10^7$ pfu/ml of Virus 19 (expresses only mouse GM-CSF);
50 µl of $10^6$ pfu/ml of Virus 19;
50 µl of $10^5$ pfu/ml of Virus 19.

Figure 14:
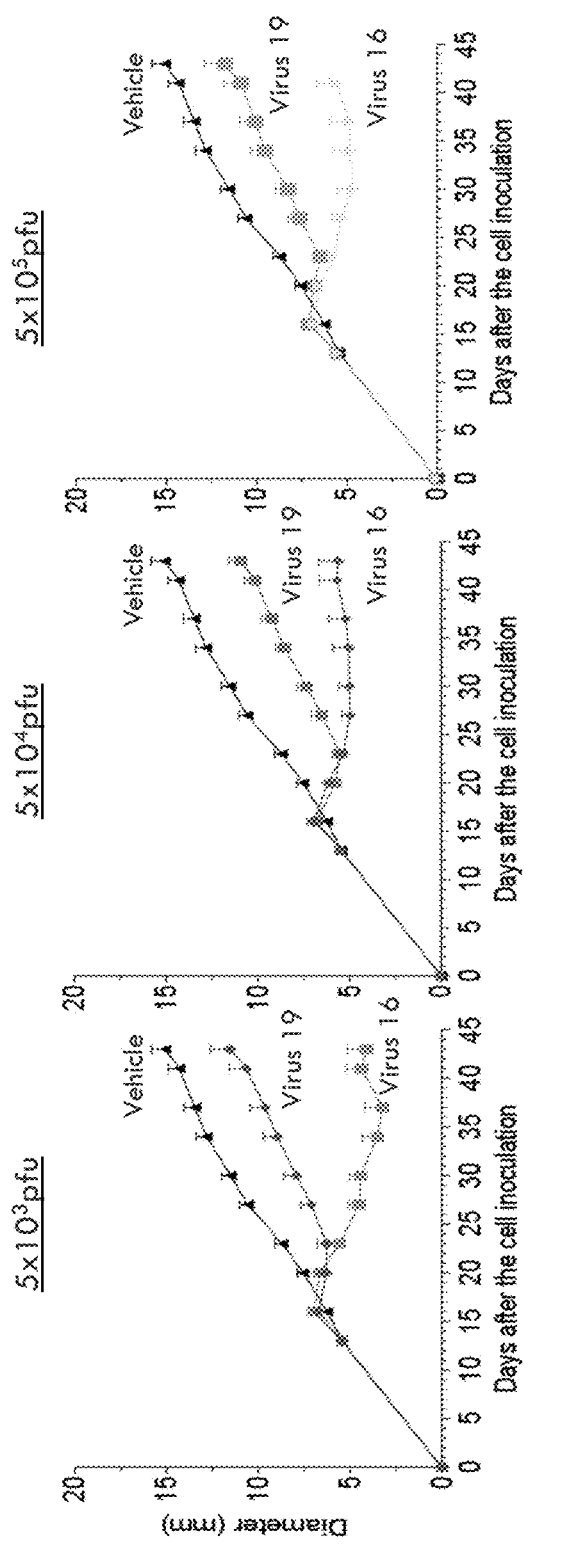
FIG. 14 shows anti-tumor effects of Virus 16 and Virus 19 in a human xenograft model (A549). There were three injections of Virus 16, Virus 19 or of vehicle over one week at three different dose levels (N=10/group). The doses of the viruses used is indicated. The anti-tumor effects of Virus 16 which expresses GALV were better than those of Virus 19 which does not express GALV.

Effects on tumor growth were then observed for a further ≈30 days. This experiment demonstrated superior tumor control and shrinkage with the virus expressing GALV-R- in both tumor models (see FIG. 14).

Figure 13:
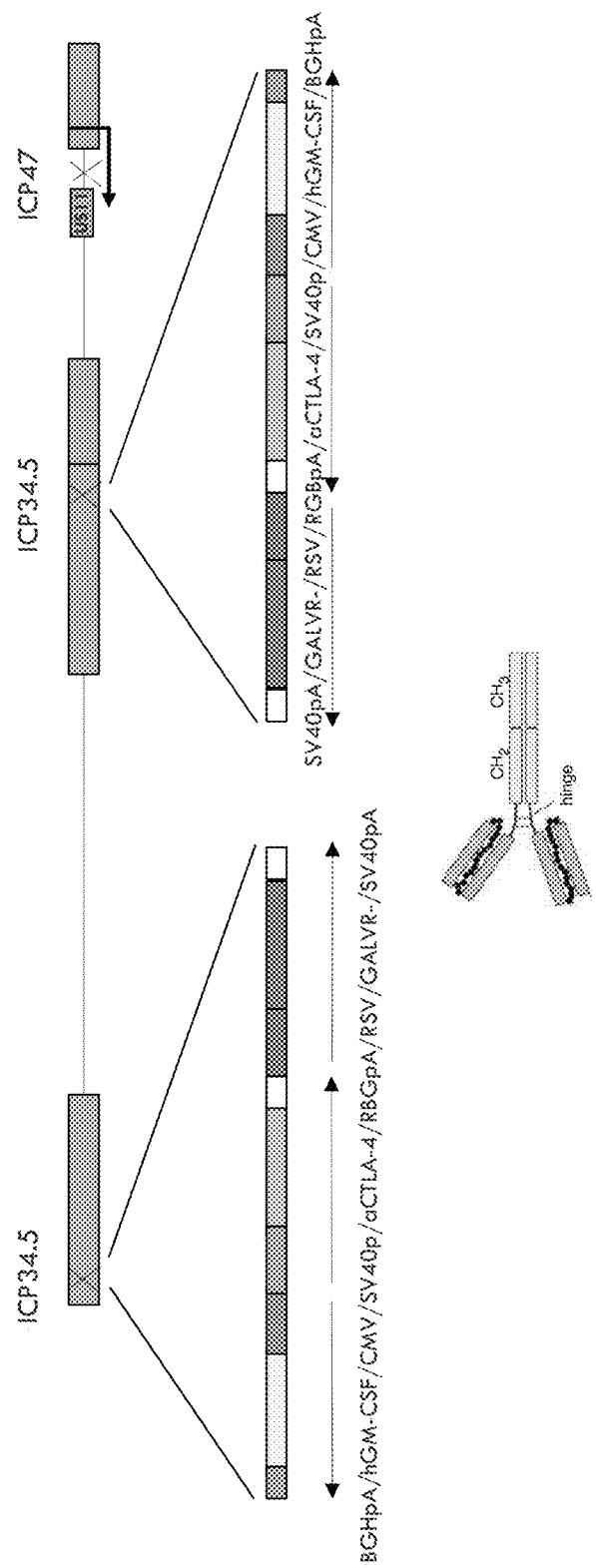
FIG. 13 shows the structure of ICP34.5 and ICP47 deleted viruses expressing GALVR-, GM-CSF and codon optimized anti-mouse or anti-human CTLA-4 antibody constructs (secreted scFv molecules linked to human or mouse IgG1 Fc regions). The scFvs contain the linked ([G$_4$S]$_3$) light and heavy variable chains from antibody 9D9 (US2011044953: mouse version) and from ipilimumab (US20150283234; human version). The resulting structure of the CTLA-4 inhibitor is also shown.
Figure 16:
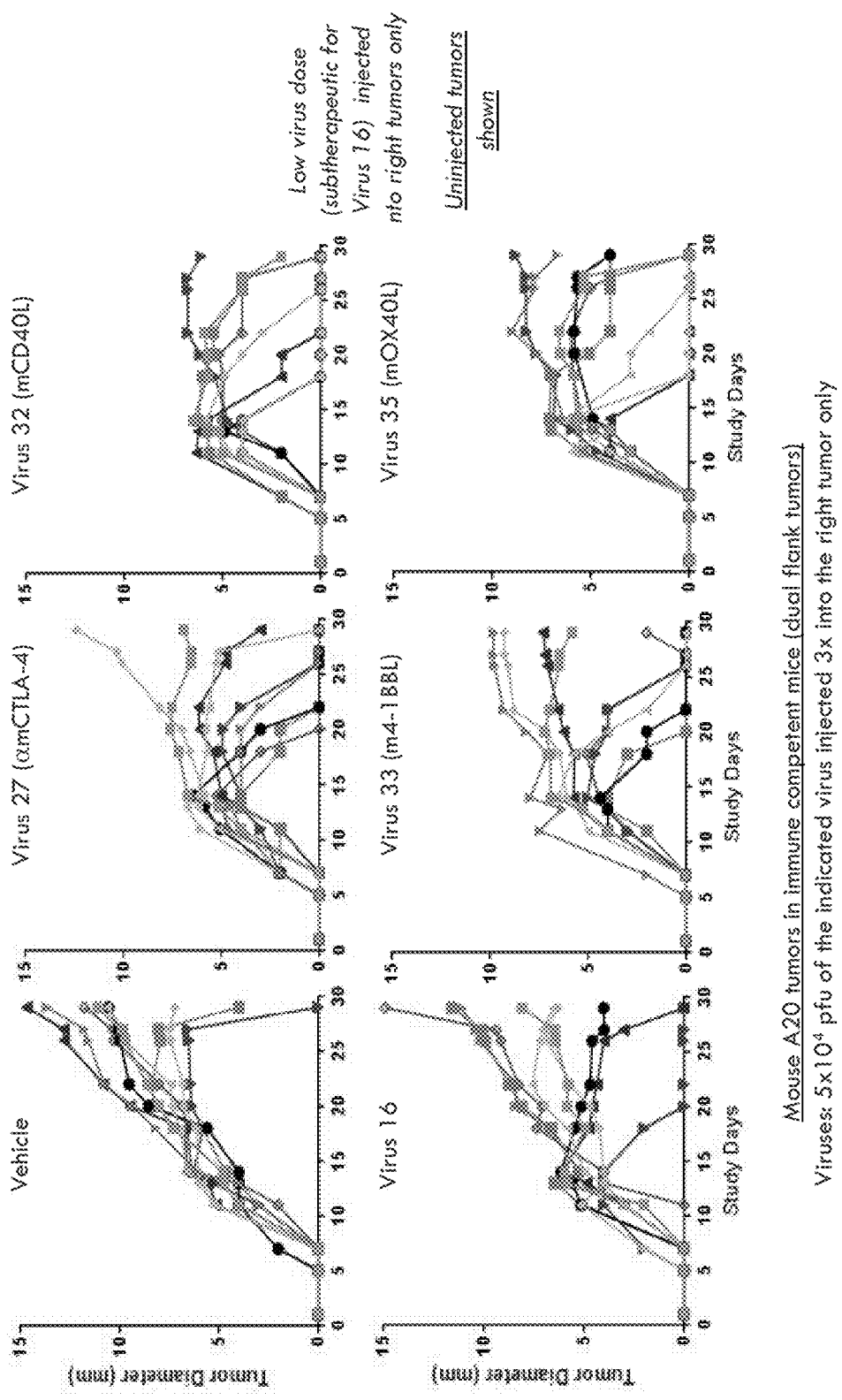
FIG. 16 shows the anti-tumor effects of viruses expressing anti-mCTLA-4 (virus 27), mCD40L (virus 32), mOX4OL (virus 35), m4-2BBL (virus 33), each also with mGM-CSF and GALV-R- compared to virus 16 (expresses GALV and mGM-CSF).

Example 13. Expression of Two Immune Stimulatory Molecules from a Virus Expressing a Fusogenic Protein Viruses similar to the GALV-R- and mGM-CSF expressing virus described above (Virus 16) were constructed, but additionally expressing mouse versions of CD40L (virus 32). ICOSL (virus 36), OX40L (virus 35), 4-1BBL (virus 33) and GITRL (virus 34). Here, instead of using a plasmid containing ICP34.5 flanking regions and an expression cassette comprising GM-CSF and GALV-R- driven by a CMV and an RSV promoter, a plasmid containing ICP34.5 flanking regions and an expression cassette comprising GM-CSF, GALV and the additional proteins driven by a CMV, an RSV and an MMLV promoter respectively were used for recombination with a virus containing GM-CSF, GALV and GFP inserted into ICP34.5. Non-GFP expressing plaques were again selected. Correct insertion was confirmed by PCR, and expression by western blotting and/or ELISA for the additional inserted gene. These viruses are shown in FIGS. 5A-5F. Similarly, viruses expressing anti-mouse and anti-human CTLA-4 in addition to GALV and mGM-CSF were also constructed (Viruses 27 and 31 in FIGS. 5A-5F and see also FIG. 13). Effects of viruses expressing anti-mouse CTLA-4 (virus 27), mCD40L (virus 32), m4-1BBL (virus 33) or mOX40L (virus 35) in addition to mGM-CSF and GALVR- in vivo is shown in FIG. 16 which showed enhanced activity in A20 tumors as compared to virus 16 (expresses mGM-CSF and GALVR-). In these experiments tumors were induced in both flanks of mice, and virus or vehicle injected only into the right flank tumor. The dose of virus used was 5×$10^4$ pfu (50 ul of 1×$10^6$ pfu/ml in each case), given three times over one week. This dose level of virus is subtherapeutic for uninjected tumors for virus 16, which allows the benefits of the delivery of the additional molecules encoded by viruses 27, 32, 33 and 35 to clearly be seen.

Deposit Information

The following HSV1 strains were deposited at the ECACC, Culture Collections, Public Health England, Porton Down, Salisbury, SP4 0JG, United Kingdom on 19 Dec. 2016 by Replimune Limited and were allocated the indicated provisional accession numbers:

RH004A—Provisional Accession Number 16121902
RH015A—Provisional Accession Number 16121903
RH018A—Provisional Accession Number 16121904
RH021A—Provisional Accession Number 16121905
RH023A—Provisional Accession Number 16121906
RH031A—Provisional Accession Number 16121907
RH040B—Provisional Accession Number 16121908
RH047A—Provisional Accession Number 16121909.

The invention claimed is:

1. A method of treating cancer in a subject in need thereof, comprising administering to the subject a therapeutically effective amount of an oncolytic virus encoding a cytotoxic T-lymphocyte-associated antigen 4 (CTLA-4) inhibitor, wherein the virus is a herpes virus.

2. The method of claim 1, wherein the cancer is a solid tumor.

3. The method of claim 1, which comprises administering, concurrently or separately to the virus, a therapeutically effective amount of a further anti-cancer agent to a patient in need thereof.

4. The method according to claim 3, wherein the further anti-cancer agent is selected from an agent targeting an immune co-inhibitory pathway or immune co-stimulatory pathway, radiation and/or chemotherapy, an agent that targets a specific genetic mutation which occurs in tumors, an agent intended to induce an immune response to one or more tumor antigen(s) or neoantigen(s), a cellular product comprising thymus (T) cells or natural killer (NK) cells, an agent intended to stimulate the stimulator of interferon genes (STING), cyclic GMP-AMP synthase (cGAS), toll-like receptor (TLR) or other innate immune response and/or inflammatory pathway, an agent intended to increase or potentiate an immune response, and combinations thereof.

5. The method of claim 4, wherein the further anti-cancer agent is a CTLA-4 inhibitor, a programmed cell death protein 1 (PD-1) inhibitor, a programmed cell death ligand 1 (PD-L1) inhibitor, a lymphocyte activation gene-3 (LAG-3) inhibitor, a T cell immunoglobulin and mucin domain-containing protein 3 (TIM-3) inhibitor, a V-domain immunoglobulin suppressor of T cell activation (VISTA) inhibitor, a colony-stimulating factor 1 receptor (CSF1R) inhibitor, an indoleamine 2,3-dioxygenase (IDO) inhibitor, a killer cell immunoglobulin-like receptor (KIR) inhibitor, a signaling lymphocytic activation molecule F7 (SLAMF7) inhibitor, a carcinoembryonic antigen-related cell adhesion molecule 1 (CEACAM1) inhibitor or a cluster of differentiation 47 (CD47) inhibitor.

6. The method of claim 4, wherein the further anti-cancer agent is a glucocorticoid-induced tumor necrosis factor receptor-related (GITR) agonist, a 4-1-BB agonist, an OX40 agonist, a cluster of differentiation 40 (CD40) agonist or an inducible T cell costimulator (ICOS) agonist.

7. A method according to claim 1, which further comprises administering an inhibitor of the indoleamine 2,3-dioxygenase (IDO) pathway and a further antagonist of an immune co-inhibitory pathway, or an agonist of an immune co-stimulatory pathway.

8. The method of claim 1, wherein the virus further encodes an immune stimulatory molecule.

9. The method of claim 1, wherein the virus comprises genes encoding a CTLA-4 inhibitor and one or more of CD40L, ICOSL, 4-1-BBL, GITRL and OX40L.

10. The method of claim 1, wherein the CTLA-4 inhibitor is a CTLA-4 antibody or fragment thereof.

11. The method of claim 1, further comprising a GM-CSF-encoding gene.

12. The method of claim 1, further comprising a fusogenic protein-encoding gene.

13. The method of claim 12, wherein the fusogenic protein is selected from the group consisting of vesicular stomatitis virus (VSV) G-protein, syncitin-1, syncitin-2, simian virus 5 (SV5) F-protein, measles virus (MV) H-protein, MV F-protein, respiratory syncytial virus (RSV) F-protein and a glycoprotein from gibbon ape leukemia virus (GALV), such as a glycoprotein from gibbon ape leukemia virus (GALV) and has the R transmembrane peptide mutated or removed (GALV-R-), murine leukemia virus (MLV), Mason-Pfizer monkey virus (MPMV) or equine infectious anaemia virus (EIAV) from which the R peptide has been deleted.

14. The method of claim 1, which is a herpes simplex virus (HSV).

15. The method of claim 14, which is a HSV1.

16. The method of claim 14, wherein the HSV:
(a) does not express functional ICP34.5;
(b) does not express functional ICP47; and/or
(c) expresses the US11 gene as an immediate early gene.

17. The method of claim 1, which is a modified clinical isolate, wherein the clinical isolate is a HSV1:
strain RH018A having the provisional accession number ECCACC 16121904;
strain RH004A having the provisional accession number ECCACC 16121902;
strain RH031A having the provisional accession number ECCACC 16121907;
strain RH040B having the provisional accession number ECCACC 16121908;
strain RH015A having the provisional accession number ECCACC 16121903;
strain RH021A having the provisional accession number ECCACC 16121905;
strain RH023A having the provisional accession number ECCACC 16121906; or
strain RH047A having the provisional accession number ECCACC 16121909.

18. The method of claim 1, wherein the sequence of the gene encoding the immune co-stimulatory activating molecules are codon optimized so as to increase expression levels of the respective protein(s) in target cells.

19. The method of claim 1, wherein:
(a) the virus expresses three heterologous genes, wherein each of the three heterologous genes is driven by a different promoter selected from the CMV promoter, the RSV promoter, the EF1a promoter, the SV40 promoter and a retroviral LTR promoter and/or terminated by a different poly adenylation sequence selected from the BGH, SV40, HGH and RBG polyadenylation sequences; or (b) the virus expresses four heterologous genes, wherein each of the four heterologous genes is driven by a different promoter selected from the CMV promoter, the RSV promoter, the EF1a promoter, the SV40 promoter and a retroviral LTR promoter, and/or terminated by a different poly adenylation sequence selected from the BGH, SV40, HGH and RBG poly adenylation sequences.

20. The method of claim 2, wherein the solid tumor is an adenocarcinoma.

21. The method of claim 2, wherein the solid tumor is a carcinoma.

22. The method of claim 2, wherein the solid tumor is a melanoma.

23. The method of claim 2, wherein the solid tumor is a sarcoma.

24. The method of claim 1, comprising administering multiple doses of $10^4$ to $10^{10}$ pfu of the oncolytic virus to the subject.

25. The method of claim 1, wherein the oncolytic virus is administered in an amount effective to induce a systemic anti-tumor immune response.

26. The method of claim 24, wherein the multiple doses of the oncolytic virus are administered to the subject between 3 days to 3 weeks apart.

27. The method of claim 1, comprising administering the oncolytic virus directly into the solid tumor.

28. The method of claim 1, comprising administering the oncolytic virus into a body cavity of the subject.

29. The method of claim 1, comprising intravenously administering the oncolytic virus to the subject.

30. The method of claim 5, wherein the further anti-cancer agent is an anti-PD1 antibody.

31. The method of claim 30, comprising administering the oncolytic virus to the subject prior to administering the anti-PD1 antibody to the subject.

32. The method of claim 31, comprising administering the oncolytic virus to the subject once prior to administering the anti-PD1 antibody to the subject.

33. The method of claim 31, comprising administering the oncolytic virus multiple times to the subject prior to administering the anti-PD1 antibody to the subject.

34. The method of claim 30, comprising administering the oncolytic virus and anti-PD1 antibody to the subject concurrently.

35. The method according to claim 4, wherein the agent intended to increase or potentiate an immune response is a cytokine, a second virus, a second oncolytic virus, or an antibody.

36. The method of claim 12, further comprising a gene encoding an immune stimulatory molecule.

37. The method of claim 12, further comprising a gene encoding an immune co-stimulatory pathway activating molecule.

38. The method of claim 36, further comprising a gene encoding an immune co-stimulatory pathway activating molecule.

39. The method of claim 1, further comprising a gene encoding an immune co-stimulatory pathway activating molecule.

40. The method of claim 39, further comprising a gene encoding an immune stimulatory molecule.

* * * * *